(12) United States Patent
Gustafson et al.

(10) Patent No.: US 11,877,738 B2
(45) Date of Patent: Jan. 23, 2024

(54) METHODS AND DEVICES FOR KNOTLESS SUTURE ANCHORING

(71) Applicant: Medos International Sarl, Le Locle (CH)

(72) Inventors: Adam Gustafson, Dighton, MA (US); Stefan Gabriel, Mattapoisett, MA (US); Benjamin Cleveland, Weymouth, MA (US); Gerome Miller, Randolph, MA (US); Mehmet Z. Sengun, Canton, MA (US); Mollie Rosen, Boston, MA (US); Justin Piccirillo, Uxbridge, MA (US)

(73) Assignee: Medos International Sarl, Le Locle (CH)

( * ) Notice: Subject to any disclaimer, the term of this patent is extended or adjusted under 35 U.S.C. 154(b) by 1102 days.

(21) Appl. No.: 16/577,942

(22) Filed: Sep. 20, 2019

(65) Prior Publication Data

US 2020/0029952 A1 Jan. 30, 2020

Related U.S. Application Data

(63) Continuation of application No. 15/458,018, filed on Mar. 13, 2017, now Pat. No. 10,463,357.

(51) Int. Cl.
*A61B 17/04* (2006.01)

(52) U.S. Cl.
CPC ...... *A61B 17/0401* (2013.01); *A61B 17/0485* (2013.01); *A61B 2017/0403* (2013.01);
(Continued)

(58) Field of Classification Search
CPC ........ A61B 17/0485; A61B 2017/0403; A61B 2017/0409; A61B 2017/0414;
(Continued)

(56) References Cited

U.S. PATENT DOCUMENTS

| 5,690,676 A | 11/1997 | DiPoto et al. |
| 6,319,252 B1 | 11/2001 | McDevitt et al. |

(Continued)

FOREIGN PATENT DOCUMENTS

| CN | 103027737 A | 4/2013 |
| CN | 103619267 A | 3/2014 |

(Continued)

OTHER PUBLICATIONS

Extended European Search Report for EP App. No. 18161249.0 dated Aug. 20, 2018 (9 pages).

(Continued)

*Primary Examiner* — Alexander J Orkin

(57) ABSTRACT

Methods and systems are provided for securing tissue to bone. A surgical system can include a driver device, an elongate shaft receivable within the driver device and having a dilator feature at its distal end, and a capture suture extending through the shaft such that the capture suture's terminal end portions extend to a more proximal position on the driver and the capture suture forms a loop that extends through an opening formed through a side of the shaft. The loop is configured to receive at least one retention suture therethrough and can be tightened by pulling the capture suture's terminal ends, thereby coupling the retention suture with the suture anchor. Once the shaft is inserted into bone and the loop with the retention suture is closed, the suture anchor is driven distally towards the dilator features and into the bone to secure the retaining suture in the bone.

6 Claims, 40 Drawing Sheets

(52) U.S. Cl.
CPC . *A61B 2017/044* (2013.01); *A61B 2017/0409* (2013.01); *A61B 2017/0414* (2013.01); *A61B 2017/0445* (2013.01); *A61B 2017/0458* (2013.01)

(58) Field of Classification Search
CPC ...... A61B 2017/044; A61B 2017/0445; A61B 2017/0458
See application file for complete search history.

(56) References Cited

U.S. PATENT DOCUMENTS

| | | | |
|---|---|---|---|
| 6,527,794 | B1 | 3/2003 | McDevitt et al. |
| 6,544,281 | B2 | 4/2003 | ElAttrache et al. |
| 6,641,596 | B1 | 11/2003 | Lizardi |
| 6,641,597 | B2 | 11/2003 | Burkhart et al. |
| 6,673,094 | B1 | 1/2004 | McDevitt et al. |
| 6,733,506 | B1 | 5/2004 | McDevitt et al. |
| 6,770,073 | B2 | 8/2004 | McDevitt et al. |
| 7,329,272 | B2 | 2/2008 | Burkhart et al. |
| 7,867,264 | B2 | 1/2011 | McDevitt et al. |
| 7,896,907 | B2 | 3/2011 | McDevitt et al. |
| 7,993,369 | B2 | 8/2011 | Dreyfuss |
| 8,012,174 | B2 | 9/2011 | ElAttrache et al. |
| 8,372,124 | B2 | 2/2013 | Paulk et al. |
| 8,430,909 | B2 | 4/2013 | Dreyfuss |
| 8,663,279 | B2 | 3/2014 | Burkhart et al. |
| 8,771,315 | B2 | 7/2014 | Lunn et al. |
| 8,834,543 | B2 | 9/2014 | McDevitt et al. |
| 8,951,292 | B2 | 2/2015 | Paulk et al. |
| 9,005,246 | B2 | 4/2015 | Burkhart et al. |
| 9,113,859 | B2 | 8/2015 | Dooney, Jr. et al. |
| 9,138,220 | B2 | 9/2015 | Hernandez |
| 9,179,907 | B2 | 11/2015 | ElAttrache et al. |
| 9,226,817 | B2 | 1/2016 | Dougherty et al. |
| 9,277,910 | B2 | 3/2016 | Nason et al. |
| 9,295,460 | B2 | 3/2016 | Hoof et al. |
| 9,314,240 | B2 | 4/2016 | Paulk et al. |
| 9,386,977 | B2 | 7/2016 | Lunn et al. |
| 9,393,006 | B2 | 7/2016 | Housman et al. |
| 9,510,820 | B2 | 12/2016 | Hernandez et al. |
| 9,526,488 | B2 | 12/2016 | Arai et al. |
| 9,526,492 | B2 | 12/2016 | Lombardo et al. |
| 9,526,494 | B1 | 12/2016 | Lanois et al. |
| 9,566,060 | B2 | 2/2017 | Dougherty et al. |
| 10,383,618 | B2 | 8/2019 | Gustafson et al. |
| 10,463,357 | B2 | 11/2019 | Gustafson et al. |
| 10,751,161 | B2 | 8/2020 | Diduch et al. |
| 11,446,020 | B2 * | 9/2022 | Gustafson .......... A61B 17/0469 |
| 2006/0253119 | A1 | 11/2006 | Berberich et al. |
| 2008/0208253 | A1 | 8/2008 | Dreyfuss et al. |
| 2009/0281581 | A1 | 11/2009 | Berg |
| 2010/0016893 | A1 | 1/2010 | Fanton |
| 2011/0118762 | A1 | 5/2011 | Dooney, Jr. et al. |
| 2011/0238112 | A1 | 9/2011 | Kim et al. |
| 2011/0264140 | A1 | 10/2011 | Lizardi et al. |
| 2012/0022588 | A1 | 1/2012 | Berg |
| 2012/0150225 | A1 | 6/2012 | Burkhart et al. |
| 2013/0085528 | A1 | 4/2013 | DiMatteo et al. |
| 2013/0123845 | A1 | 5/2013 | Paulk et al. |
| 2013/0150885 | A1 | 6/2013 | Dreyfuss |
| 2013/0267998 | A1 | 10/2013 | Vijay et al. |
| 2014/0277129 | A1 | 9/2014 | Arai et al. |
| 2014/0364906 | A1 | 12/2014 | Palese et al. |
| 2015/0119937 | A1 | 4/2015 | Lunn et al. |
| 2015/0245901 | A1 | 9/2015 | Dougherty et al. |
| 2015/0265327 | A1 | 9/2015 | Berg |
| 2015/0374356 | A1 | 12/2015 | Hernandez |
| 2016/0058551 | A1 | 3/2016 | ElAttrache et al. |
| 2016/0095588 | A1 | 4/2016 | ElAttrache et al. |
| 2016/0128682 | A1 | 5/2016 | Konrath et al. |
| 2016/0235399 | A1 | 8/2016 | Housman et al. |
| 2016/0302785 | A1 | 10/2016 | Nason et al. |
| 2016/0317140 | A1 * | 11/2016 | McCarty, III ...... A61B 17/0401 |
| 2016/0317162 | A1 | 11/2016 | Dougherty et al. |
| 2016/0367357 | A1 | 12/2016 | Dougherty et al. |
| 2016/0374661 | A1 | 12/2016 | Housman et al. |
| 2017/0042530 | A1 | 2/2017 | Lombardo et al. |
| 2017/0172562 | A1 | 6/2017 | Lombardo |
| 2018/0256150 | A1 | 9/2018 | Gustafson et al. |
| 2018/0256151 | A1 | 9/2018 | Gustafson et al. |
| 2019/0343508 | A1 | 11/2019 | Gustafson et al. |
| 2022/0378411 | A1 | 12/2022 | Gustafson et al. |

FOREIGN PATENT DOCUMENTS

| | | |
|---|---|---|
| CN | 104116534 A | 10/2014 |
| CN | 105142540 A | 12/2015 |
| CN | 105559946 A | 5/2016 |
| DE | 60132869 T2 | 2/2009 |
| EP | 2197360 B1 | 6/2018 |
| WO | WO-96/25102 A1 | 8/1996 |
| WO | WO-06099109 A2 | 9/2006 |
| WO | WO-2012161853 A2 | 11/2012 |
| WO | WO-2012177386 A1 | 12/2012 |
| WO | WO-2014165036 A2 | 10/2014 |
| WO | WO-2016/154406 A1 | 9/2016 |

OTHER PUBLICATIONS

Extended European Search Report for EP App. No. 18161275.5 dated Sep. 5, 2018 (9 pages).

Chinese Office Action for CN App. No. 201810204755.1 dated Jun. 23, 2022.

Chinese Office Action for CN App. No. 201810205233.3 dated Jun. 23, 2022.

* cited by examiner

METHODS AND DEVICES FOR KNOTLESS SUTURE ANCHORING

CROSS REFERENCE TO RELATED APPLICATIONS

This application is a continuation of U.S. patent application Ser. No. 15/458,018 entitled "Methods and Devices for Knotless Suture Anchoring" filed on Mar. 13, 2017, which is hereby incorporated by reference in its entirety.

FIELD

The present disclosure relates generally to methods and devices for securing tissue to bone.

BACKGROUND

Tearing of, or the complete or partial detachment of ligaments, tendons and/or other soft tissues from their associated bones within the body are commonplace injuries, particularly among athletes. Such injuries generally result from excessive stresses being placed on these tissues. By way of example, tissue tearing or detachment may occur as the result of an accident such as a fall, over-exertion during a work-related activity, or during the course of an athletic event. In the case of tearing or a partial or complete detachment of soft tissue from a bone, surgery is typically required to reattach the soft tissue (or a graft tissue) to the bone.

Numerous devices have been used to secure soft tissue to bone. Examples of such devices include screws, tacks, staples, suture anchors, and suture alone. In soft tissue repair or re-attachment procedures utilizing suture anchors, an anchor-receiving hole is drilled into bone at the desired point of fixation or tissue re-attachment, and a suture anchor is deployed into the hole using an appropriate installation tool. A suture, coupled to the anchor and passed through or around the soft tissue, thus becomes effectively locked to the bone, which secures the soft tissue to the bone.

During a suture anchoring procedure, it can be challenging to deploy the suture anchor into the anchor-receiving hole. Further, existing suture anchors and inserter devices used to insert the anchors into bone may have certain disadvantages that complicate their use and/or impose certain undesirable limits. Also, procedures that require the suture to be tied into a knot can be time-consuming and cumbersome due to inherent space constraints, which can complicate a surgery.

Accordingly, there is a need for improved methods and systems for attaching tissue to bone.

SUMMARY

In one aspect, a surgical system is provided that in some embodiments includes a driver device, an elongate shaft having a central shaft portion and a distal shaft portion, a capture suture, a suture anchor, and a dilator feature disposed distal to the suture anchor. The driver device has a proximal handle and a driver shaft extending therefrom, the driver shaft having a distal driver member and a lumen extending therethrough. The elongate shaft has a central shaft portion and a distal shaft portion, the elongate shaft being receivable within the lumen of the driver device such that a distal end and at least part of the central shaft portion extend distally from the distal driver member, the central shaft portion having a suture retaining feature that extends therethrough from the distal end of the central shaft portion and that communicates with an opening extending through a side of the central shaft portion. The capture suture extends through the suture retaining feature and the opening such that terminal end portions of the capture suture extend from the driver device and the capture suture forms a loop that extends through the opening. The suture anchor has external threads formed thereon, the suture anchor being removably mountable on the distal driver member. The dilator feature is disposed distal to the suture anchor and has the distal shaft portion at least partially extending therethrough such that a distal end of the elongate shaft extends distally from the dilator feature.

The surgical system can vary in many different ways. For example, the loop of the capture suture can be configured to receive at least one retention suture therethrough, the loop having the retention suture received therethrough being configured to be tightened by pulling the terminal end portions of the capture suture, thereby coupling the retention suture with the suture anchor. As another example, the terminal end portions of the capture suture can extend from a proximal end of the driver device.

In at least some embodiments, the suture retaining feature can be a groove. In at least some embodiments, the distal driver member can be a male feature configured to be received within a corresponding female feature of the suture anchor. In at least some embodiments, the central shaft portion of the elongate shaft has an outer diameter that is greater than an outer diameter of the distal shaft portion of the elongate shaft.

In at least some embodiments, the dilator feature can be made from a non-metallic material. In at least some embodiments, the system further includes a proximal end feature configured to be disposed at a proximal end of the central shaft portion and having at least one retaining feature configured to engage the terminal end portions of the capture suture. The at least one retaining feature can be configured to engage the terminal end portions of the capture suture to tension the capture suture.

In another aspect, a method of performing a surgical repair is provided that in some embodiments includes inserting a distal end of an elongate shaft into a bone, the shaft extending through an implantable dilator feature and a distal driver member of a driver device having a suture anchor releasably coupled thereto that is positioned proximal to the dilator feature, and the elongate shaft having a capture suture extending through a suture retaining feature formed through the elongate shaft and exiting at an opening extending through a side of the elongate shaft such that the capture suture forms a loop that extends through the opening. The method further includes passing a retaining suture coupled to tissue through the loop, closing the loop having the retaining suture passed therethrough by applying tension to the terminal end portions of the capture suture such that the loop retains the retaining suture against a sidewall of the elongate shaft, and driving the suture anchor distally towards the dilator feature and into the bone and thereby secure the retaining suture between the bone and an outer surface of the suture anchor.

The method can vary in many different ways. For example, the capture suture can form the loop such that terminal end portions of the capture suture are adjacent a proximal end of the elongate shaft. As another example, the method can further include closing of the loop prior to inserting the distal end of the elongate shaft into the bone. As another example, the method can further include tensioning the terminal end portions of the capture suture while the distal end of the elongate shaft is inserted into the bone. As yet another example, the method can include removing the capture suture after the suture anchor has been driven into the bone. In at least some embodiments, the method further includes driving the suture anchor distally towards the dilator feature and into the bone using a driver device removably coupled to the suture anchor.

In another aspect, a surgical system is provided that in some embodiments includes an elongate shaft having a central shaft portion and a distal shaft portion, a capture suture, and an implantable dilator. The central shaft portion has a suture retaining feature extending therethrough proximal to a distal shoulder of the central shaft portion, the suture retaining feature communicating with an opening extending through a side of the central shaft portion proximal to the distal shoulder of the central shaft portion. The distal shaft portion extends from the distal shoulder of the central shaft portion to a distal end of the elongate shaft. The capture suture extends through the suture retaining feature of the central shaft portion and the opening such that terminal end portions of the capture suture extend proximal to the opening and the capture suture forms a loop that extends through the opening. The suture anchor is removably disposed on a distal driver member of a driver device having the elongate shaft extending therethrough. The implantable dilator feature is removably disposed on the distal shaft portion distal to the suture anchor such that the distal end of the elongate shaft extends distally from a distal end of the dilator feature.

The surgical system can vary in many different ways. For example, the dilator feature can have a shape of a truncated cone. As another example, the central shaft portion of the elongate shaft can have an outer diameter that is greater than an outer diameter of the distal shaft portion of the elongate shaft.

In one aspect, a surgical system is provided that in some embodiments includes a driver, an elongate shaft, a suture anchor, and a dilator feature. The driver has a proximal handle and a driver shaft extending therefrom, the driver shaft having a distal driver feature and a lumen extending therethrough, and the driver having an opening extending through a side thereof. The elongate shaft is receivable in the lumen of the driver such that a distal portion of the elongate shaft extends distally from the distal driver feature, a central shaft portion of the elongate shaft having a suture retaining feature extending therethrough that communicates with the opening of the driver. The suture anchor has external threads formed thereon, the suture anchor having a lumen extending therethrough that removably receives the central shaft portion therein, wherein the distal driver feature is operably coupled to the suture anchor. The dilator feature is positioned distal to the suture anchor and has the distal portion of the elongate shaft at least partially extending therethrough such that at least a portion of a distal tip of the elongate shaft extends distally from a distal end of the dilator feature.

The surgical system can vary in different ways. For example, the lumen of the suture anchor can be configured to receive at least one suture therethrough such that the suture received therethrough extends proximally from the suture anchor, along the suture retaining feature of the elongate shaft, and through the opening of the driver. As another example, the central shaft portion can have a first outer diameter, and the distal portion extending from the central shaft portion to the distal tip of the elongate shaft can have a second outer diameter that is less than the first outer diameter. As another example, the elongate shaft can be removable from the lumen of the driver.

In at least some embodiments, the opening can be proximal to the distal driver feature. The distal driver feature can extend through the lumen in the suture anchor. In at least some embodiments, the distal driver feature can be a male feature configured to be received within a corresponding female feature formed on at least a portion of an interior wall defining the lumen of the suture anchor.

In at least some embodiments, the elongate shaft has a handle coupled to a proximal end thereof, the handle being disposed proximally to the proximal handle of the driver. In some embodiments, the handle of the elongate shaft and the proximal handle of the driver are independently movable. In at least some embodiments, the dilator feature can have a shape of a truncated cone.

In another aspect, a method of performing a surgical repair is provided that in some embodiments includes inserting a distal end of an elongate shaft into a bone, the shaft extending through an implantable dilator feature, a suture anchor positioned proximal to the dilator feature, and a driver positioned proximal to and coupled to the suture anchor, the driver having an opening extending through a side thereof, wherein a lumen of the suture anchor has terminal end portions of a suture passed therethrough such that the terminal end portions are passed along a suture retaining feature formed in the elongate shaft and the terminal end portions extend through the opening. The method further includes driving the suture anchor distally towards the dilator feature and into the bone and thereby secure the suture between the bone and an outer surface of the suture anchor.

The method can vary in different ways. For example, the method can include maintaining tension on the terminal end portions of the suture while the distal end of the elongate shaft is inserted into the bone. As another example driving the suture anchor distally towards the dilator feature can include rotating a proximal handle of the driver. As a further example, a distal driver feature of the driver can be releasably inserted into the suture anchor when the suture anchor is driven distally towards the dilator feature and into the bone. As a further example, after the suture anchor has been driven distally towards the dilator feature and into the bone, the suture can extend proximally through at least a portion of the lumen in the suture anchor.

In yet another aspect, a surgical system is provided that in some embodiments includes a pusher device, a driver, an elongate shaft, a suture anchor, and an implantable dilator feature. The pusher device has a proximal handle and a shaft extending therefrom, the shaft having a first lumen extending therethrough, and the pusher device having a first opening extending through a side thereof. The driver has a proximal handle and a shaft extending therefrom and having a second lumen extending therethrough, the shaft of the driver extending at least partially through the first lumen of the pusher device, and the driver having a second opening extending through a side thereof, the second opening communicating with the first opening. The elongate shaft is proximally retractably disposed within the second lumen of the driver. The suture anchor has external threads formed thereon, and the suture anchor has a third lumen extending therethrough that removably receives therein a distal driver member of a driver shaft of the driver. The implantable dilator feature is removably disposed on the distal driver member distal to the suture anchor.

The system can vary in different ways. For example, the elongate shaft can be configured to move between a retracted configuration in which a distal end of the elongate shaft is disposed proximal to the second opening, and an advanced configuration in which the distal end of the elongate shaft extends distally from a distal end of the dilator feature. As another example, the elongate shaft can be coupled to a retraction mechanism that is disposed in the proximal handle of the driver and configured to be activated to cause the elongate shaft to move between the retracted configuration and the advanced configuration. As a further example, a distal end of the pusher device abuts a proximal end of the suture anchor.

In at least some embodiments, the system can further include a suture that extends through the dilator feature, through the suture anchor, and through the first and second openings. In at least some embodiments, the proximal handle of the pusher device is disposed distal to the proximal handle of the driver.

In yet another aspect, a method of performing a surgical repair is provided that in some embodiments includes inserting a distal end of a driver shaft of a driver into a bone, the driver shaft extending through an implantable dilator feature, a suture anchor positioned proximal to the dilator feature, and through a pusher device positioned proximal to the suture anchor, the driver shaft having a first opening extending through a side thereof and the pusher device having a second opening extending through a side thereof, wherein a suture coupled to tissue has terminal ends portions thereof passed through the dilator feature, the suture anchor, and through the first and second openings such that the terminal end portions extend from the first and second openings. The method also includes driving the suture anchor distally towards the dilator feature and into the bone and thereby secure the suture between the bone and an outer surface of the suture anchor.

The method can vary in different ways. For example, the suture can be secured between the bone and the outer surface of the suture anchor such that the suture extends proximally through the dilator feature and the suture anchor. As another example, the method can further include maintaining tension on the terminal end portions of the suture while the distal end of the driver shaft is inserted into the bone. As another example, the method can further include maintaining tension on the terminal end portions of the suture while the suture anchor is driven distally towards the dilator feature.

In at least some embodiments, driving the suture anchor distally towards the dilator feature and into the bone includes rotating the driver shaft. In at least some embodiments, the method can further include applying force to the pusher device during at least some of the rotation of the driver shaft.

BRIEF DESCRIPTION OF THE DRAWINGS

The present disclosure will be more fully understood from the following detailed description taken in conjunction with the accompanying drawings, in which.

DETAILED DESCRIPTION

Figure 1:
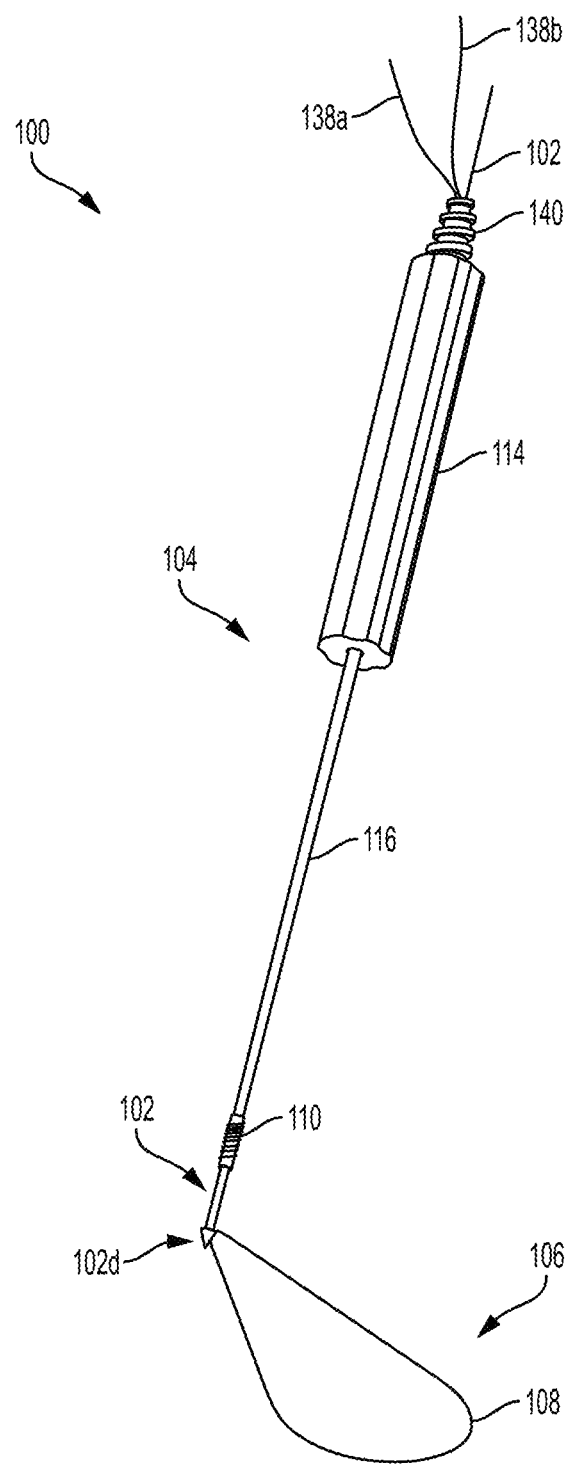
FIG. 1 is a perspective view of one embodiment of a surgical system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various methods and devices are provided for securing tissue to bone. In at least some of the described embodiments, surgical systems are provided that can include a driver device or driver having a lumen extending therethrough, an elongate shaft configured to extend through the lumen of the driver, and a suture anchor having one or more threads formed thereon. The elongate shaft, which can have a dilator feature disposed thereon, can be configured as a self-punching shaft a distal end thereof can initiate a hole in bone. Thus, no additional instruments may be required to initiate the hole. Once the hole in the bone is initiated, the distal end of the elongate shaft can be driven further distally into the hole. For example, a mallet or other suitable instrument can be used for this purpose. The dilator feature, which can be implantable, can assist in widening the hole in the bone as the hole is being formed.

The driver of the surgical system can include a proximal handle and a driver shaft extending from the handle, the driver shaft having a distal driver feature and a lumen extending therethrough. The distal driver feature can be releasably coupled to the suture anchor such that the driver can be activated to thereby cause the distal driver feature to drive the suture anchor distally into bone. Furthermore, in some embodiments, the distal driver feature can be releasably coupled to the dilator feature.

The surgical system can be associated with at least one suture that can then be secured in the bone using the suture anchor. Thus, the surgical system can have one or more components that allow the suture to be coupled to the system. For example, the elongate shaft can include a suture retention feature configured to seat a suture therealong. Also, the surgical system can have one or more openings formed through a side wall of one or more of its components, the opening allowing for passage of the suture therethrough such that the suture can be delivered into the bone using the surgical system. For example, an opening can be formed in the elongate shaft. In some embodiments, the opening can be formed in the driver. Further, in some embodiments where an additional component, such as a pusher device, is used to apply force to the suture anchor to drive the anchor into the bone, openings can be formed in both the pusher device and a driver shaft extending through a shaft of the pusher device. The one or more openings and/or other features configured to receive a suture therethrough or therealong can communicate. For example, if two or more openings are formed, they can be at least partially aligned.

Regardless of the specific configuration, the surgical systems can be configured such that at least one suture, which can be coupled to tissue, can be received through at least a portion of the lumen of the driver feature of driver, with the driver feature having a suture anchor releasably mounted thereto. The suture can be passed through the lumen of the driver feature of driver, and through one or more openings in the component(s) of the system so as to extend out of the openings. In some embodiments, the suture can also be passed along one or more suture retaining features that can be formed in the elongate shaft or in other components. Once the distal end of the elongate shaft is used to initiate a hole in a bone and then driven distally to complete the bone formation, the driver is operated to cause the suture anchor to be driven distally into the bone. While the distal end of the elongate shaft extends distally from a dilator feature, the suture anchor is driven distally towards the dilator feature and into the bone. In this way, the suture is secured and the tissue is attached to the bone. The suture can be secured at least between the bone and an outer surface of the suture anchor, though the suture can be secured in other ways as well.

Furthermore, in some embodiments, a surgical system can include an additional, capture suture that assists in bringing retaining suture coupled to tissue towards a suture anchor of the system. For example, the capture suture, which can be removable, can be coupled to the surgical system such that the capture suture forms a loop. The retaining suture can be passed through the loop, and the loop can be closed by applying tension to terminal end portions of the capture suture. The suture anchor with the retaining suture coupled thereto can then be delivered to bone, such as by operating a driver removably coupled thereto.

In some embodiments, a surgical system for attaching tissue to bone includes a driver device, an elongate shaft having a central shaft portion and a distal shaft portion, a capture suture, and a suture anchor. The surgical system also includes a dilator feature, which can be implantable. The suture anchor and the dilator feature can be cannulated.

The driver device has a proximal handle and a driver shaft extending from the handle. The driver shaft can have a shoulder proximal to a distal driver member, and a lumen extending through the driver shaft. The elongate shaft is receivable within the driver device such that a distal end and at least part of the central shaft portion extend distally from the distal driver member.

The central shaft portion of the elongate shaft can have a suture retaining feature that extends therethrough from the distal end of the central shaft portion and that communicates with an opening extending through a side of the central shaft portion. In some embodiments, the suture retaining feature extends to a termination at the central shaft portion that is proximal to a distal shoulder of the central shaft portion. The suture retaining feature can be, for example, a groove, channel, lumen, or other suitable feature. The distal shaft portion of the elongate shaft extending from the distal shoulder of the central shaft portion can have an outer diameter that is less than an outer diameter of the central shaft portion of the elongate shaft. The distal end of the distal shaft portion is configured to initiate a hole in bone.

The capture suture included in some embodiments extends through the suture retaining feature of the central shaft portion of the elongate shaft and the opening of the elongate shaft such that terminal end portions of the capture suture extend from a more proximal position along the driver device. For example, in some embodiments, the terminal end portions of the capture suture extends from a proximal end of the driver device. The capture suture forms a loop that extends through the opening of the central shaft portion of the elongate shaft. The loop formed by the capture suture is configured to receive at least one retention suture therethrough, and the capture suture loop is configured to be tightened or closed by pulling the terminal end portions of the capture suture. The size of the capture suture loop can be such that the capture suture loop can receive therethrough multiple retention sutures, which can improve the strength of attachment of tissue to bone.

The suture anchor, which can have one or more external threads formed thereon, is removably mountable on the distal driver member of the driver device.

A method for performing a surgical repair to attach or reattach soft tissue to bone is also provided. This method includes creating a hole in bone by inserting a distal end of an elongate shaft into a bone. The elongate shaft can extend through an implantable dilator feature configured to dilate the hole, and through a suture anchor loaded on the driver device proximal to the dilator feature. The elongate shaft can have a capture suture extending through a suture retaining feature formed therethrough and exiting at an opening extending through a side of the elongate shaft and disposed proximal to the dilator feature. The capture suture forms a loop that extends through the opening of the elongate shaft, and the terminal end portions of the capture suture extend proximally, for example, the terminal end portions can extend proximal to the opening. For example, in some embodiments, the terminal end portions of the capture suture can extend from a proximal end of the driver device. In other embodiments, the terminal end portions of the capture suture can extend from a handle or in other ways proximal to the opening of the elongate shaft. The method also includes passing a retaining suture coupled to tissue through the loop, closing the loop by applying tension to the terminal ends of the capture suture such that the loop retains the retaining suture against a sidewall of the elongate shaft, and driving the suture anchor distally towards the distal feature and into the bone and thereby secure the retaining suture between the bone and an outer surface of the suture anchor.

FIGS. 1-9B illustrate one embodiment of a surgical system 100 that includes an elongate shaft 102, a driver or driver device 104 that receives the elongate shaft 102 therethrough, a capture suture 106 forming a loop 108 as discussed below, and a suture anchor 110. The system 100 also includes a dilator feature 112, which can be implantable.

Figure 2:
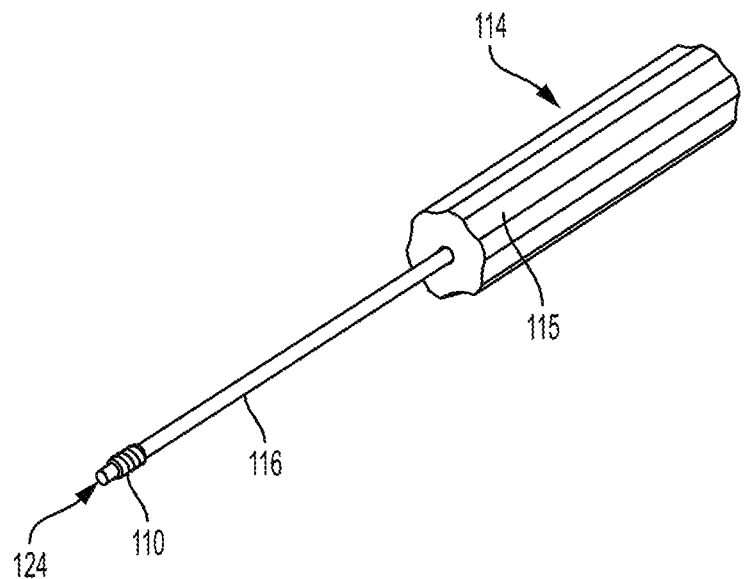
FIG. 2 is a perspective view of a driver device of the surgical system of FIG. 1.
Figure 3:
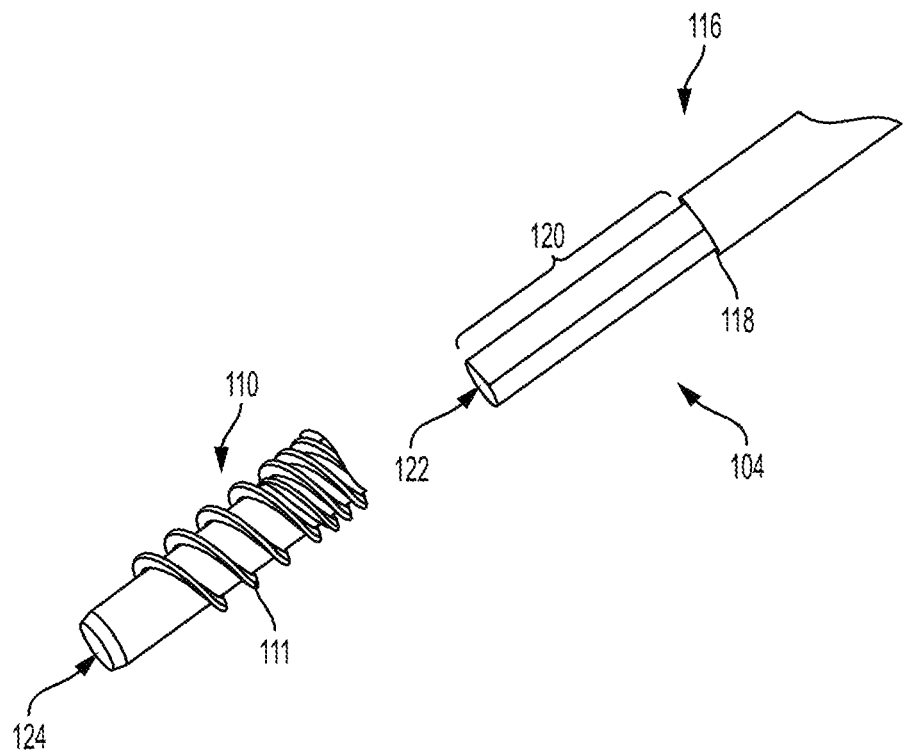
FIG. 3 is a perspective view of a distal portion of the driver device and of a suture anchor of the surgical system of FIG. 1.

The components of the system 100 can have various configurations. As shown in FIGS. 2 and 3, the driver device 104 that is configured to drive the suture anchor 110 into bone has a proximal handle 114 and a driver shaft 116 extending therefrom. The driver shaft 116 can be coupled to the handle 114 in various ways, and it can extend through the handle 114. As shown in FIG. 3, the driver shaft 116 has a shoulder 118 proximal to a distal driver member 120, and a lumen 122 extending therethrough. The driver shaft 116 can have dimensions that are appropriate for a given surgical procedure. For example, the driver shaft can have a diameter in the range of about 1 mm to about 20 mm and a length in the range of about 10 mm to about 0.5 m. The driver member 120 likewise can have dimensions that are appropriate for a given surgical procedure. For example, the distal driver member 120 can have a diameter in the range of about 0.5 mm to about 15 mm, and a length in the range of about 2 mm to about 50 mm.

The proximal handle 114 of the driver device 104 can have a variety of configurations. In the illustrated embodiments, the lumen 122 extends through the driver shaft 116 of the driver device 104 as well as through the length of the proximal handle 114. In other embodiments, the driver shaft 116 can be coupled to the proximal handle 114 in a suitable manner, and a lumen extending through the proximal handle 114 can communicate with a lumen extending through the driver shaft 116.

The proximal handle 114 of the driver device 104 can be configured to have surface features that facilitate grip during use of the driver device 104. For example, as shown in FIGS. 1 and 2, the proximal handle 114 can have grooves 115 formed along its length. It should be appreciated, however, that the proximal handle 114 can have any suitable features, as the described embodiments are not limited in this respect. The dimensions and configuration of the handle 114 can be such that they allow for a convenient grip and efficacy during a surgical procedure.

Figure 5:
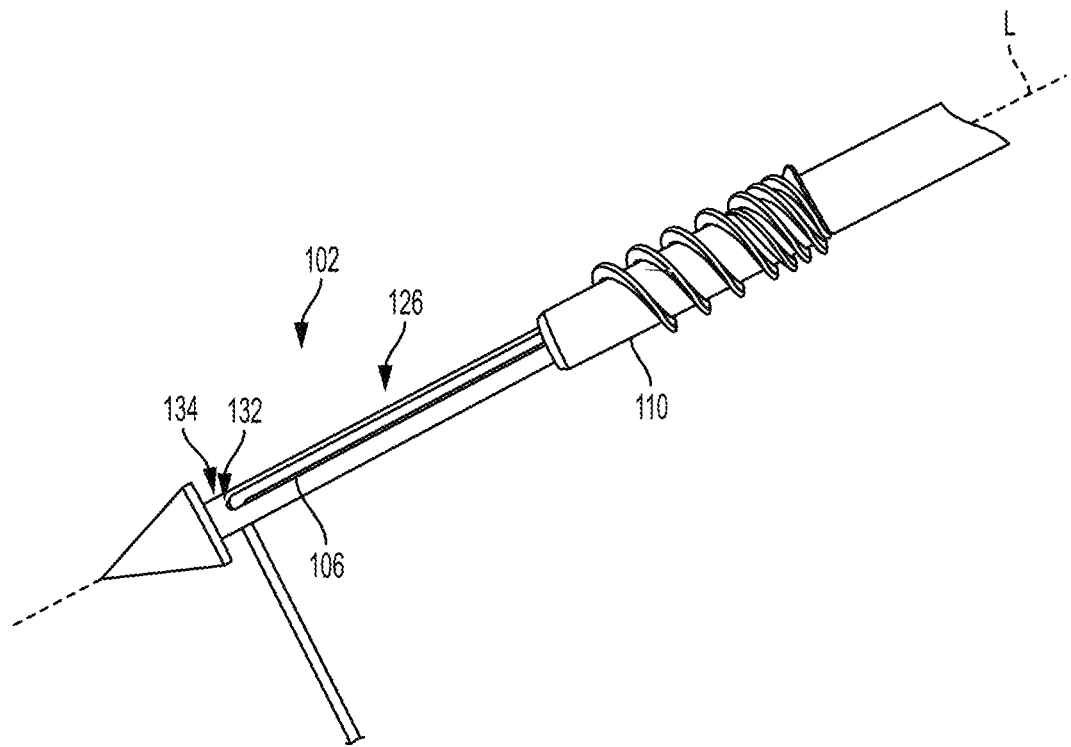
FIG. 5 is a perspective view of a distal portion of the surgical system of FIG. 1.
Figure 6:
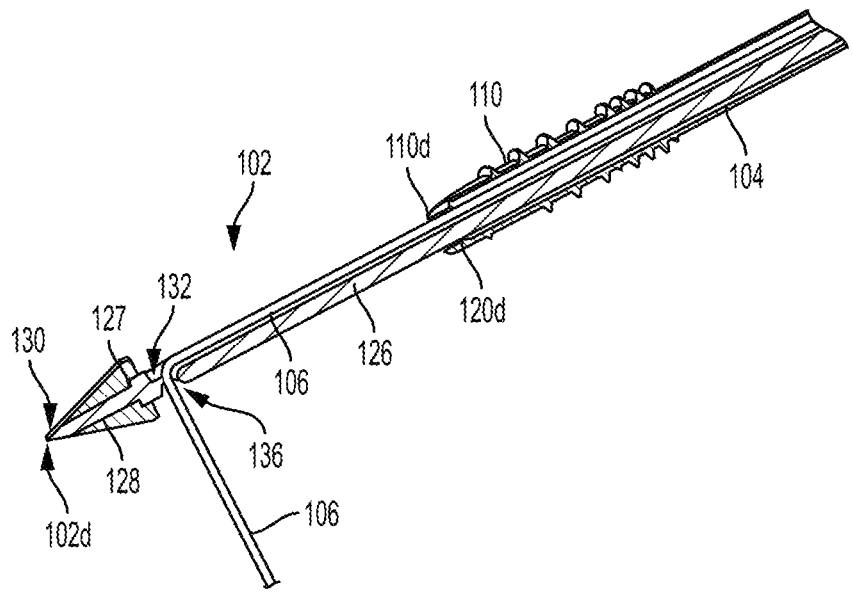
FIG. 6 is a cross-sectional view of the distal portion of the surgical system shown in FIG. 5.

The suture anchor 110 can have various configurations. In the illustrated embodiments, the suture anchor 110 has external threads 111 formed thereon configured to engage the suture anchor 110 with the bone. The suture anchor 110 can have any suitable configuration and can have other bone-engaging features. The suture anchor 110 can have a lumen 124 extending therethrough such that at least in a portion of the lumen 124 can receive therein the distal driver member 120 of the driver shaft 116 of the driver device 104. The lumen 122 of the driver shaft 116 receives the elongate shaft 102 therethrough. In an assembled configuration, as shown in FIG. 6, the distal driver member 120 extends through the suture anchor 110 such that a distal end 120d of the distal driver member 120 (which is also a distal end of the driver shaft 116) is disposed proximal to a distal end 110d of the suture anchor 110. However, in other embodiments, the distal end 120d of the distal driver member 120 can be aligned with or can extend beyond the distal end 110d of the suture anchor 110. In the assembled configuration, as illustrated in FIGS. 1 and 5-7, the suture anchor 110 is mounted on the driver shaft 116 of the driver device 104 such that the suture anchor 110 is proximal to and spaced apart from the dilator feature 112.

The dimensions of the suture anchor 110 can vary depending on the requirements of a given surgical procedure. For example, the suture anchor can have a diameter in the range of from about 1.5 mm to about 15 mm, and a length in the range of from about 5 mm to about 40 mm. The suture anchor 110 can be made from any suitable materials. For example, it can be made from a polymer, examples of which include polyether ether ketone (PEEK), polylactic pcid (PLA), poly(L-lactic acid) (PLLA), etc. Additionally, the polymer can be radiolucent and/or bioabsorbable or biodegradable.

The distal driver member 120 is configured to releasably mate with the suture anchor 110 and to drive the suture anchor 110 mated thereto distally into bone, as discussed in more detail below. In some embodiments, as illustrated herein, the distal driver member 120 can be in the form of a male feature configured to be received within a corresponding female drive feature of the suture anchor 110. In the illustrated embodiment, as shown in FIG. 3, the male feature is hexagonal-shaped, and the corresponding female drive feature of the suture anchor 110 can be a corresponding hexagonal-shaped female drive feature formed in at least a portion of the lumen 124 of the suture anchor 110.

Figure 4:
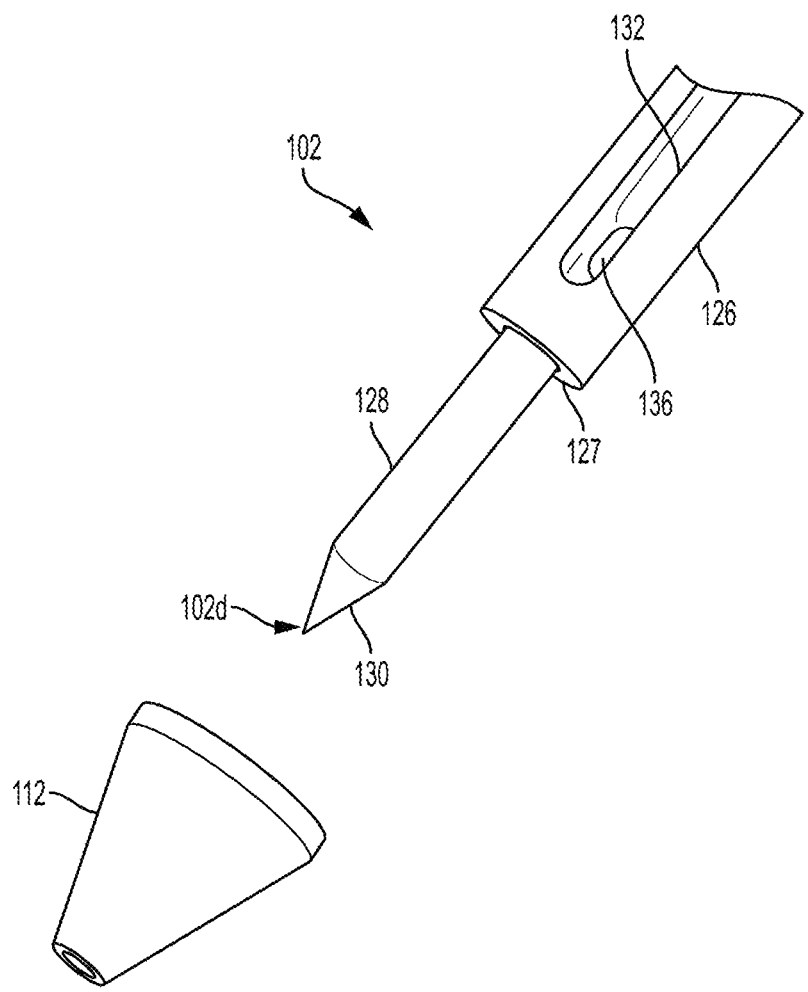
FIG. 4 is a perspective view of a portion of an elongate shaft and a cannulated dilator feature of the surgical system of FIG. 1.

In the illustrated embodiment, as shown in FIG. 4, the elongate shaft 102 has a central shaft portion 126 and a distal shaft portion 128 extending distally from a distal shoulder 127 of the central shaft portion 126 and terminating at the distal end 102d of the elongate shaft 102. It should be appreciated that in other embodiments, the distal shoulder 127 may not be formed. As also shown in FIG. 4, the distal shaft portion 128 can include a distal awl tip portion 130, which is, in this example, distally tapered.

The dimensions of the central shaft portion 126 and the distal shaft portion 128 can vary depending on the requirements of a given surgical procedure. In the illustrated embodiment, the central shaft portion 126 of the elongate shaft 102 can have an outer diameter that is greater than an outer diameter of the distal shaft portion 128 of the elongate shaft 102. For example, in at least some embodiments, the central shaft portion 126 can have a length in a range of from about 10 mm to about 300 mm, and an outer diameter in a range from about 1 mm to about 15 mm. For another example, in at least some embodiments, the distal shaft portion 128 can have a length in a range of from about 1 mm to about 50 mm, and an outer diameter in a range from about 0.5 mm to about 20 mm.

The elongate shaft 102 can be received within the driver device 104 such that a distal shaft portion 128 terminating with the distal end 102d, and at least a part of the central shaft portion 126 of the elongate shaft 102 extend distally from the distal driver member 120. In the illustrated embodiments, the elongate shaft 102 is configured to be inserted into bone to initiate a hole. Thus, there is no need to initiate a hole in the bone using other instruments.

In the illustrated embodiment, the central shaft portion 126 of the elongate shaft 102 has a suture retaining feature 132 extending therethrough that is configured to seat the capture suture. As shown in FIG. 4, the suture retaining feature 132 can extend from the opening 136 extending through a side of the central shaft portion 126 of the elongate shaft 102. The suture retaining feature 132 can extend to a termination at the central shaft portion 126 that is proximal to the opening 136 formed in the central shaft portion 126.

The suture retaining feature 132 can have any suitable configuration and can be formed in any suitable manner in the elongate shaft 102 so as to seat the capture suture 106. In the illustrated embodiment, as shown in FIGS. 4-6, the suture retaining feature 132 can be in the form of a groove formed along or parallel to a longitudinal axis L of the elongate shaft 102. The groove can be formed in the outer surface of the central shaft portion 126. However, in other embodiments, the suture retaining feature 132 can be in the form of a channel, lumen, or other suitable feature.

In the illustrated embodiment, the surgical system 100 includes the dilator feature 112 that is distal to the suture anchor 110. The distal shaft portion 128 of the elongate shaft 102 is configured to extend through the dilator feature 112 (shown separately in FIG. 4) such that the distal end 102d of the elongate shaft 102 extends distally from a distal end 112d of the dilator feature 112. The dilator feature 112 is configured to facilitate insertion of the elongate shaft 102 into bone by enlarging the dimensions of a hole in bone initially formed by the distal end 102d of the elongate shaft 102. In this example, the dilator feature 112 is distally tapered and is in the form of a truncated cone, though it can have other configurations. The dilator feature 112 can be press-fit onto or otherwise coupled with the elongate shaft 102 (e.g., via a threaded connection or via other suitable mating feature(s)). The dilator feature 112 may lack surface features, as in the illustrated example. However, in some embodiments, the dilator feature 112 can have one or more surface features that facilitate its engagement with the bone. The dilator feature 112 can have any suitable dimensions. For example, in at least some embodiments, the dilator feature 112 can have an outer diameter of about or less than 12 mm and a length of about or less than 15 mm.

In some embodiments, the dilator feature 112 can be implantable and it can be made from a non-metallic material. This can be beneficial since the properties of non-metallic materials are such that they would not interfere with post-implantation imaging of the repair done using system 100. Moreover, while it is sufficiently rigid to assist in forming a bone hole, the dilator feature 112 can be bioabsorbable and/or biodegradable. However, in other embodiments, the dilator feature 112 can be made from a metal.

In the illustrated embodiments, a soft tissue (e.g., a torn ligament, a graft tissue, etc.) can be attached to associated bone using one or more retaining sutures and the suture anchor. The retaining sutures can be coupled to the central shaft portion of the elongate shaft via the capture suture coupled to the surgical system, as discussed in more detail below.

Figure 7:
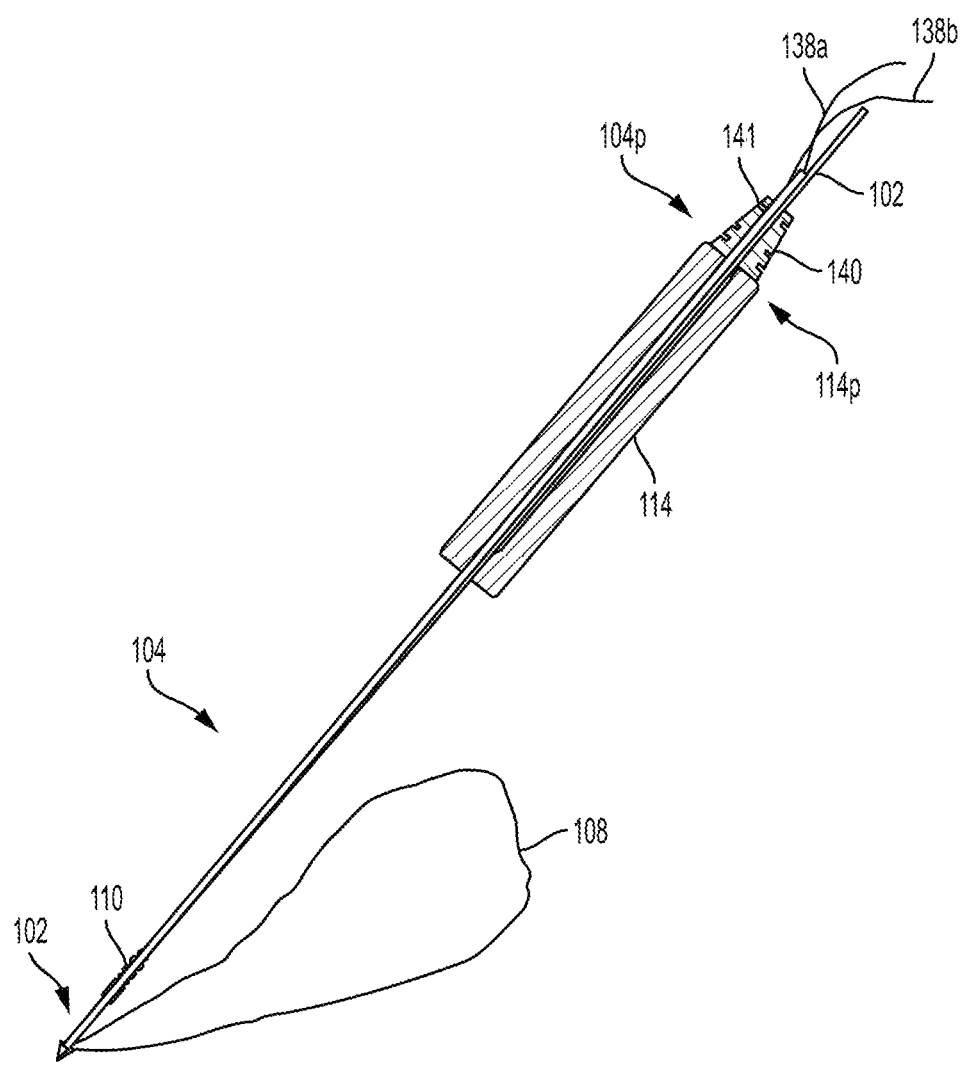
FIG. 7 is a cross-sectional view of the surgical system of FIG. 1.

As shown in FIGS. 1 and 7, the capture suture 106 included in the surgical system 100 extends along the suture retaining feature 132 of the central shaft portion 126 of the elongate shaft 102 and out of the opening 136. In the illustrated embodiment, terminal end portions 138a, 138b of the capture suture 106 extend from a proximal end 104p of the driver device 104. However, the described techniques are not limited to the way in which the terminal end portions 138a, 138b extend proximally to the loop 108. Thus, the terminal end portions 138a, 138b can extend in different ways proximal to the opening 136 and at least a portion of the suture retaining feature 132. For example, in some embodiments, the terminal end portions 138a, 138b of the capture suture 106 can extend from the handle 114 that can be configured to allow the terminal end portions 138a, 138b to extend therefrom. Regardless of the way in which the terminal end portions 138a, 138b of the capture suture 106 are positioned, they can be positioned such that tensioned can be applied thereto during a surgical procedure, as discussed in more detail below.

The capture suture 106 forms the loop 108 that extends through the opening 136. The capture suture 106 is seated along the suture retaining feature 132 of the elongate shaft 102 from the proximal end of the suture retaining feature 132 towards the opening 136 and back from the opening 136 towards the proximal end of the suture retaining feature 132. The loop 108 is configured to receive at least one retention suture therethrough, as discussed in more detail below. The size of the loop 108 can vary depending on a particular surgical procedure. For example, in some embodiments, the loop 108 can be as sufficiently large to allow a surgeon to pass his or her hand therethrough. Also, the size of the loop 108 is adjustable such that the loop 108 is configured to be tightened or closed by pulling the terminal end portions 138a, 138b of the capture suture 106, thereby bringing the retention suture against the side wall the central shaft portion 126 of the elongate shaft 102.

The surgical system 100 can have other various features that assist in operation of the system 100 to attach soft tissue to bone. For example, the surgical system 100 can include a proximal end feature 140 attached at or near the proximal end of the central shaft portion 126 of elongate shaft 102, e.g., by press-fit, threaded coupling, or by other type of coupling, including a non-movable coupling. In the illustrated embodiment, the proximal end feature 140 is positioned proximal to the proximal handle 114 of the driver device 104. The proximal end feature 140 can have at least one retaining feature, such as, for example, notches 141 that are configured to engage the terminal end portions 138a, 138b of the capture suture 106. It should be appreciated that the retaining feature can be in any other suitable form—e.g., grooves, ridges, hooks, clamps etc. The retaining feature 141 is configured to engage the terminal end portions 138a, 138b of the capture suture 106 to tension the terminal end portions 138a, 138b, as discussed in more detail below. It should be appreciated that the proximal end feature 140, configured to facilitate applying and maintaining tension on the terminal end portions 138a, 138b of the capture suture 106, is shown by way of example only. Thus, in other embodiments, another type of feature can be used. As another alternative, such a proximal end feature may not be used.

In the assembled configuration of the surgical system 100 shown in FIGS. 1 and 5-7, the elongate shaft 102 extends through a lumen in the cannulated driver device 104, in particular, through the central lumen 122 extending through the proximal handle 114 and the driver shaft 116. The distal end 102d and a portion of the central shaft portion 126 of the elongate shaft 102 extend distally from the distal driver member 120. The capture suture 106 extends through the suture retaining feature 132 of the central shaft portion 126 of the shaft 102, between the proximal end of the suture retaining feature 132 and the opening 136, such that a mid-portion of the capture suture 106 forms the loop 108 extending from the opening 136. In this configuration the terminal end portions 138a, 138b extend from the proximal end of the driver device 104. The suture anchor 110 is removably mountable on the driver member 120 such that the proximal end of the suture anchor 110 abuts the shoulder 118. Also, at least a portion of the driver shaft 116 extends into the lumen 124 in the suture anchor 110 such that the distal driver member 120 is mated with at least a portion of the lumen 124. In addition, the proximal end feature 140 is proximal to a proximal end 114p of the proximal handle 114. The elongate shaft 102, driver device 104, the suture anchor 110, and the dilator feature 112 are axially aligned such that longitudinal axes of these components coincide. In the assembled configuration, the system 100 can include the driver device 104, which receives the elongate shaft 102, and the suture anchor 110 that is pre-loaded onto the distal driver member 120 of driver shaft 116. However, in some embodiments, the driver device 104 may not be part of the assembly, and various device drivers can be separately coupled to other components of the system before a surgical procedure.

The surgical system 100, or a similar system in accordance with the described techniques, can be used to perform a surgical repair method involving reattachment of soft tissue to bone or attaching a graft tissue to bone. For example, the system can be used in reattaching a tendon (e.g., the supraspinatus tendon) to bone (e.g., the humeral head) in a rotator cuff repair procedure. The described techniques can also be used for other shoulder repair procedures, as well as for knee and other joint repair procedures requiring soft tissue attachment to associated bone.

The surgical repair method in accordance with the illustrated embodiments includes inserting a distal end of an elongate shaft into a bone. In one embodiment the shaft extends through an implantable, cannulated dilator feature and a suture anchor proximal to and, at least initially, spaced apart from the dilator feature. The elongate shaft has a capture suture extending through a lumen formed therethrough and exiting at an opening extending through a side of the shaft and disposed proximal to the dilator feature such that the capture suture forms a loop that extends through the opening and terminal end portions of the capture suture extend to a more proximal position on the shaft. The distal end of the elongate shaft with the dilator feature can be inserted into the bone until it reaches a depth sufficient to fully seat the suture anchor at the completion of the procedure.

The method also includes passing at least one retaining suture coupled to tissue through the capture suture loop, and closing the capture suture loop upon the retaining suture by applying and maintaining tension to the terminal end portions of the capture suture such that the capture suture causes the retaining suture to be brought closer to a sidewall of the shaft. In this way, the retaining suture is held against the elongate shaft in a manner that allows the suture anchor to subsequently engage the retaining suture and secure it (and thus the tissue coupled thereto) to bone.

In some embodiments, the retaining suture is passed through the capture suture and the capture suture's loop is closed or constricted prior to inserting the distal end of the elongate shaft into the bone. In such embodiments, the elongate shaft is inserted into the bone while tension is applied to terminal end portions of the capture suture to maintain the retaining suture(s) relative to the elongate shaft.

Regardless of whether the retaining suture is coupled to and engaged by the capture suture loop before or after the shaft is inserted into bone, the surgical method further involves driving the suture anchor distally towards the distal feature and into the bone and thereby secure the retaining suture between the bone and an outer surface of the suture anchor.

FIGS. 8A-8J illustrate a surgical repair method in accordance with the described embodiments. By way of example, the surgical repair method is illustrated using the surgical system 100 shown in FIGS. 1-7. It should be appreciated, however, that the surgical repair method can be performed using other surgical systems, including surgical systems in which one or more components can be different from those included in the surgical system 100.

Figure 8A:
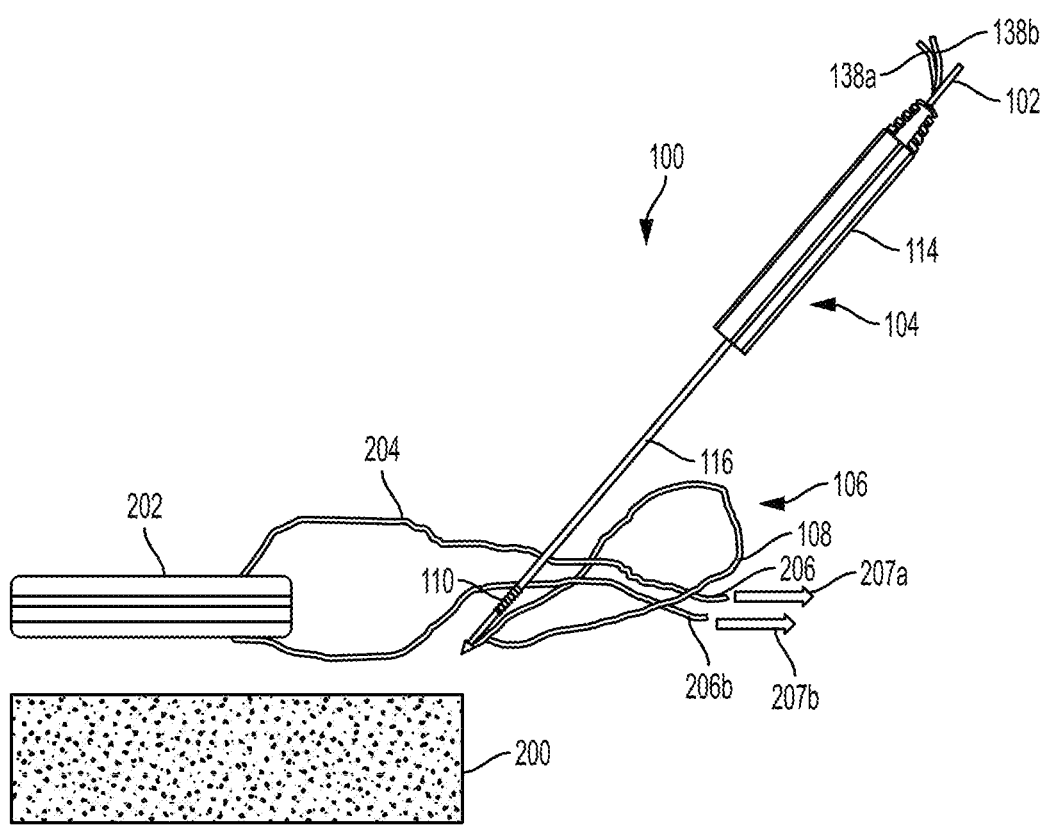
FIG. 8A illustrates the surgical system of FIG. 1, showing the surgical system near bone and showing a retaining suture passed through a loop formed by a capture suture.

FIG. 8A illustrates schematically bone 200 and soft tissue 202 (e.g., a tendon) that is to be reattached to the bone 200 using the surgical system 100. The elongate shaft 102 of the surgical system 100 has the capture suture 106 extending therethrough such that it forms the loop 108 extending through the opening 136. At least one retaining suture 204 is coupled to the tissue 202, such as by being passed through or wrapped around tissue 202. As shown in FIG. 8A, terminal end portions 206a, 206b of the retaining suture 204 are passed through the loop 108, as schematically shown by arrows 207a, 207b. It should be appreciated that the single retaining suture 204 is shown by way of example only, as multiple retaining sutures can be used to couple the tissue 202 to the bone 200. The relatively large size of the capture suture loop 108 and its adjustabity enable the use of multiple retaining sutures to join soft tissue to bone.

Figure 8B:
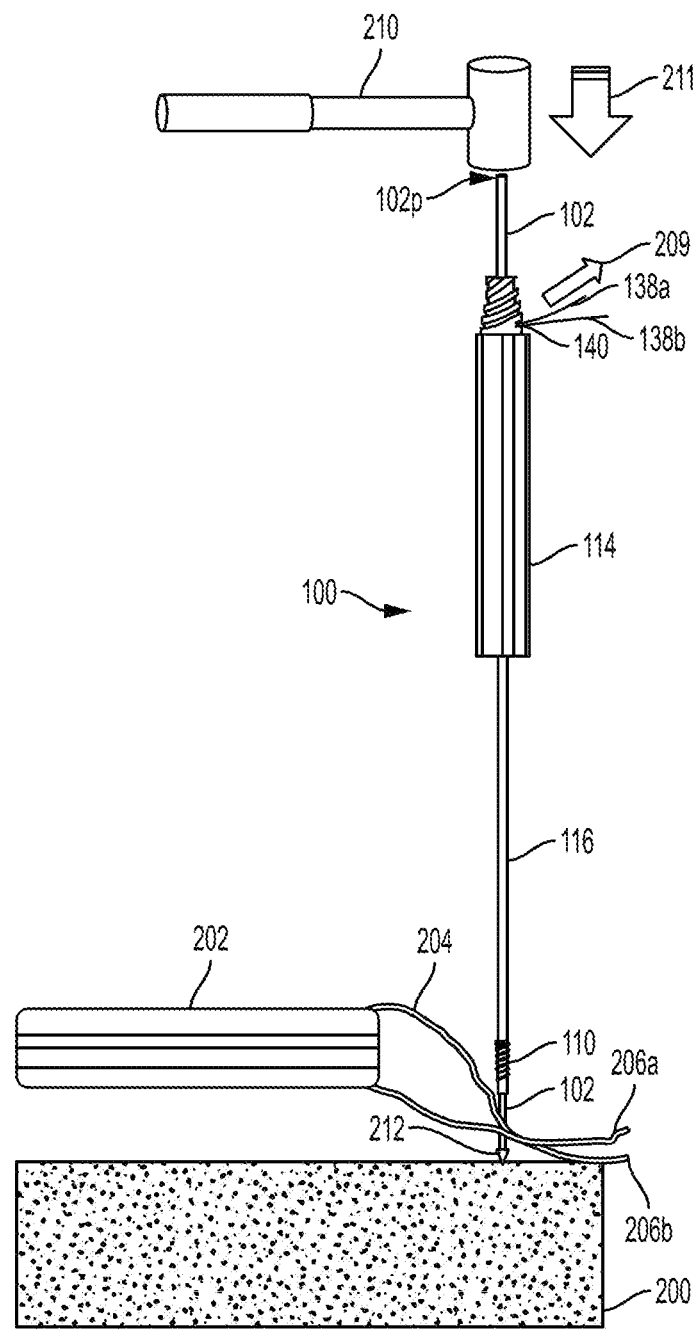
FIG. 8B illustrates the surgical system of FIG. 8A, showing a distal end of an elongate shaft initiating a hole in the bone.

After the retaining suture 204 is passed through the loop 108, the capture suture can be closed by applying tension to its terminal end portions 138a, 138b. As shown in FIG. 8B, the surgical system 100 includes the proximal end feature 140 configured to be non-removably or removably disposed at or near the proximal end of the shaft 102 such that the proximal end feature 140 is disposed proximal to the driver device's handle 114. The proximal end feature 140 has notches 141 or other retaining features formed thereon (e.g., grooves) configured to engage the terminal end portions of the capture suture. Thus, as shown in FIG. 8B, the terminal end portions 138a, 138b are wrapped around the proximal end feature 140 by engaging the notches 141, which facilitates maintaining tension on the terminal end portions of the capture suture 106 while pulling them away from the elongate shaft 102 (as shown schematically by an arrow 209) to close the capture suture loop 108. In this way, the retaining suture 204 is held against the elongate shaft 102 until the retaining suture 204 is wedged between the suture anchor 110 and bone, as described below. Among the advantages of the illustrated method is the ease with which the repair technique can be performed to securely reattach soft tissue to bone without the need to tie knots.

Figure 8C:
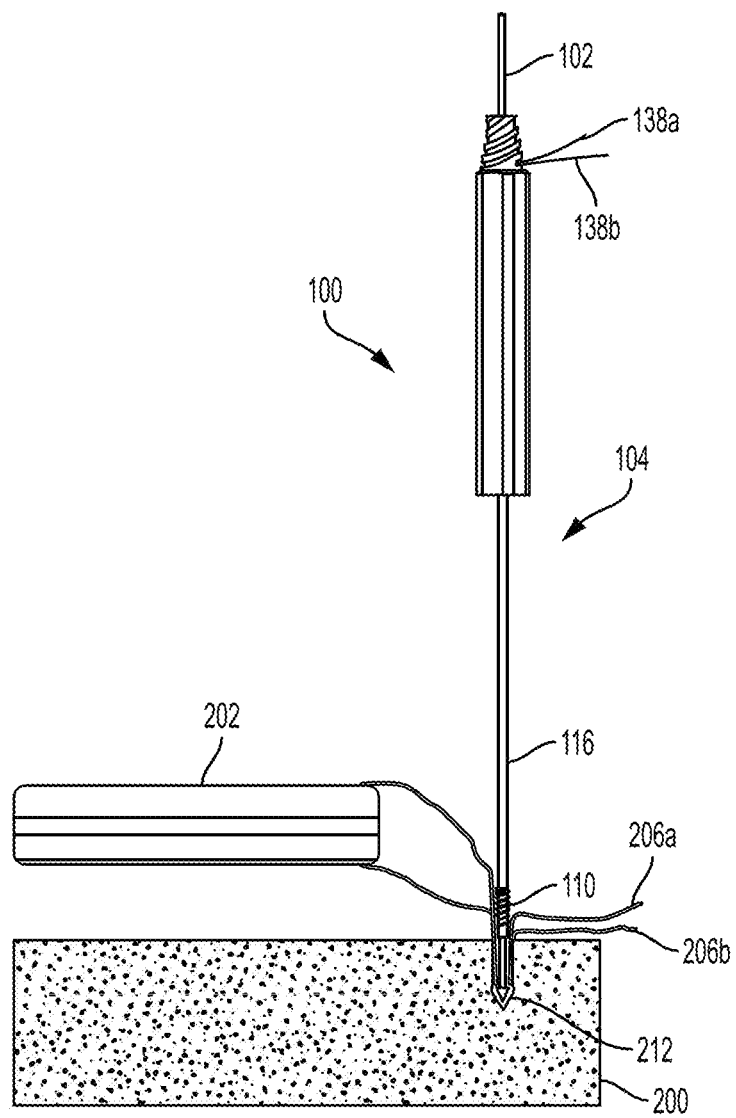
FIG. 8C illustrates the surgical system of FIG. 8B, showing the distal end of the elongate shaft driven distally into the bone.
Figure 8D:
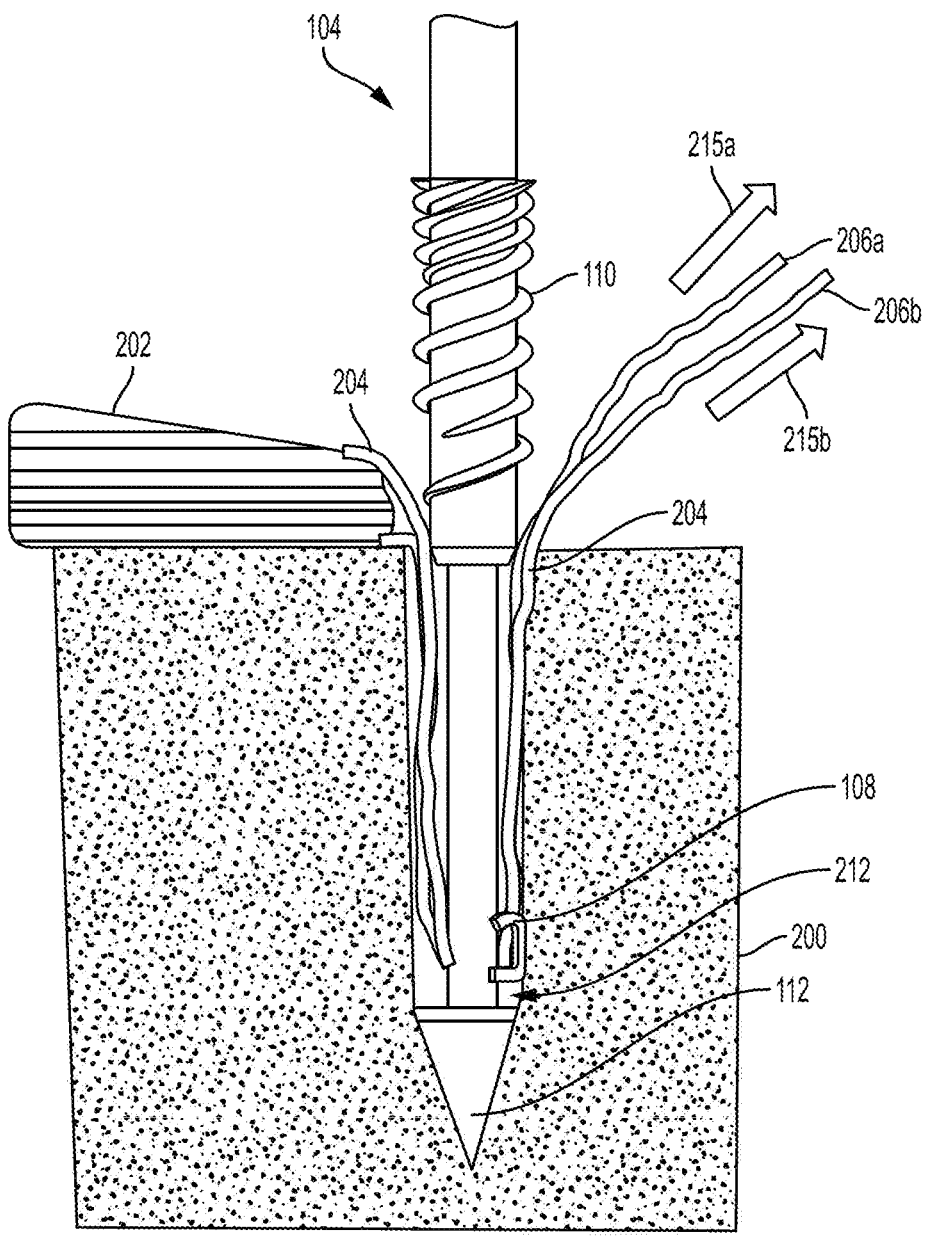
FIG. 8D illustrates the surgical system of FIG. 8C, showing a suture anchor near the bone.

While tension is maintained on the terminal end portions 138a, 138b of the capture suture 106, the distal end 102d of the elongate shaft 102 is inserted into the bone 200 to initiate a hole in the bone 200 at a desired location in the bone 200, as shown in FIG. 8B. In the illustrated embodiments, the elongate shaft 102 is a self-punching shaft configured to initiate the hole such that no additional instrument is required. FIG. 8B also illustrates that, once the bone hole is initiated, a suitable instrument 210, such as mallet, hammer, or other instrument, can be used to drive the elongate shaft 102 further distally into the bone 200. In this example, the instrument 210 can be used to apply force to the proximal end 102p of the elongate shaft 102 to drive the distal end 102d of the elongate shaft 102 into bone 200 to form a hole 212, as shown schematically by an arrow 211. The distal end 102d of the elongate shaft 102 can be driven into bone 200 such that the distal shaft portion 128 of the elongate shaft 102 with the dilator feature 112 coupled thereto is inserted into the hole 212 in the bone 200, as shown in FIGS. 8C and 8D. A portion of the central shaft portion 126 of the elongate shaft 102 is also inserted into the hole 212, whereas the suture anchor 110 is positioned at a desired position relative to the bone hole 212. In the illustrated embodiment, as shown in FIG. 8D, before being driven into the bone, the suture anchor 110 is disposed just proximal to the bone hole 212. In other embodiments, the suture anchor 110 can be disposed differently with respect to the hole 212—for example, the suture anchor 110 can be at least partially inserted into the bone hole.

As shown in FIG. 8D, the terminal end portions 206a, 206b of the retaining suture 204 are disposed outside the bone hole 212, and tension applied thereto ensures that the suture 204 is positioned and temporarily held in the bone hole 212 in a taut state, as shown schematically by arrows 215a, 215b in FIG. 8D. The tension applied to the terminal end portions 206a 206b of the retaining suture 204 can cause the tissue 202 to be positioned as desired with respect to the bone hole 212. For example, in the illustrated embodiment, the tissue 202 can be moved closer to the bone hole 212, as shown in FIG. 8D where the tissue 202 is closer to the bone hole 212 than the tissue 202 as shown in FIG. 8C.

Figure 8E:
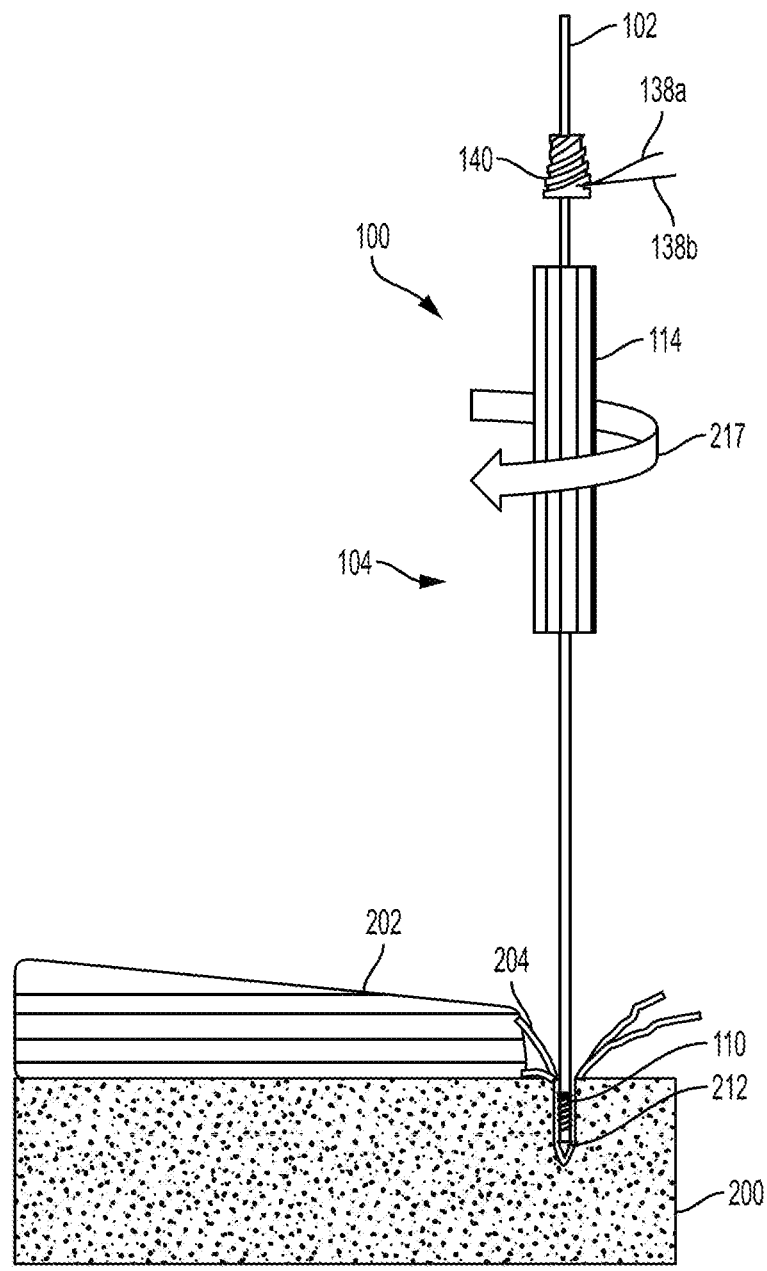
FIG. 8E illustrates the surgical system of FIG. 8D, showing a driver device rotated.
Figure 8F:
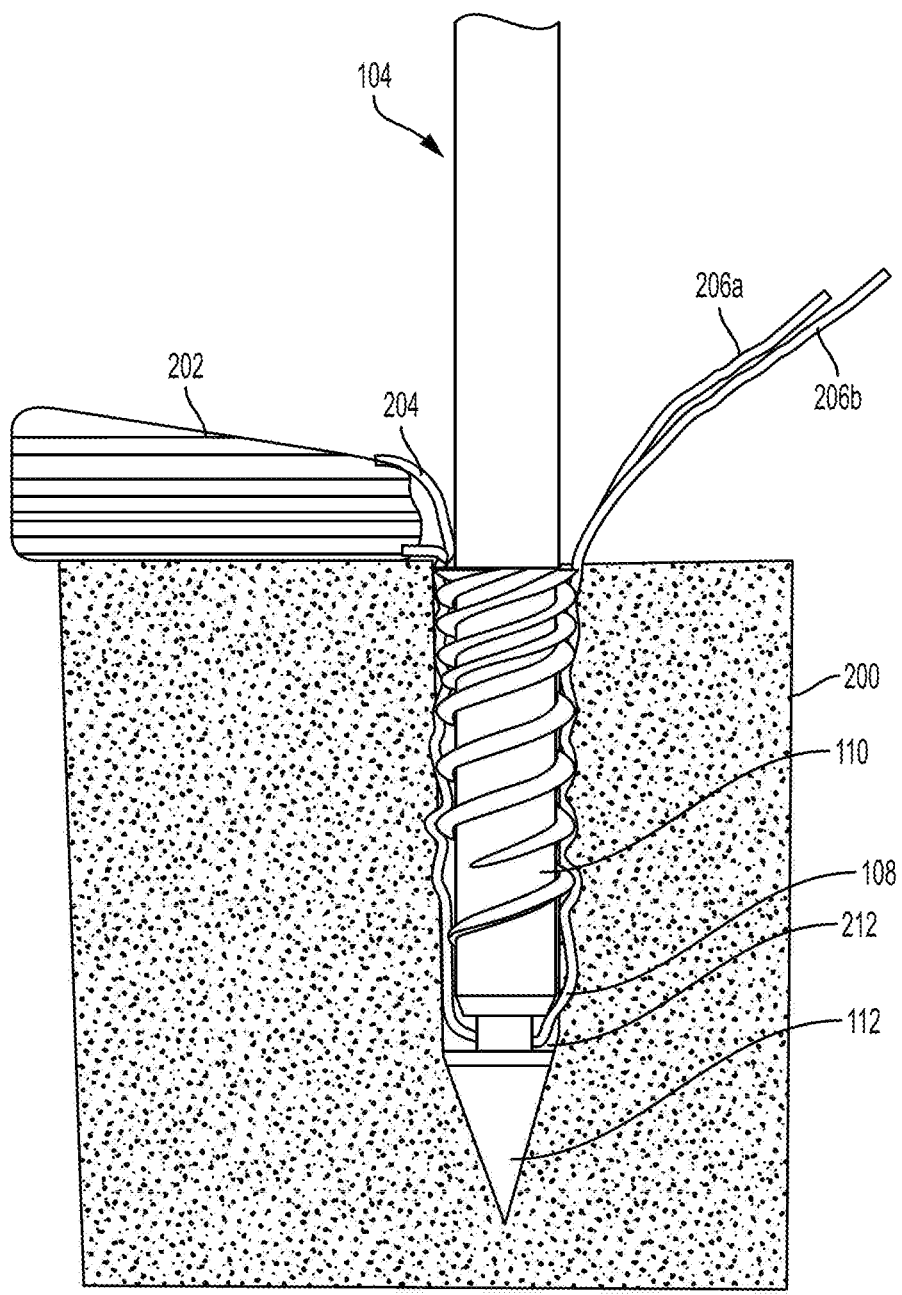
FIG. 8F illustrates the surgical system of FIG. 8E, showing the suture anchor driven into the bone.

Once the elongate shaft 102 with the dilator feature 112 is inserted into the bone 200 so as to form the bone hole 212 in the desired location, the suture anchor 110 can be driven distally towards the dilator feature 112 and into the bone hole 212 and thereby secure the retaining suture 204 between the inner surface of the bone hole 212 and an outer surface of the suture anchor 110, as shown in FIGS. 8E and 8F. In the illustrated embodiment, the driver device 104, having its distal driver member 120 releasably coupled to the suture anchor 110, is operated to drive the suture anchor 110 into the bone hole 212. For example, the driver device 104 can be rotated, as schematically shown by an arrow 217 in FIG. 8E, to cause the suture anchor 110 coupled thereto to advance distally into bone as the threads 111 of the suture anchor 110 engage an interior wall of the bone hole 212. As the driver device 104 is rotated, the elongate shaft 102, which extends through the lumen 122 of the driver device 104, remains stationary. Thus, as shown in FIG. 8E, after the device driver 104 has been driven distally, the proximal handle 114 of the driver device 104 is disposed offset from and more distal with respect to the proximal end feature 140 coupled to the proximal end of the elongate shaft 102. The driver device 104 is rotated to thereby cause the suture anchor 110 to move distally towards the distal feature 112 and into the bone 200, which causes the retaining suture 204 to be retained between the side wall of the suture anchor 110 and the bone hole 212.

Figure 8G:
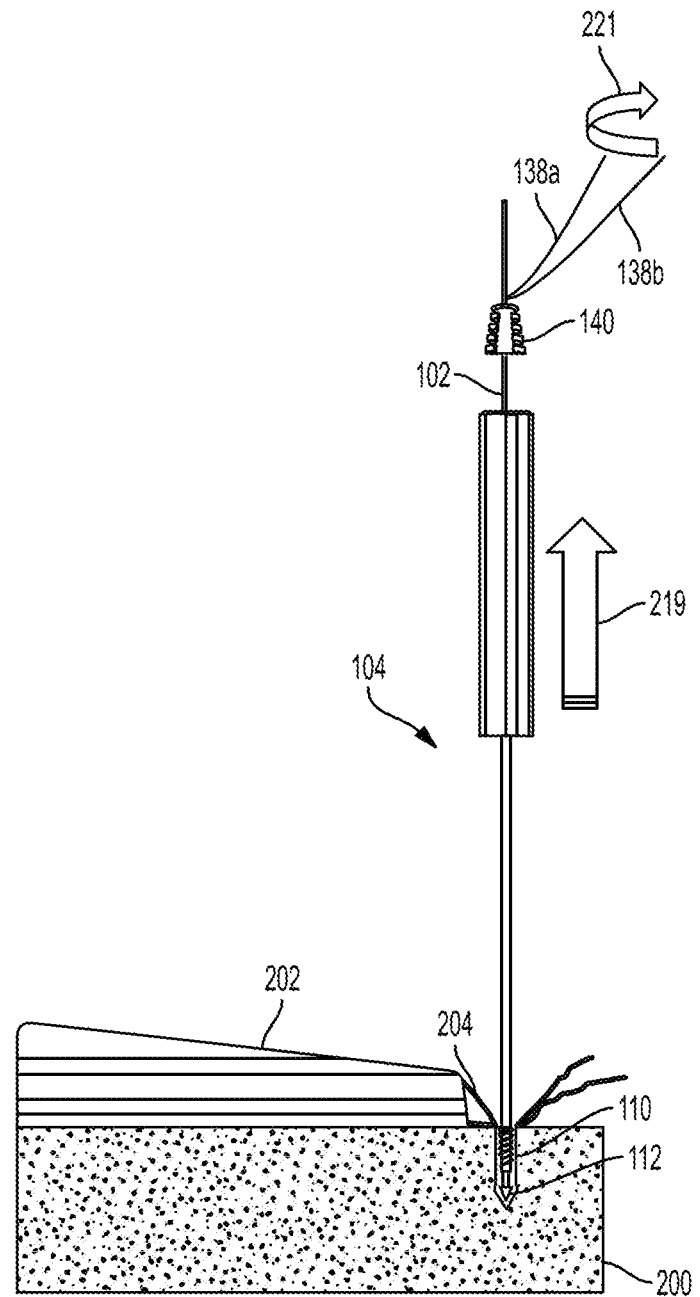
FIG. 8G illustrates the surgical system of FIG. 8F, showing the driver device and the elongate shaft being removed.
Figure 8H:
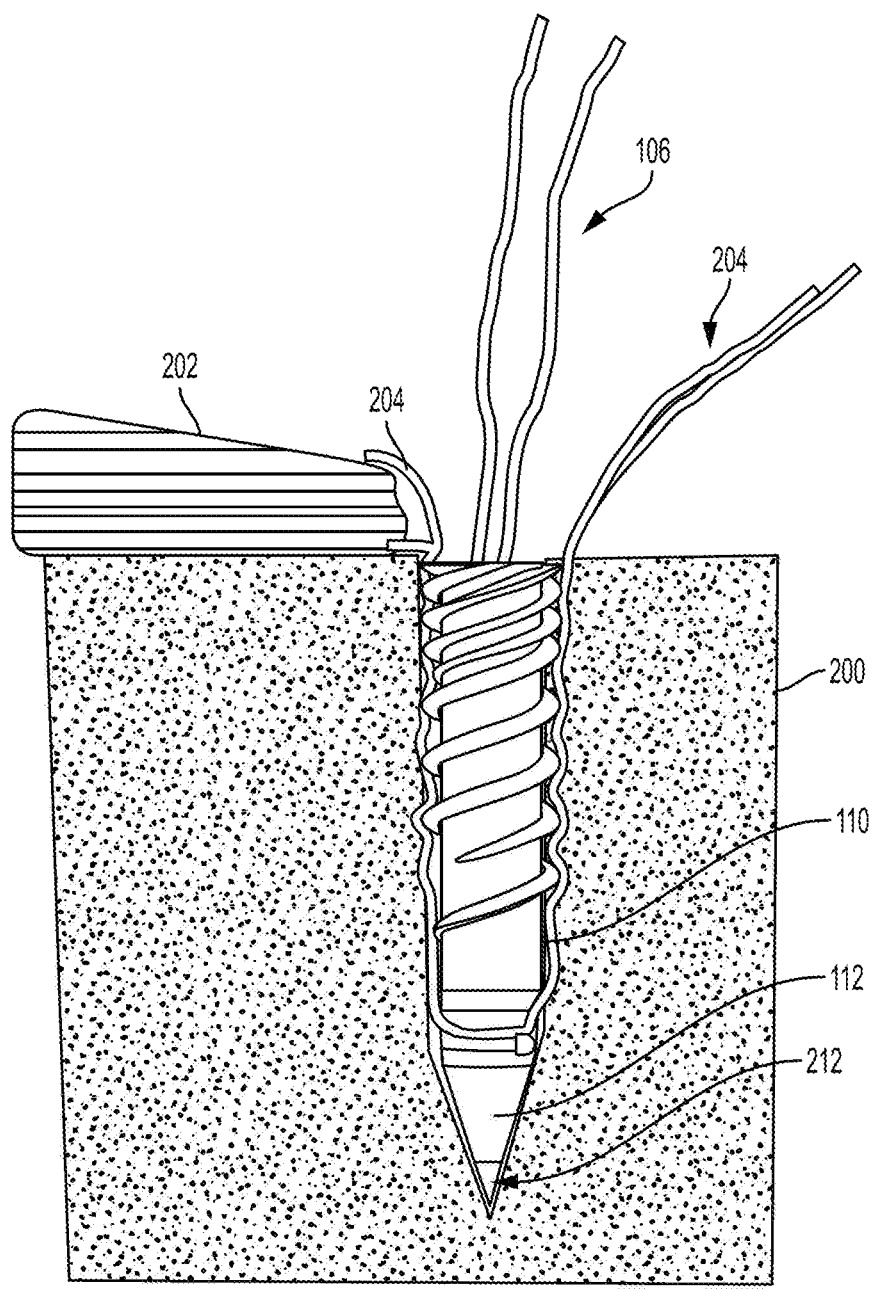
FIG. 8H illustrates the surgical system of FIG. 8G, showing the retaining suture secured.

Once the suture anchor 110 has been driven into the hole 212 in the bone 200, the elongate shaft 102 can be separated from the dilator feature 112, and the driver device 104 can be separated from the suture anchor 110, as shown schematically by an arrow 219 in FIG. 8G. In some embodiments, the elongate shaft 102 may not be coupled to the driver device 104, and the elongate shaft 102 may be separated from the dilator feature 112 and removed from the lumen 122 of the driver device 104 before the driver device 104 is separated from the suture anchor 110. In other embodiments, the elongate shaft 102 and the driver device 104 can be coupled to one another, and they can be separated from the dilator feature 112 and the suture anchor 110 substantially simultaneously. Regardless of the manner in which the elongate shaft 102 and the driver device 104 are removed, the dilator feature 112 and the suture anchor 110 remain implanted in the bone hole 212, as shown in FIGS. 8G and 8H. As shown in FIG. 8G, the terminal end portions 138a, 138b of the capture suture 106, which are coupled to the proximal end feature 140 which helps tension the suture 206, can be unwrapped from the proximal end feature 140 and thereby become separated from the proximal end feature 140.

Figure 9A:
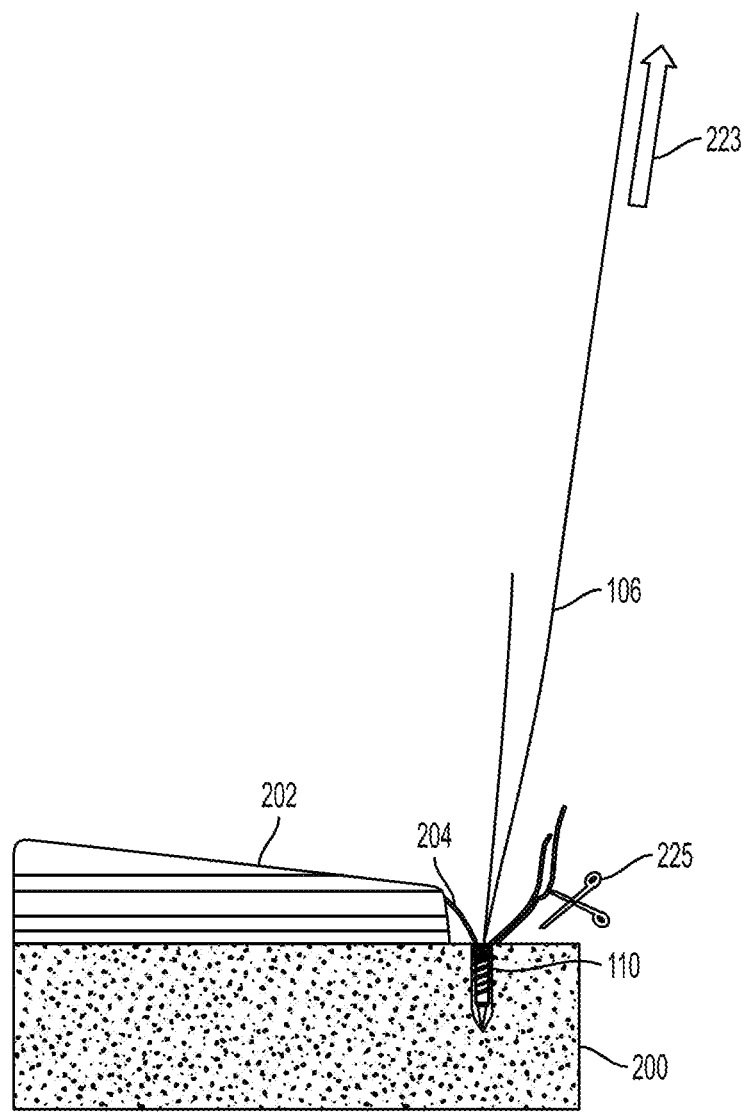
FIG. 9A illustrates the surgical system of FIG. 8H, showing the capture suture being removed.
Figure 9B:
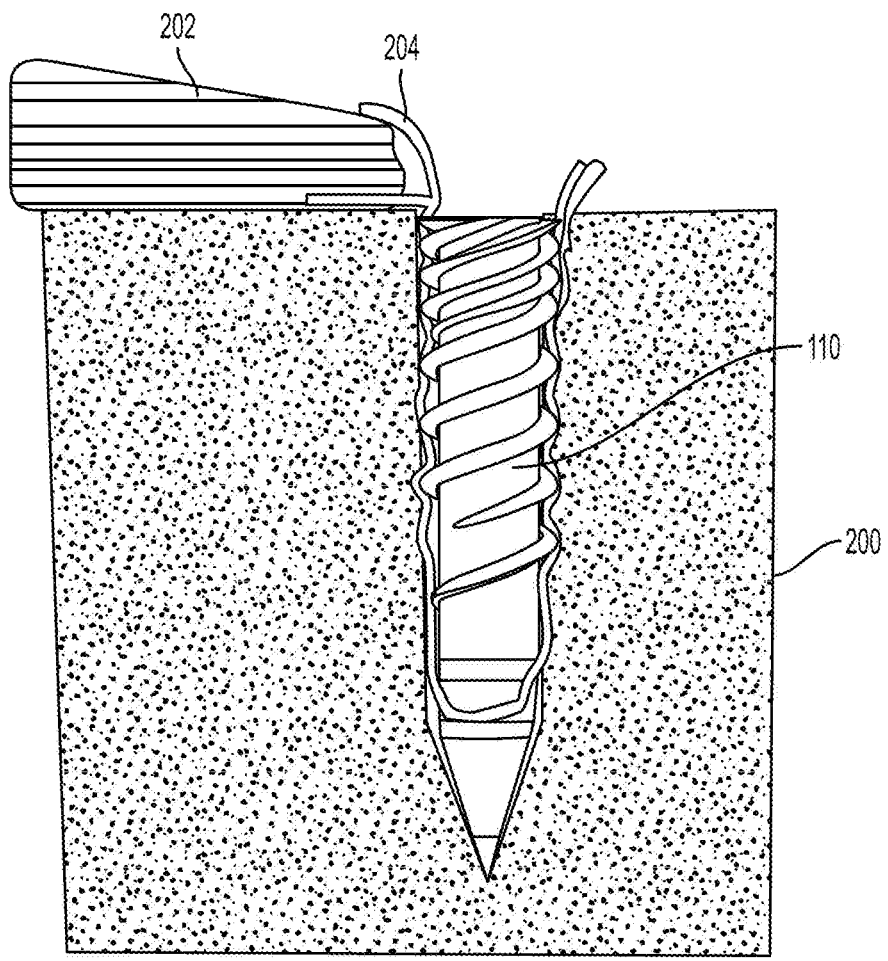
FIG. 9B illustrates the surgical system of FIG. 9A, showing the retaining suture trimmed.

FIG. 8H shows the dilator feature 112 and the suture anchor 110 implanted in the bone hole 212. After the elongate shaft 102 and the driver device 104 are removed, the capture suture 106 can remain associated with the suture anchor 110, as shown in FIG. 8H. In some embodiments, after the suture anchor 110 has been driven into the bone 200, and prior to, simultaneously with, or after the elongate shaft 102 and the driver device 104 are removed, the capture suture 106 can be removed, as shown schematically by an arrow 223 in FIG. 9A. The terminal end portions 206a, 206b of the retaining suture 204 can be trimmed, e.g., by using a cutting device (shown schematically as scissors 225). As a result, the suture anchor 110, without the capture suture 106 coupled thereto, secures the retaining suture 204 to the bone 200 thereby securing the tissue 202 to the bone 200, as shown in FIG. 9B. The terminal end portions 206a, 206b of the retaining suture 204 can be trimmed, as also shown in FIG. 9B.

In the embodiments described above, the elongate shaft of the surgical system is inserted into bone after the retaining suture has been coupled to the capture suture loop and after the loop has been closed to hold the retaining suture relative to the shaft. In other embodiments, however, as discussed above, the elongate shaft having the capture suture coupled thereto can first be inserted into the bone, and one or more retaining sutures can then be passed through the capture suture loop and the loop is tightened or closed to thereby bring the retaining suture(s) towards and against the elongate shaft. Regardless of which of the above approaches are used, once the elongate shaft of the surgical system is driven into the bone to form a bone hole and the capture suture loop is closed over the retaining suture(s) passed therethrough, the suture anchor is driven distally into the bone hole. Once positioned properly in the bone hole, the suture anchor secures the retaining suture in the bone, thereby securing the tissue coupled to the retaining suture to the bone.

In some embodiments, a surgical system can include a driver device or driver, an elongate shaft, a suture anchor having external threads formed thereon, and a dilator feature distal to the suture anchor. The driver can have a proximal handle and a driver shaft extending therefrom, the driver shaft having a distal driver feature and a lumen extending therethrough, the driver having an opening extending through a side thereof. The elongate shaft is receivable in the lumen of the driver such that a distal portion of the elongate shaft extends distally from the distal driver feature, a central shaft portion of the elongate shaft having a suture retaining feature extending therethrough that communicates with the opening of the driver. The suture anchor can have a lumen extending therethrough that removably receives the central shaft portion therein, wherein the distal driver feature is operably coupled to the suture anchor. The dilator feature distal can have the distal portion of the elongate shaft at least partially extending therethrough such that at least a portion of a distal tip of the elongate shaft extends distally from a distal end of the dilator feature.

Figure 10:
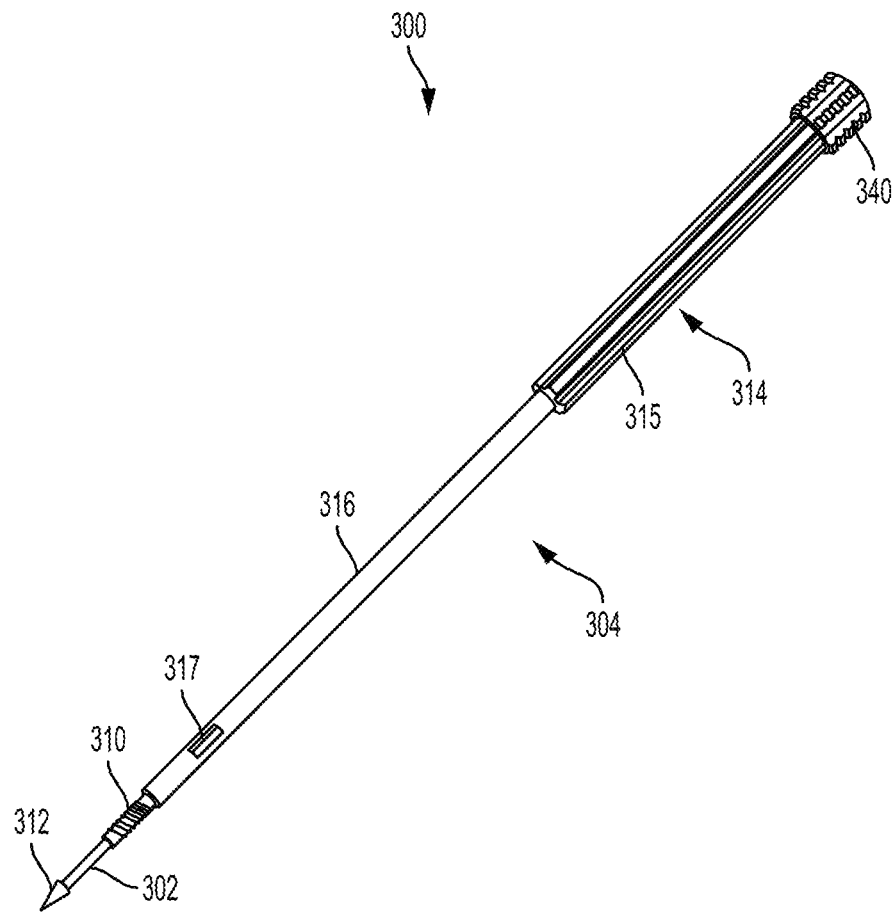
FIG. 10 is a perspective view of another embodiment of a surgical system.

FIGS. 10-15I illustrate another embodiment of a surgical system 300 that includes an elongate shaft 302, a driver 304 that receives the elongate shaft 302 therethrough, a suture anchor 310, and a dilator feature 312 that can be implantable. In the illustrated embodiment, the driver 304 can have a proximal handle 314. The elongate shaft 302 also has a handle 340 coupled to a proximal end thereof. As shown in FIG. 10, the handle 340 of the elongate shaft 302 is disposed proximally to the proximal handle 314 of the driver 304. The handle 340 of the elongate shaft 302 and the proximal handle 314 of the driver 304 can be independently movable, as discussed in more detail below.

Figure 11:
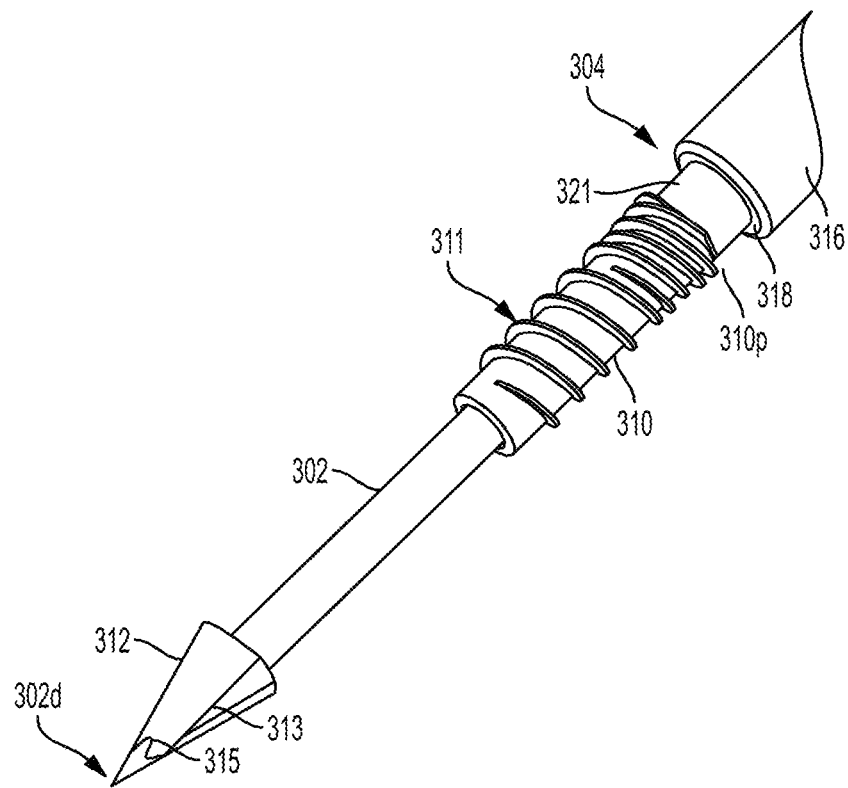
FIG. 11 is a perspective view of a distal portion of the surgical system of FIG. 10.
Figure 13:
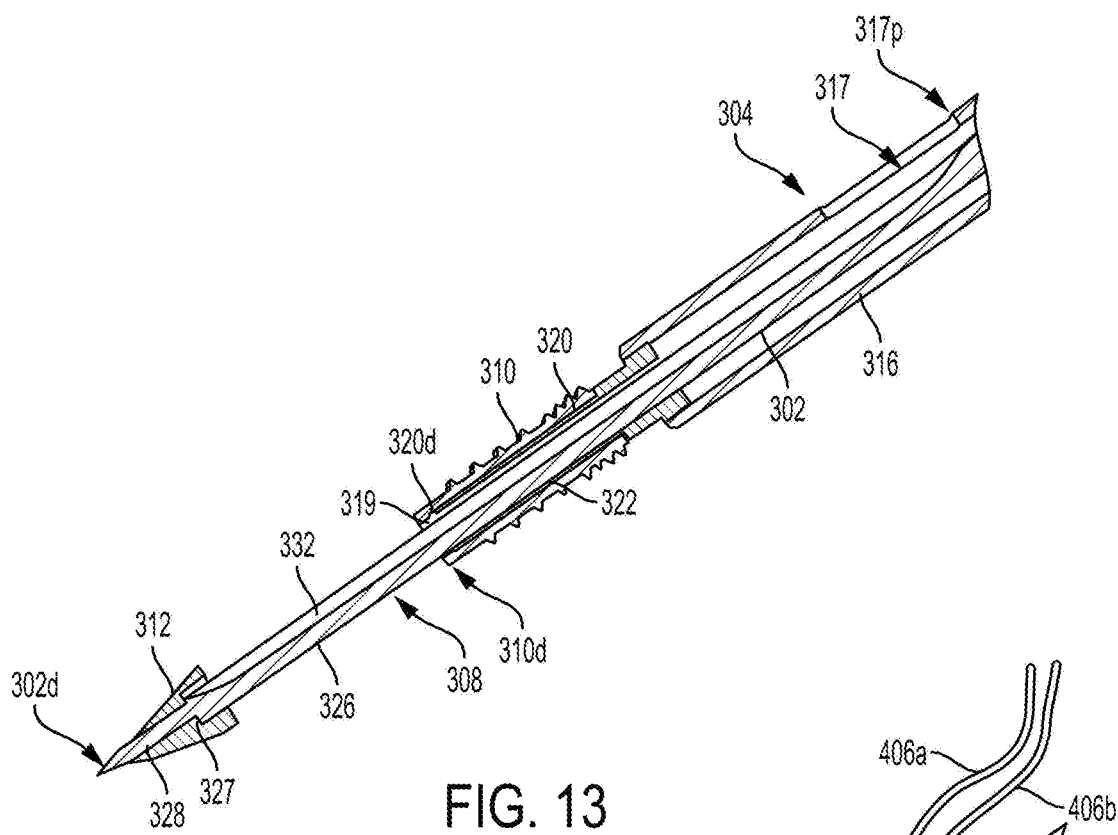
FIG. 13 is a perspective, partially cross-sectional view of a portion of the surgical system of FIG. 10.
Figure 14:
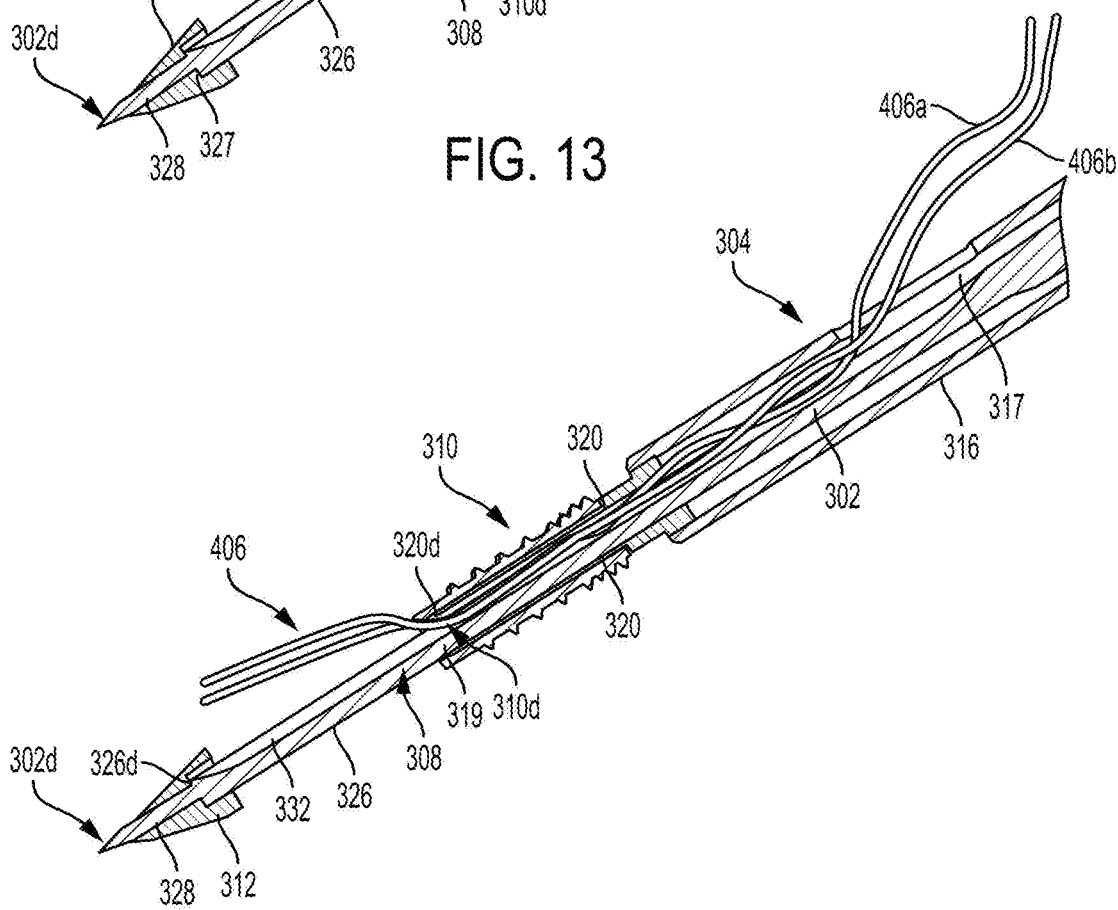
FIG. 14 is a perspective, partially cross-sectional view of the portion of the surgical system of FIG. 13, showing a suture coupled thereto.

The components of the system 300 can have various configurations. As shown in FIG. 10, the driver device 304 that is configured to drive the suture anchor 310 into bone has the proximal handle 314 and a driver shaft 316 extending therefrom. The driver shaft 316 can be coupled to the handle 314 in various ways. As shown in FIG. 11, the driver shaft 316 has a shoulder 318 proximal to a distal driver member 320 that extends from the shoulder 318 to a distal end 320d of the distal driver member 320, which is also a distal end of the driver shaft 316 of the driver device 304. The distal driver member 320 has the suture anchor 310 mounted thereon, as shown in FIGS. 13 and 14. In the illustrated embodiment, the driver shaft 316 has a neck feature 321 configured to seat between the shoulder 318 and the distal driver member 320 such that the neck feature 321 abuts a proximal end 310p of the suture anchor 310. In use, the neck feature 321 facilitates driving the suture anchor 310 distally. It should be appreciated that the driver shaft 316 can have other suitable configurations, including the configurations in which the shoulder 318 and/or the neck feature 321 are not included.

Figure 12:
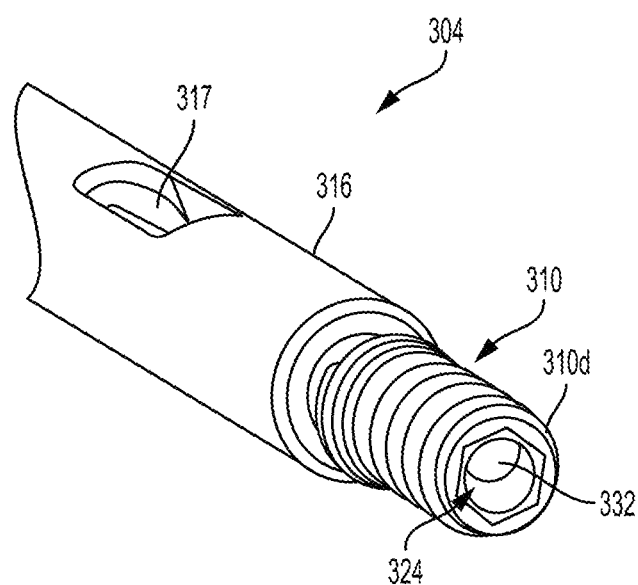
FIG. 12 is a perspective, partially cross-sectional view of a portion of the surgical system of FIG. 10.

The driver shaft 316 has a lumen 322 extending therethrough, as shown in FIGS. 12-14. The lumen 322 of the driver shaft 316 receives the elongate shaft 302 therethrough. Further, in the illustrated embodiment, the driver shaft 316 of the driver device 304 has an opening 317 extending through a side thereof, as shown in FIGS. 10 and 12-14.

The proximal handle 314 of the driver device 304 can have a variety of configurations. In the illustrated embodiment, the lumen 322 of the driver device 304 extends through the driver shaft 316 as well as through a length of the proximal handle 314. In this way, the lumen 322 of the driver device 304 receives the elongate shaft 302 therethrough. The driver shaft 316 is coupled to the proximal handle 314 in a suitable manner, such that rotation of the proximal handle 314 causes the driver shaft 316 to be rotated. The proximal handle 314 of the driver device 304 can be configured to have surface features that facilitate grip during use of the driver device 304. For example, as shown in FIG. 10, the proximal handle 314 can have one or more grooves 315 formed along its length. It should be appreciated, however, that the proximal handle 314 can have any suitable features, as the described embodiments are not limited in this respect.

The suture anchor 310 can have various configurations. In the illustrated embodiment, the suture anchor 310 has external threads 311 formed thereon configured to engage the suture anchor 310 with the bone. The threads 311 can be in the form of one or more threads. The suture anchor 310 can have any suitable configuration and can have other bone-engaging features. As shown in FIGS. 12-14, the suture anchor 310 can have a lumen 324 extending therethrough such that at least in a portion of the lumen 324 can receive therein the distal driver member 320. In an assembled configuration, as shown in FIGS. 13 and 14, the distal driver member 320 extends through the lumen 324 of the suture anchor 310 such that the distal end 320d of the distal driver member 320 is disposed proximal to a distal end 310d of the suture anchor 310. However, in other embodiments, the distal end 320d of the distal driver member 320 can be aligned with or can extend beyond the distal end 310d of the suture anchor 310.

The distal driver member 320 of the driver device 304 is configured to releasably mate with the suture anchor 310 and to thereby drive the suture anchor 310 mated thereto distally into bone, as discussed in more detail below. In some embodiments, as illustrated herein, the distal driver member 320 can be in the form of a male feature configured to be received within a corresponding female drive feature formed on at least a portion of an interior wall defining the lumen of the suture anchor 310.

In the illustrated embodiment, as shown in FIG. 12, the male feature is hexagonal-shaped, and the corresponding female drive feature of the suture anchor 310 can be a corresponding hexagonal-shaped female drive feature formed in at least a portion of an interior wall defining the lumen 324 of the suture anchor 310. FIG. 12 shows that at least a portion of the interior wall defining the lumen 324 of the suture anchor 310 is hexagonal in cross-section. In the illustrated embodiment, a distal portion 319 (FIGS. 13 and 14) of an interior wall defining the lumen 324 may not have a female feature (e.g., a hexagonal-shaped female feature), configured to mate with the distal driver member 320, formed therein. In this embodiment, the distal driver member 320 of the driver device 304 extends through the lumen 324 of the suture anchor 310 such that the distal end 320d of the distal driver member 320 is disposed proximal to the distal end 310d of the suture anchor 310. The distal portion 319 of the interior wall defining the lumen 324 of the suture anchor 310 can be circular in cross-section, which facilitates passage of a suture through a distal end of the lumen 324 of the suture anchor 310.

In the illustrated embodiment, as shown in FIGS. 13 and 14, the elongate shaft 302 has a central shaft portion 326 and a distal shaft portion 328 extending distally from a distal shoulder 327 and terminating at the distal end 302d of the elongate shaft 302. However, it should be appreciated that in other embodiments, the distal shoulder 327 may not be formed. The distal shaft portion 328 includes a distal awl tip portion 330, which is distally tapered. In the illustrated embodiment, the distal shaft portion 328 can have an outer diameter that is less than an outer diameter of the central shaft portion 326.

In an assembled configuration, the elongate shaft 302 can be received within the lumen 322 of the driver device 304 such that a distal shaft portion 328 of the elongate shaft 302 and at least a part of the central shaft portion 326 of the elongate shaft 302 extend distally from the distal driver member 320. The elongate shaft 302 can be removable from the lumen 322 of the driver device 304. In the illustrated embodiments, the distal end 302d of the elongate shaft 302 is configured to be inserted into bone to initiate a hole in the bone. Thus, there is no need to initiate a hole in the bone using other instruments.

In the illustrated embodiment, as shown in FIGS. 12-14, the central shaft portion 326 of the elongate shaft 302 has a suture retaining feature 332 extending therethrough that is configured to seat at least one suture. As shown in FIGS. 13 and 14, the suture retaining feature 332 can extend from a distal end 326d of the central shaft portion 326. In this example, the distal end 326d of the central shaft portion 326 coincides with the distal shoulder 327 of the central shaft portion 326, though the central shaft portion 326 may not have such a distal shoulder. The suture retaining feature 332 can extend to a termination at the central shaft portion 336 such that the suture retaining feature 332 communicates with the opening 317 extending through the side of the driver device 304. In the illustrated embodiment, as shown in FIGS. 13 and 14, the suture retaining feature 332 terminates approximately at a proximal end 317p of the opening 317 of the driver device 304. However, in other embodiments, the suture retaining feature 332 can terminate distally or proximally to the proximal end 317p of the opening 317.

The suture retaining feature 332 of the central shaft portion 326 of the elongate shaft 302 can have any suitable configuration and can be formed in any suitable manner in the elongate shaft 302 so as to seat at least one suture therealong. In the illustrated embodiment, the suture retaining feature 332 can be in the form of a groove formed along or parallel to a longitudinal axis of the elongate shaft 302 in an outer surface of the central shaft portion 326. However, in other embodiments, the suture retaining feature 332 can be in the form of a lumen or other feature.

In the illustrated embodiment, the surgical system 300 includes the dilator feature 312 that is distal to the suture anchor 310. The distal shaft portion 328 of the elongate shaft 302 is configured to extend through the dilator feature 312 such that the distal end 302d of the elongate shaft 302 extends distally from the dilator feature 312. The dilator feature 312 is configured to facilitate insertion of the elongate shaft 302 into bone by widening a hole in bone once the hole is initiated, such as by the distal end 302d of the elongate shaft 302. The dilator feature 312 is distally tapered. As shown in FIG. 11, the dilator feature 312 can be in the form of a truncated pyramid shape with two or more triangular faces 313. The faces 313 can be substantially flat, or they can be configured otherwise. In the illustrated embodiment, the dilator feature 312 has three faces 313, with each of the faces 313 having a groove 315 at a distal end of the face. Such a shape of the dilator feature 312 may facilitate its insertion into bone. It should be appreciated that the dilator feature 312 can have two or more than three faces. Also, in other embodiments, the dilator feature 312 can be in form of a truncated cone, though the dilator feature 312 can have other suitable configurations.

The dilator feature 312 can be press-fit onto or otherwise releasably coupled with the elongate shaft 302. The dilator feature 312 can be in the form of a three-faced trocar point, as in the illustrated embodiment. However, in some embodiments, the dilator feature 312 can lack surface features, or have one or more surface features that facilitate its engagement with the bone. The dilator feature 312 can have any suitable dimensions. Furthermore, in some embodiments, the dilator feature 312 can be implantable and it can be made from a non-metallic material. This can be beneficial since the properties of non-metallic materials are such that they would not interfere with post-implantation imaging of the repair done using system 300. Moreover, while it is sufficiently rigid to assist in forming a bone hole, the dilator feature 312 can be bioabsorbable and/or biodegradable. However, in other embodiments, the dilator feature 312 can be made from a metal.

In the illustrated embodiment, as shown in FIG. 14, the surgical system 300 can have at least one suture 406 associated therewith that is used to attach tissue to bone. The suture 406 can be retained by the surgical system 300 such that terminal end portions 406a, 406b of the suture 406, which can be coupled to issue, are passed through the lumen 324 of the suture anchor 310, along the suture retaining feature 332 of the central shaft portion 326 of the elongate shaft 302, and through the opening 317 extending through the side of the driver device 304. As shown in FIG. 14, the terminal end portions 406a, 406b of the suture 406 extend out of the opening 317.

FIGS. 15A-15J illustrate the surgical system 300 used for a surgical repair method to attach soft tissue 402 (e.g., tendon) to bone 400. It should be appreciated that the surgical repair method in accordance with the described embodiments can be performed using other surgical systems, including surgical systems in which one or more components can be different from those included in the surgical system 300.

Figure 15A:
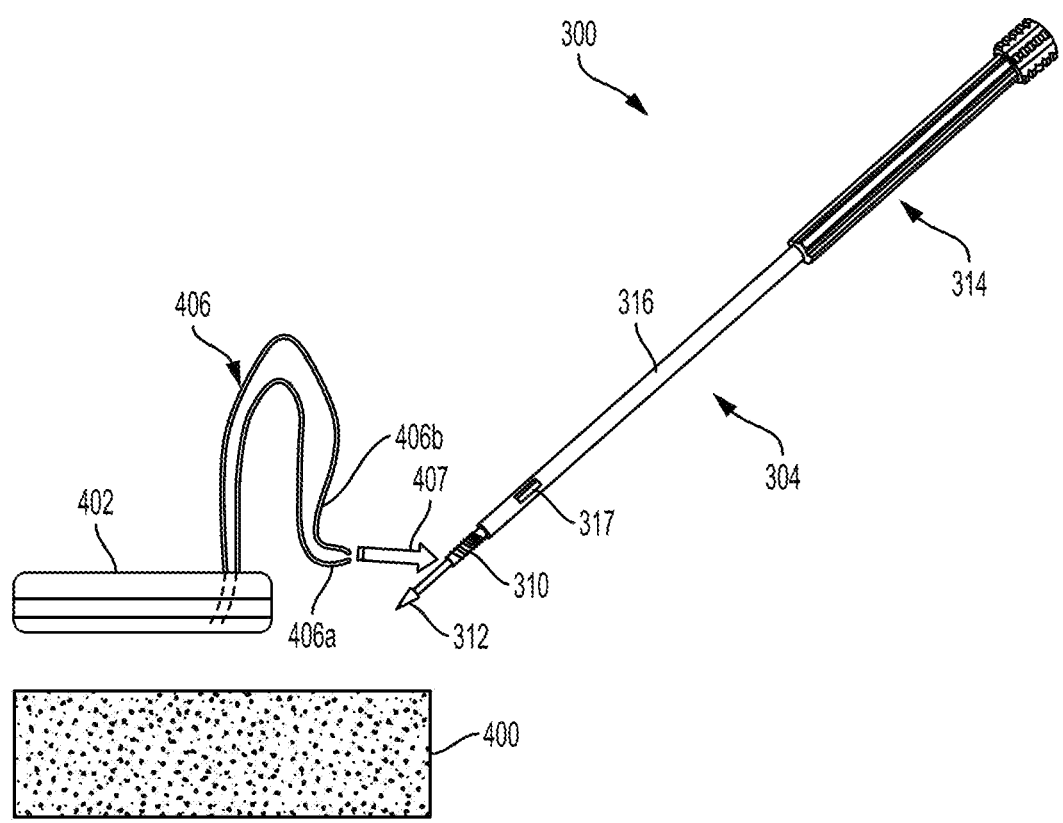
FIG. 15A illustrates the surgical system of FIG. 10, showing the surgical system near bone.

FIG. 15A illustrates schematically (arrow 407) that the terminal end portions 406a, 406b of the suture 406 are coupled to the system 300. As discussed above, the terminal end portions 406a, 406b of the suture 406 can be passed through the lumen 324 of the suture anchor 310, along the suture retaining feature 332 of the central shaft portion 326 of the elongate shaft 302, and through the opening 317 extending through the side of the driver device 304, as shown in FIG. 14. FIG. 15A illustrates that the suture 406 can be coupled to the tissue 402. For example, the suture 406 can be passed through or otherwise coupled to the tissue 402 such that the terminal end portions 406a, 406b of the suture 406 are free to engage with the system 300.

Figure 15B:
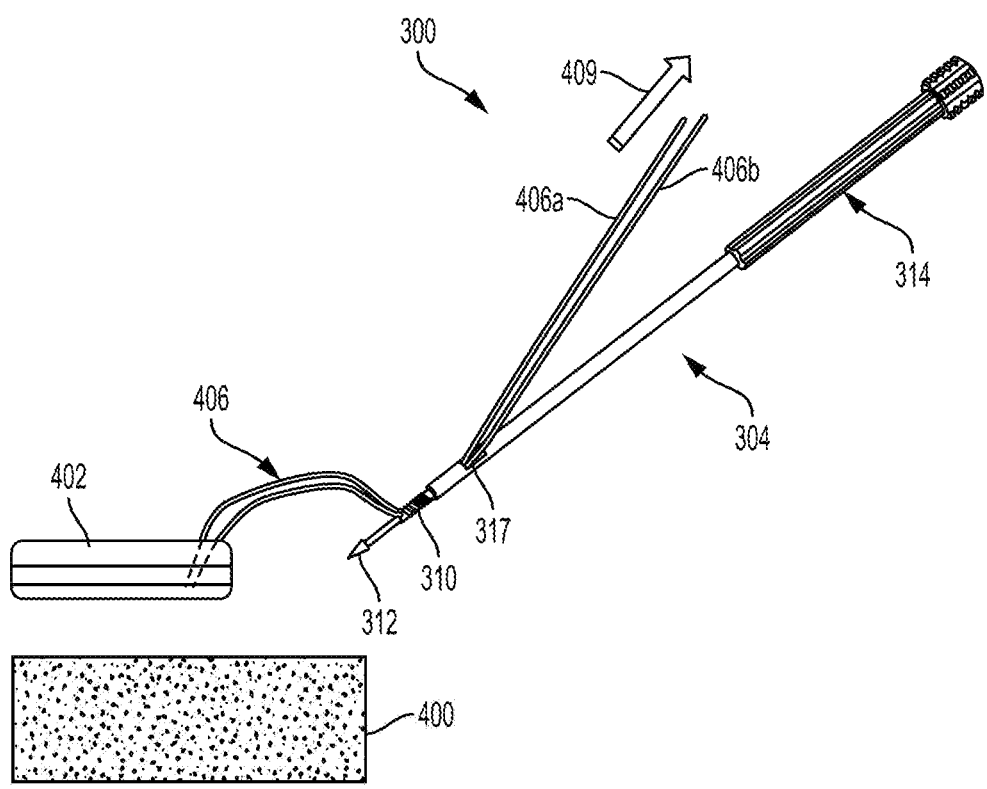
FIG. 15B illustrates the surgical system of FIG. 15A, showing a suture coupled thereto.
Figure 15C:
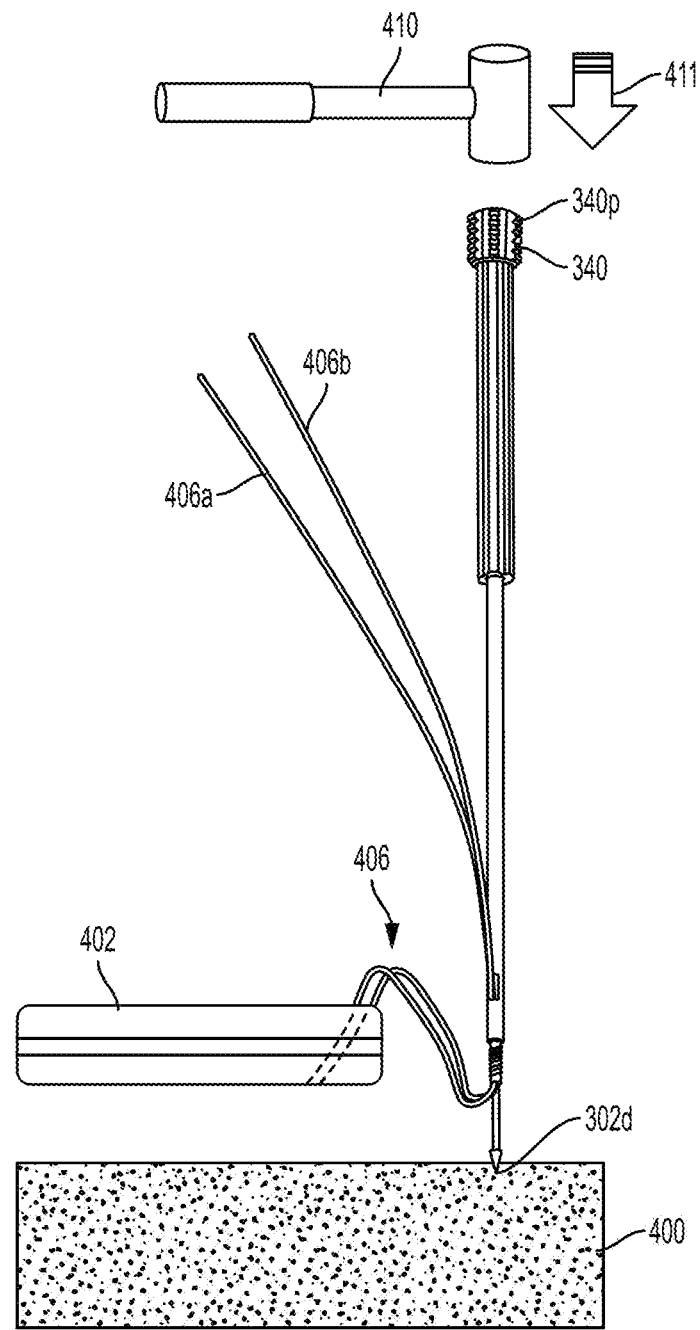
FIG. 15C illustrates the surgical system of FIG. 15B, showing a distal end of an elongate shaft initiating a hole in the bone.

FIG. 15B illustrates the surgical system 300 with the suture 406 loaded thereon. Tension can be applied to the suture 406, as shown by an arrow 409. While tension is maintained on the terminal end portions 406a, 406b of the suture 406, the distal end 302d of the elongate shaft 302 is inserted into the bone 400 to initiate a hole in the bone 400 at a desired location in the bone 400, as shown in FIG. 15C. In the illustrated embodiment, the elongate shaft 302 is a self-punching shaft configured to initiate the hole such that no additional instrument is required. FIG. 15C also illustrates that, once the hole in the bone is initiated, a suitable instrument 410, such as mallet, hammer, or other instrument, is used to drive the elongate shaft 302 further distally into the bone 400. In this example, the instrument 410 can be used to apply force to a proximal end 340p of the proximal handle 340 coupled proximally to the elongate shaft 302 to thereby drive the distal end 302d of the elongate shaft 302 further into the bone 400, as shown by an arrow 411.

Figure 15D:
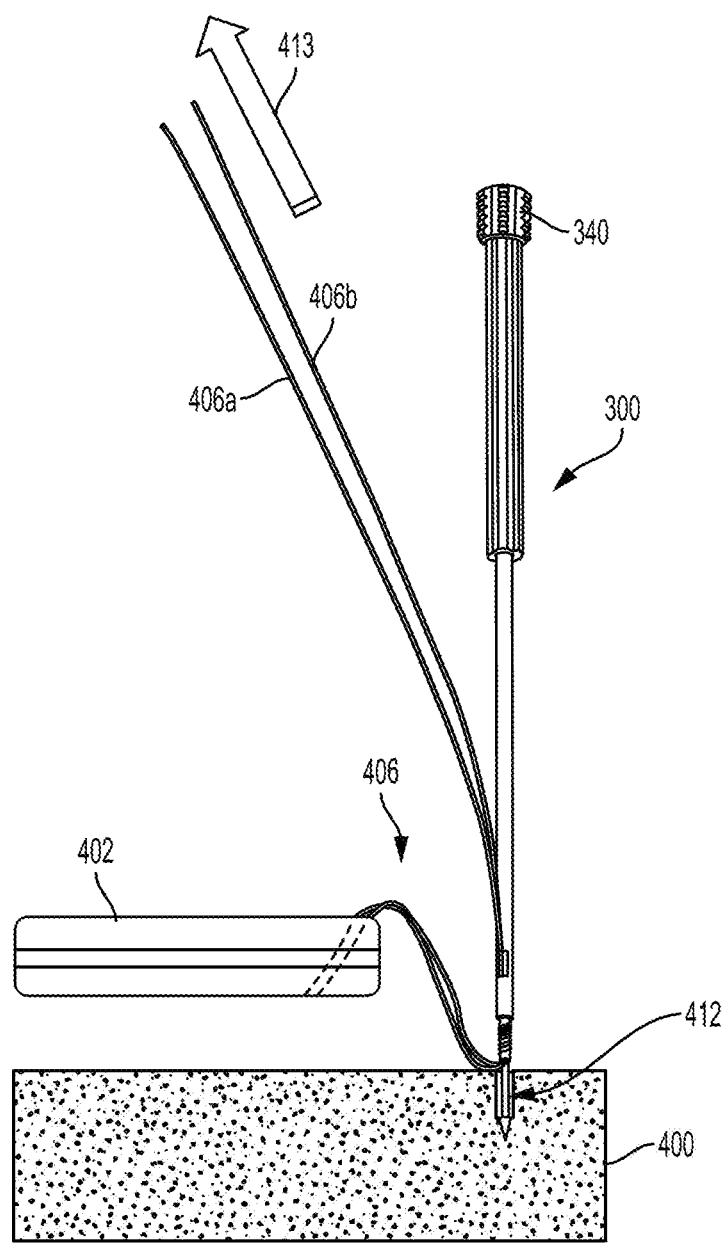
FIG. 15D illustrates the surgical system of FIG. 15C, showing the distal end of the elongate shaft driven distally into the bone.
Figure 15E:
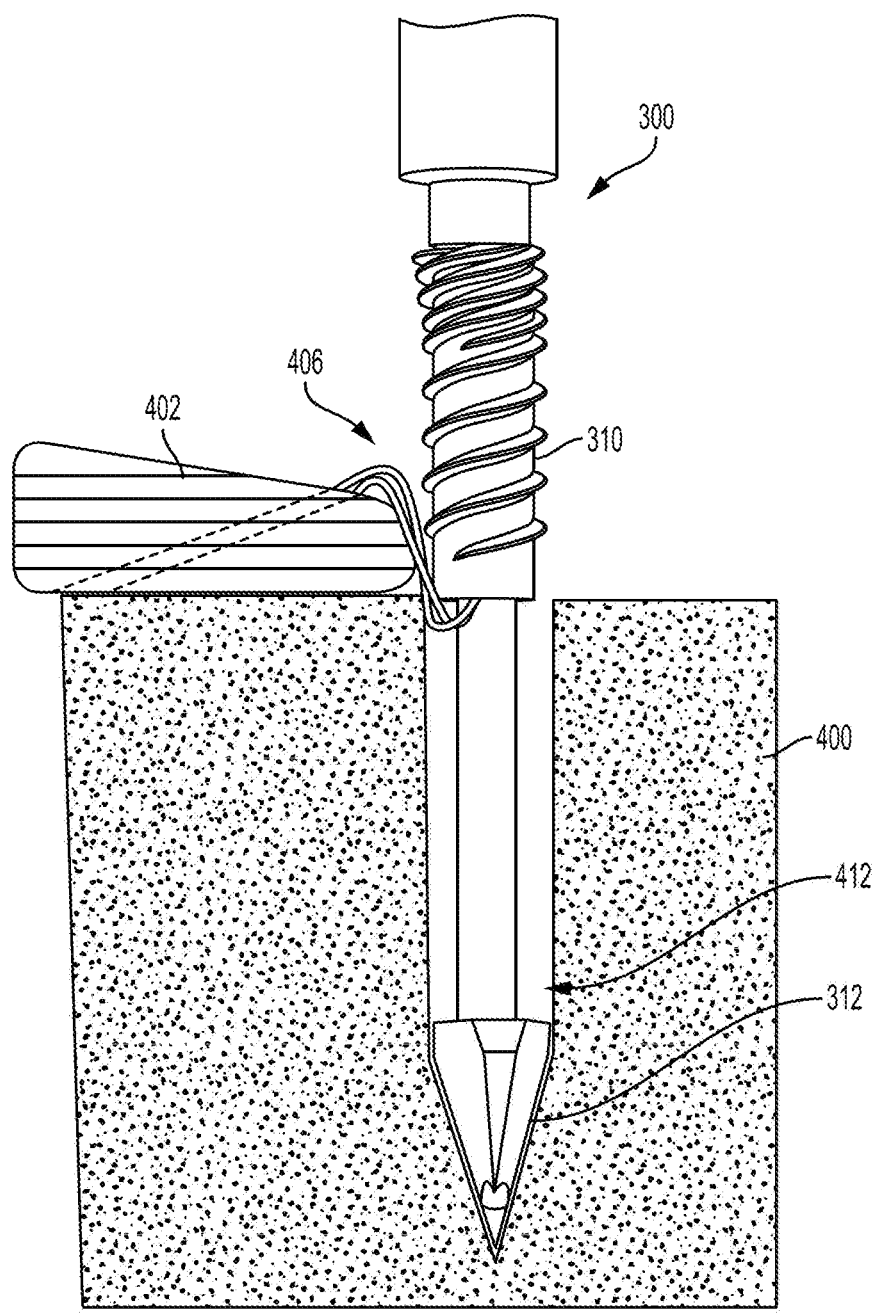
FIG. 15E illustrates the surgical system of FIG. 15D, showing a suture anchor near the bone.

As the elongate shaft 302 is driven distally into the bone 400, the dilator feature 312 widens the hole. Tension can be maintained on the terminal end portions 406a, 406b of the suture 406 as the distal end 302d of the elongate shaft 302 is inserted into the bone 400, as shown by an arrow 413 in FIG. 15D. The distal end 302d of the elongate shaft 302 can be driven into bone 400 such that the distal shaft portion 328 of the elongate shaft 302 with the dilator feature 312 coupled thereto is inserted into the hole 412 in the bone 400, as shown in FIGS. 15D and 15E. A portion of the central shaft portion 326 of the elongate shaft 302 is also inserted into the hole 412, whereas the suture anchor 310 is positioned at a desired position relative to the bone hole 412. In the illustrated embodiment, as shown in FIG. 15E, before being driven into the bone, the suture anchor 310 is positioned just proximal to the bone hole 412. In other embodiments, the suture anchor 310 can be at least partially inserted into the bone hole.

Figure 15F:
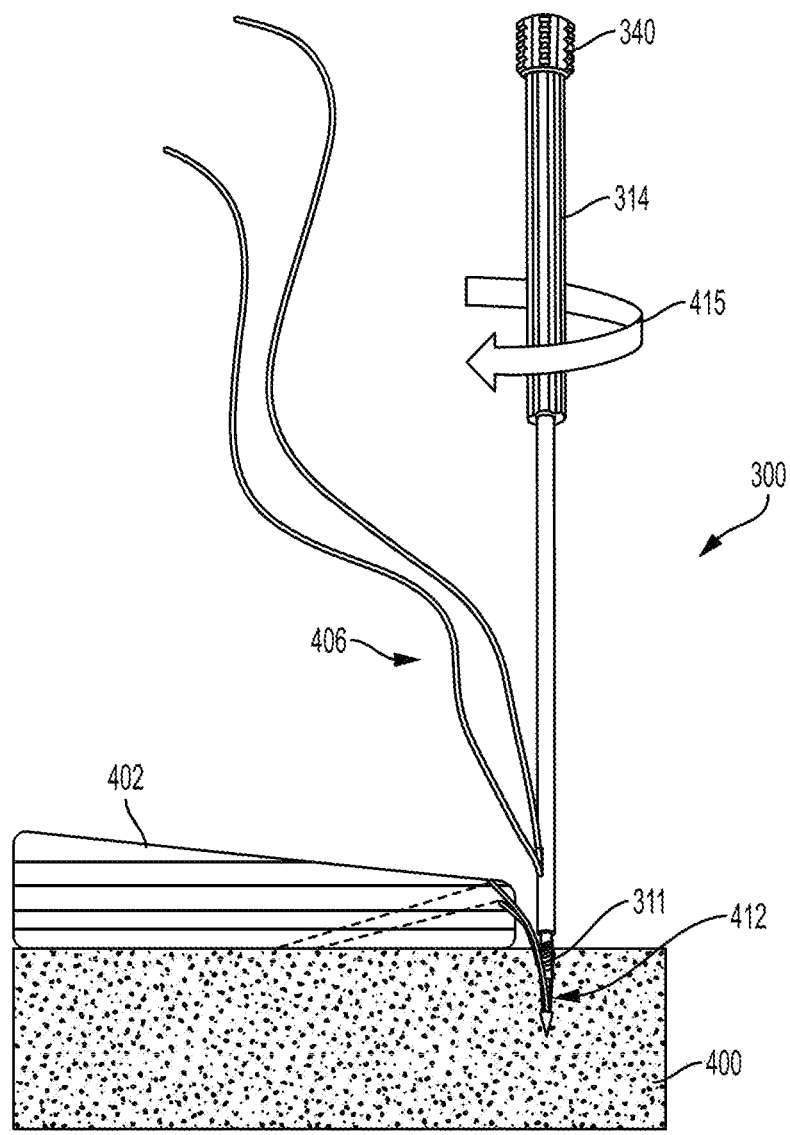
FIG. 15F illustrates the surgical system of FIG. 15E, showing a driver device rotated.
Figure 15G:
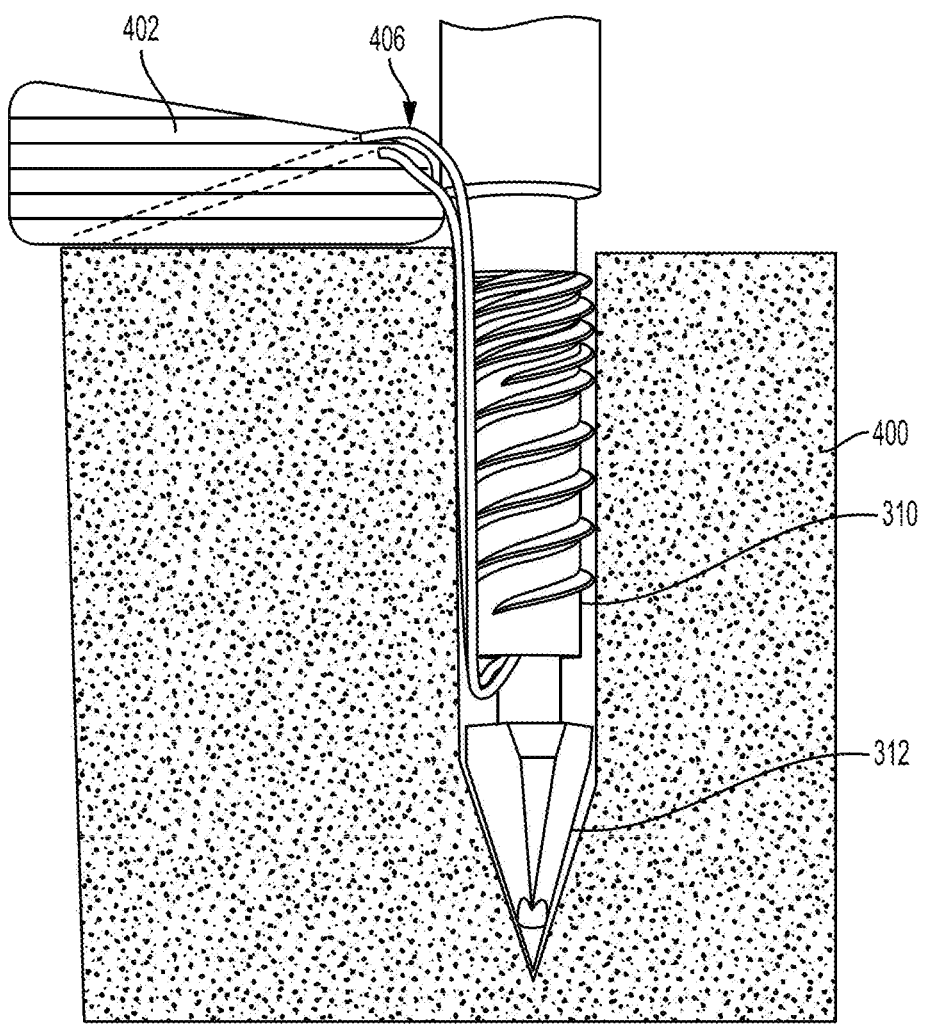
FIG. 15G illustrates the surgical system of FIG. 15F, showing the suture anchor driven into the bone.
Figure 15H:
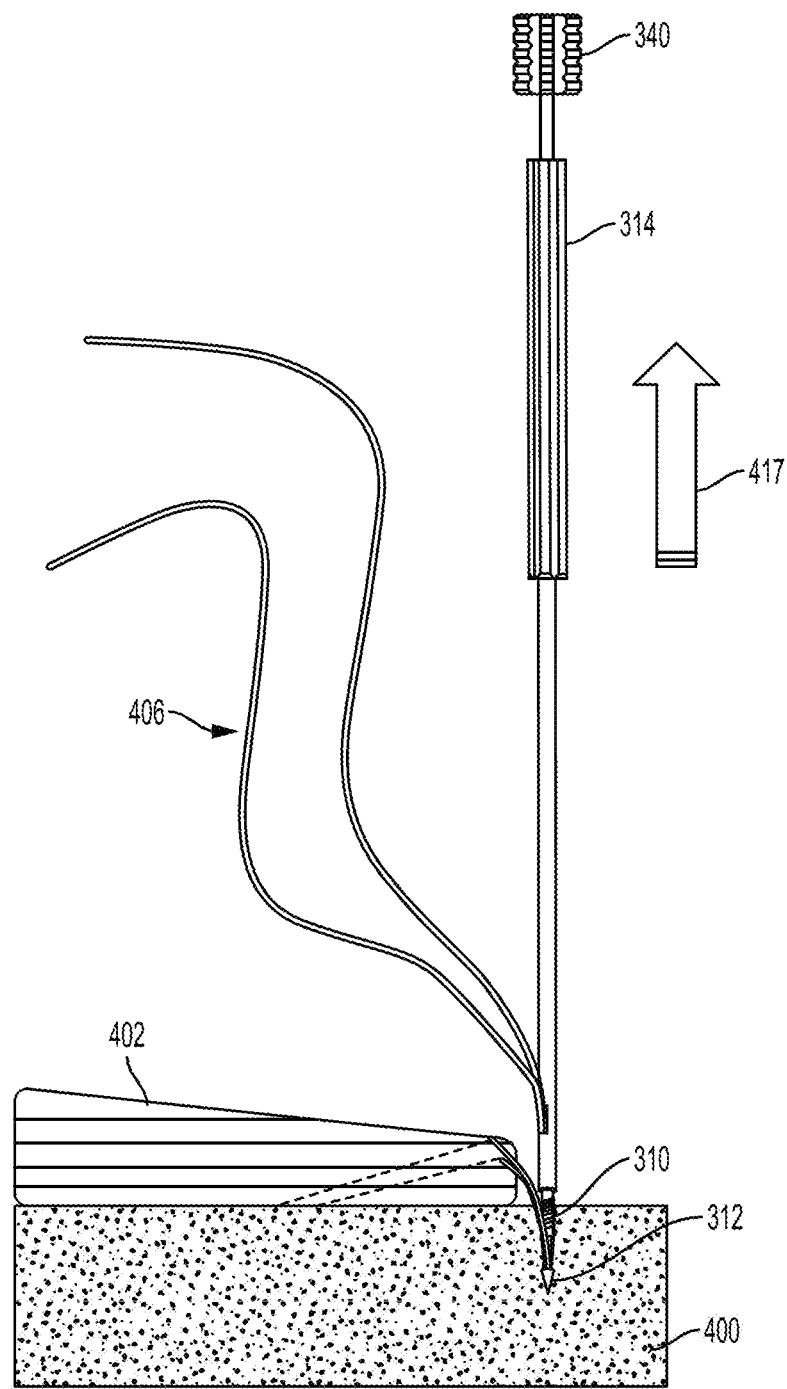
FIG. 15H illustrates the surgical system of FIG. 15G, showing the driver device and the elongate shaft being removed.

Once the distal end 302d of the elongate shaft 302 with the dilator feature 312 is driven into the bone 400 to a desired depth, the suture anchor 310 can be driven distally towards the dilator feature 312 and into the bone hole 412. In the illustrated embodiment, the driver device 304, with the distal driver member 320 thereof releasably coupled to the suture anchor 310, is activated to drive the suture anchor 310 distally into the bone hole 412. As shown in FIG. 15F, the driver device 304 can be rotated, such as by rotating the proximal handle 314 of the driver device 304, as shown by an arrow 415. The rotation causes the suture anchor 310 to advance distally towards the dilator feature 312 and into the bone 400, as shown in FIGS. 15F and 15G. The threads 311 of the suture anchor 310 engage the bone 400. As the driver device 304 is rotated, the elongate shaft 302, which extends through the lumen 322 of the driver device 304 and the dilator feature 312, remains stationary. For example, FIG. 15H illustrates that, after the driver device 304 has been driven distally, the proximal handle 314 of the driver device 304 is disposed offset from and more distal to the proximal handle 340 of the elongate shaft 302 than before the driver device 304 has been driven distally (e.g., FIG. 15F). The rotation of the driver device 304 causes the suture anchor 310 to move distally towards the distal feature 312 and into the bone 400, which causes the suture 406 to be secured between an interior wall of the bone hole 412 and an outer surface of the suture anchor 310.

Figure 15I:
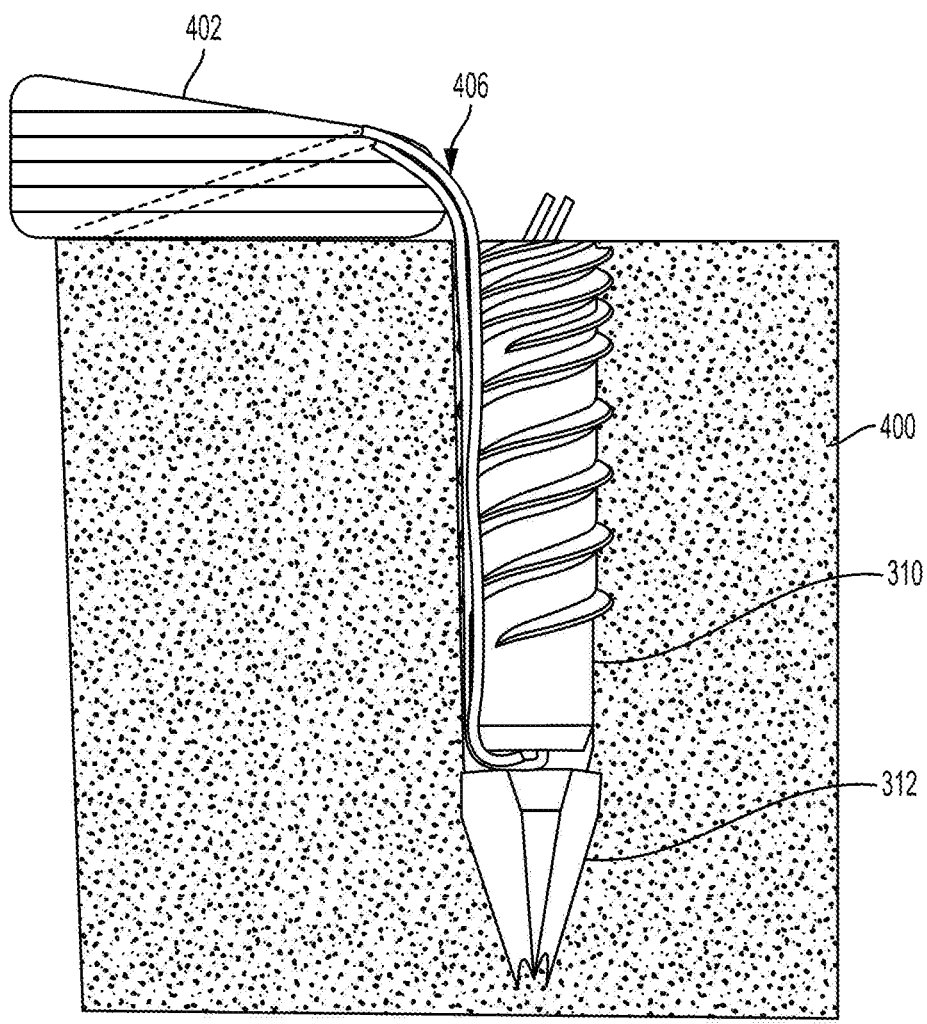
FIG. 15I illustrates the surgical system of FIG. 15H, showing the suture secured and trimmed.

Once the suture anchor 310 has been driven into the hole 412 in the bone 400, the elongate shaft 302 can be separated from the dilator feature 312, and the driver device 304 can be separated from the suture anchor 310, as shown schematically by an arrow 417 in FIG. 15H. In some embodiments, the elongate shaft 302 may not be coupled to the driver device 304, and the elongate shaft 302 may be separated from the dilator feature 312 and removed from the lumen 322 of the driver device 304 before the driver device 304 is separated from the suture anchor 310. In other embodiments, the elongate shaft 302 and the driver device 304 can be coupled to one another, and they can be separated from the dilator feature 312 and the suture anchor 310 substantially simultaneously. Regardless of the manner in which the elongate shaft 302 and the driver device 304 are removed, the dilator feature 312 and the suture anchor 310 with the suture 406 coupled thereto remain implanted in the bone hole 412, thereby attaching the tissue 402 to the bone 400, as shown in FIG. 15I. If desired, the terminal end portions 406a, 406b of the suture 406 can be trimmed using a suitable cutting instrument, and FIG. 15I illustrates by way of example the terminal end portions 406a, 406b trimmed. Also, in some embodiments, the terminal end portions 406a, 406b of the suture 406 can be passed through the tissue 402, or the terminal end portions 406a, 406b can be coupled to another suture anchor.

In some embodiments, a surgical system includes a pusher device, a driver device or driver, an elongate shaft, a suture anchor, and an implantable dilator feature. The pusher device has a proximal handle and a shaft extending therefrom, the shaft having a first lumen extending therethrough, and the pusher device having a first opening extending through a side thereof. The driver has a proximal handle and a shaft extending therefrom and having a second lumen extending therethrough, the shaft of the driver extending at least partially through the first lumen of the pusher device, and the driver having a second opening extending through a side thereof, the second opening communicating with the first opening. The elongate shaft can be proximally retractably disposed within the second lumen such that the elongate shaft can move between retracted and advanced configurations. At least one suture can be coupled to the surgical system when the elongate shaft is in the retracted configuration. The suture anchor having external threads formed thereon has a third lumen extending therethrough that removably receives therein a distal driver member of a driver shaft of the driver. The dilator feature can be removably disposed on the distal driver member distal to the suture anchor.

Figure 16:
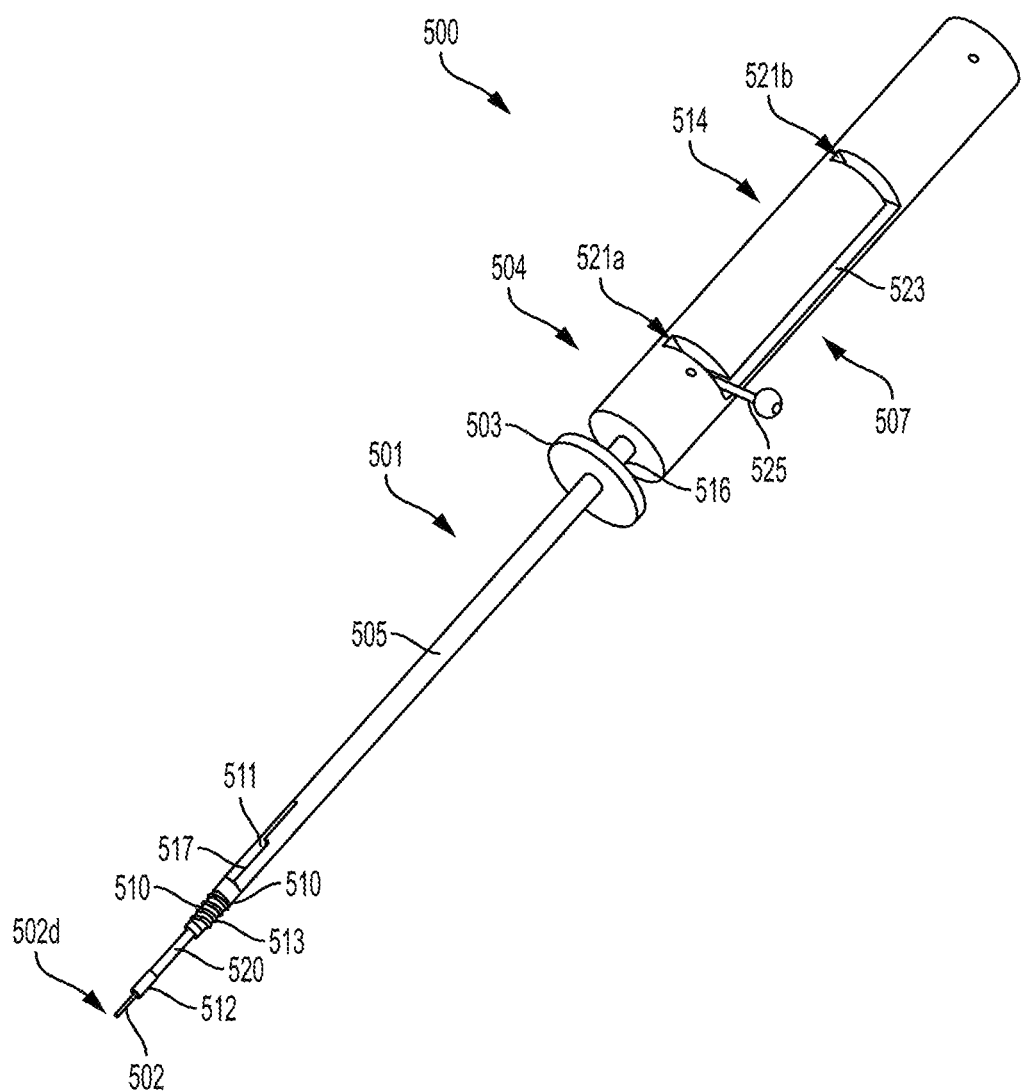
FIG. 16 is a perspective view of another embodiment of a surgical system.

FIGS. 16-20I illustrate another embodiment of a surgical system 500 that includes an overtube or pusher device 501, an elongate shaft 502, a driver device or driver 504 that receives the elongate shaft 502 at least partially therethrough, a suture anchor 510, and a dilator feature 512 that can be implantable. In the illustrated embodiment, the driver device 504 can have a proximal handle 514. The pusher device 501 also can have a proximal handle 503 coupled to a proximal end thereof. As shown in FIG. 16, the proximal handle 514 of the driver device 504 is disposed proximally to the handle 503 of the pusher device 501. In the illustrated embodiment, the elongate shaft 502 is coupled to a retraction mechanism 507 that is disposed in the proximal handle 514 of the driver 504, the retraction mechanism 507 being configured to be activated to cause the elongate shaft 502 to move between a retracted configuration and an extended configuration, as discussed in more detail below.

Figure 17A:
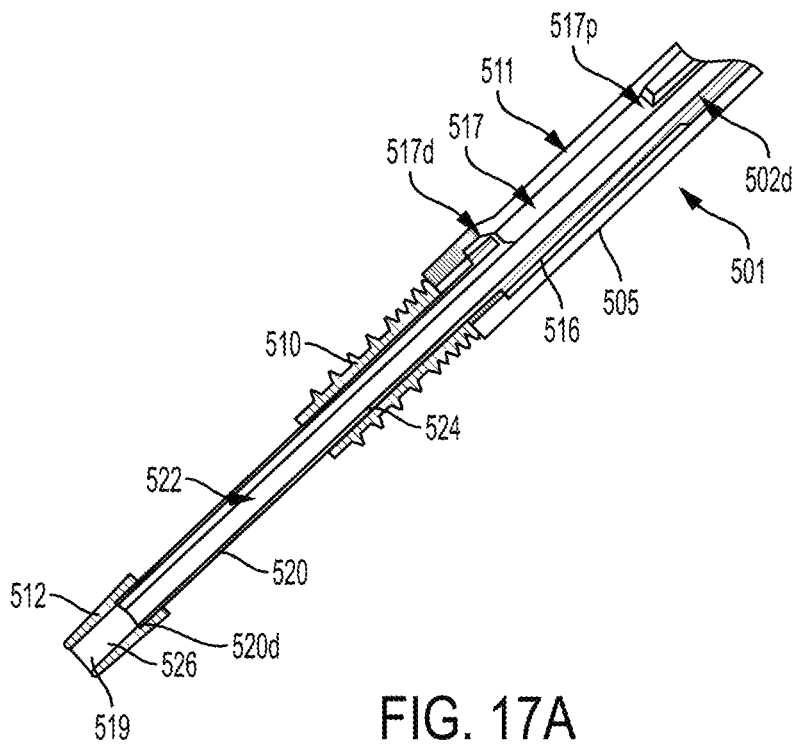
FIG. 17A is a cross-sectional view of the surgical system of FIG. 16, showing an elongate shaft in a retracted configuration.
Figure 17B:
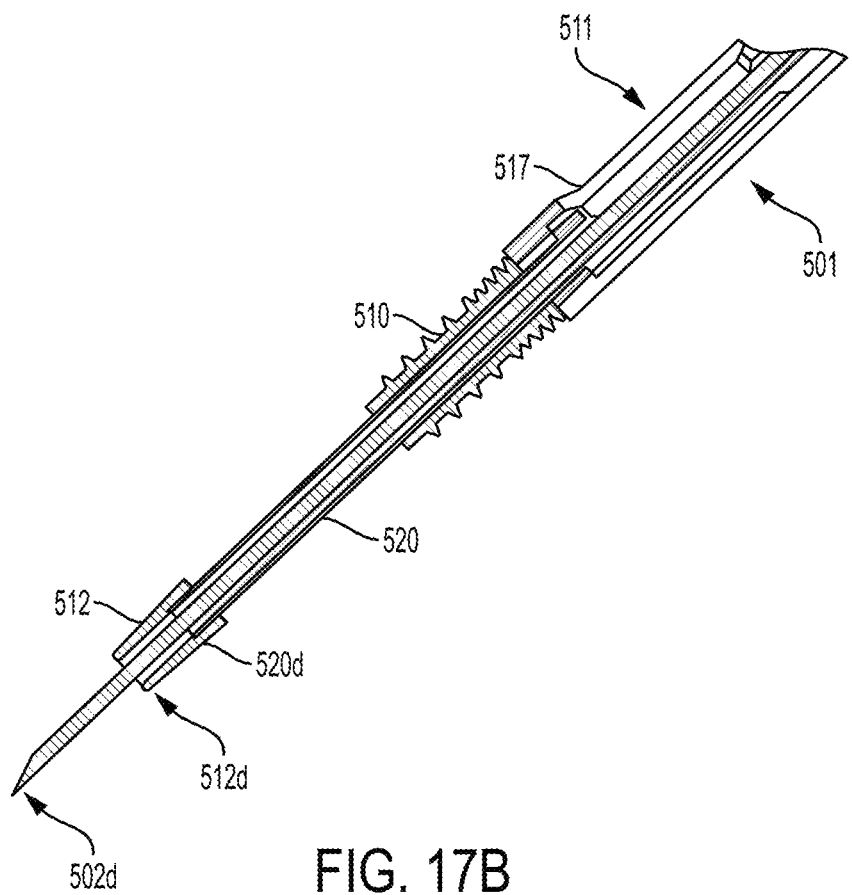
FIG. 17B is a cross-sectional view of the surgical system of FIG. 17A, showing the elongate shaft in an advanced configuration.

The components of the system 500 can have various configurations. The pusher device 501, configured to apply force to the suture anchor 510 as discussed below, can have various configurations. As shown in FIGS. 16, 17A, and 17B, the pusher device 501 has a shaft 505 extending distally from the proximal handle 503 of the pusher device 501. The shaft 505 of the pusher device 501 has a lumen 509 extending therethrough that receives the driver 504 therethrough. The pusher device 501 has an opening 511 extending through a side thereof.

The driver 504, configured to drive the suture anchor 510 into bone, also can have various configurations. In the illustrated embodiments, the driver 504 has a driver shaft 516 extending distally from the proximal handle 514 of the driver 504 and having a lumen 522 extending therethrough. As shown in FIGS. 17A and 17B, the driver shaft 516 has a distal driver member 520 that extends from a point or feature within the drive shaft 516 to a distal end 520d of the distal driver member 520, which is also a distal end of the driver shaft 516 of the driver 504. For example, as shown in FIGS. 17A and 17B, the driver shaft 516 can have a shoulder 518 proximal to the distal driver member 520 that extends from the shoulder 518 to the distal end 520d of the distal driver member 520. In the illustrated embodiment, the distal driver member 520 is configured to extend through the dilator feature 512 and through the suture anchor 510, as shown in FIGS. 17A and 17B.

In the illustrated embodiments, the driver shaft 516 of the driver 504 extends at least partially through the lumen 509 of the pusher device 501. Further, the driver 504 has in the driver shaft 516 thereof an opening 517 extending through a side of the driver shaft 516. In an assembled configuration, as shown in FIGS. 16, 17A, 17B, and 18, the opening 517 extending through the driver shaft 516 communicates with the opening 511 extending through the pusher device 501.

The lumen 522 of the driver shaft 516 is configured to receive the elongate shaft 502 therethrough such that the elongate shaft 502 can be proximally retractably disposed within the lumen 522. In the illustrated embodiments, the elongate shaft 502 is configured to move between a retracted configuration in which a distal end 502d of the elongate shaft 502 is disposed proximally to the opening 517 of the driver shaft 516, as shown in FIG. 17A, and an advanced configuration in which the distal end 502d of the elongate shaft 502 extends distally from a distal end 512d of the dilator feature 512, as shown in FIG. 17B. In the retracted configuration, the elongate shaft 502 can be disposed proximally to at least a distal end 517d of a wall of the driver shaft 516 defining the opening 517 that extends between the distal end 517d of the wall and a proximal end 517p of the wall of the driver shaft 502. As shown in FIG. 17A, the elongate shaft 502 can be disposed proximally to at least the proximal end 517p of the wall of the driver shaft 502 defining the opening 517. In the illustrated embodiments, the opening 511 of the pusher device 501 can have substantially the same length as a length of the opening 517 of the driver shaft 516, or the opening 511 of the pusher device 501 can have a greater length than a length of the opening 517 of the driver shaft 516. Regardless of the specific sizes of the opening 511 of the pusher device 501 and the opening 517 of the driver shaft 516, the openings 511, 517 are formed such that at least portions thereof are aligned to thereby allow a suture to pass from the lumen 522 of the driver shaft 516 and through both of the openings 511, 517.

In the illustrated embodiment, the elongate shaft 502 can have a reduced outer diameter, which, for example, can be smaller than an outer diameter of elongate shaft 502 of FIGS. 10-15I. In this way, the elongate shaft 502 can fit within the lumen 522 of the driver shaft 516 and allow one or more sutures to be passed along at least a portion of the elongate shaft 502 through the lumen 522 without a suture retaining feature being formed in the elongate shaft 502. However, in some embodiments, a suture retaining feature in the form of a groove, channel, or other feature can be formed in the elongate shaft 502.

The proximal handle 514 of the driver device 504 can have a variety of configurations. In the illustrated embodiment, the proximal handle 514 includes the retraction mechanism 507 configured to be activated to cause the elongate shaft 502 to move between a retracted configuration and an advanced configuration. The retraction mechanism 507 can have various configurations. For example, as shown in FIG. 16, the retraction mechanism 507 can include retaining first and second slots 521a, 521b communicating via a channel 523 in which a handle or lever 525 coupled to the elongate shaft 502 can be moved between the first, more distal slot 521a and between the more proximal slot 521b to thereby cause the elongate shaft 502 to move between advanced and retracted configurations, respectively. The lever 525, which can have a knob or any other feature that facilitates grip, can be operably coupled to the elongate shaft 502 in any suitable manner. Furthermore, some embodiments, the elongate shaft 502 and the lever 525 can be integrally formed. It should be appreciated that the retraction mechanism 507 is shown in the illustrated embodiment by way of example only, as any suitable mechanism can be used additionally or alternatively to enable the elongate shaft 502 to move between the advanced and retracted configurations.

Figure 18A:
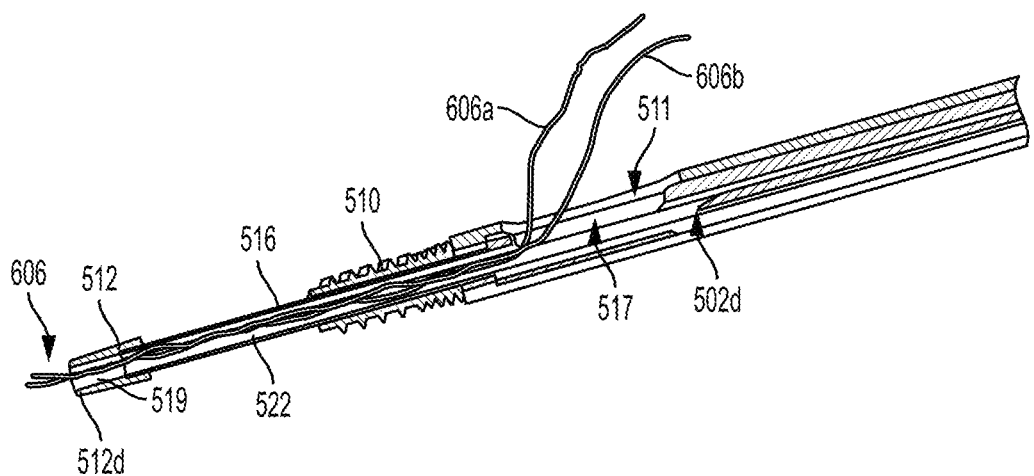
FIG. 18A is a cross-sectional view of the surgical system of FIG. 16, showing an elongate shaft in a retracted configuration, and a suture coupled to the surgical system.
Figure 18B:
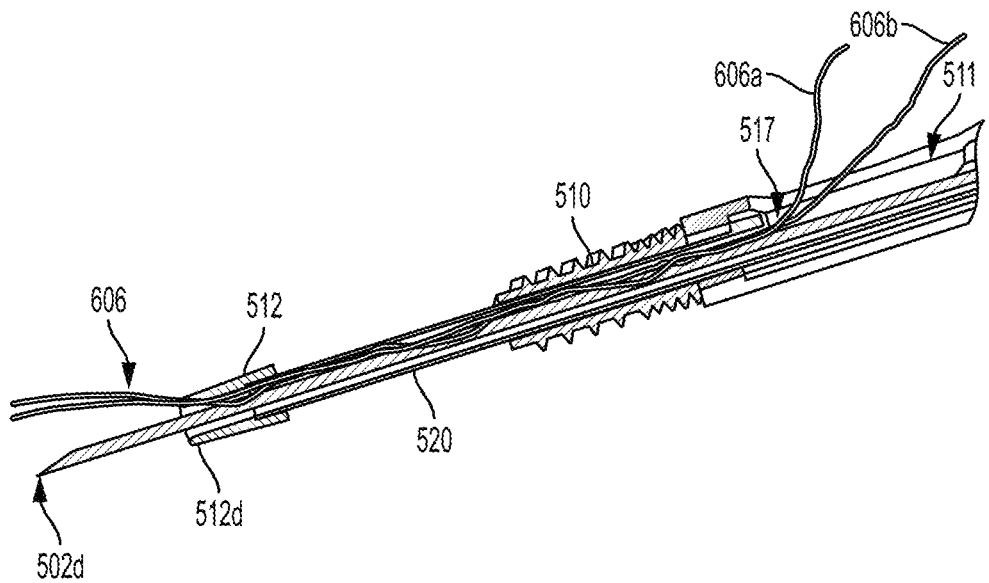
FIG. 18B is a cross-sectional view of the surgical system of FIG. 18A, showing the elongate shaft in an advanced configuration, and the suture coupled to the surgical system.

When the elongate shaft 502 is in the retracted configuration, as shown in FIGS. 17A, the distal end 502d thereof can be disposed proximal to the distal end 517d of the wall of the driver shaft 516 defining the opening 517 of the driver shaft 516. The distal end 502d of the elongate shaft 502 can be disposed proximal at least a portion of each of the openings 511, 517 in the pusher tube 501 and the driver shaft 516 so as to allow at least one suture to be passed through a portion of the lumen 522 of the driver shaft 516. With reference to FIG. 17A, when the elongate shaft 502 is absent from the portion of the lumen 522, such portion, extending between the distal end 520d of the lumen 522 of the driver shaft 516 and a point within the lumen 522 where the distal end 502d of the elongate shaft 502 is disposed, can receive at least one suture 606 to therethrough. FIG. 18A illustrates the elongate shaft 502 in the retracted configuration and the suture 606 passed through the lumen 522 of the driver shaft 516 such that the suture 606 enters the lumen 522 from a distal end 512d of the dilator feature 512, extends through a lumen 526 of the dilator feature 512, through the lumen 522, and exits the lumen 522 through the openings 511, 517 of the pusher tube 501 and the driver shaft 516, respectively. As shown, terminal end portions 606a, 606b of the suture 606 extends out of the opening 511 of the pusher tube 501. Once the suture 606 is coupled to the system 500 as shown in FIG. 18A, the retraction mechanism 507 can be activated, such as by moving the lever 525 distally, to thereby cause the elongate shaft 502 to move distally. FIG. 18B shows the elongate shaft 502 in the advanced configuration in which the distal end 502d of the elongate shaft 502 extends distally from the distal end 512d of the dilator feature 512.

The suture anchor 510 can have various configurations. In the illustrated embodiment, the suture anchor 510 has one or more external threads 513 formed thereon configured to engage the suture anchor 510 with the bone. The suture anchor 510 can have any suitable configuration and can have other bone-engaging features. The suture anchor 510 can have a lumen 524 extending therethrough such that at least in a portion of the lumen 524 can receive therein the distal driver member 520 of the driver 504. In an assembled configuration, as shown in FIG. 18B, the distal driver member 520 extends through the lumen 524 of the suture anchor 510 and further distally into the lumen 526 of the dilator feature 512 that is mounted on the distal driver member 520 distally to the suture anchor 510. As shown in FIG. 16, in an assembled configuration, a distal end of the pusher device 501 abuts a proximal end 510p of the suture anchor 510. In this way, the pusher device 501 can be used to apply force to the suture anchor 510 when the suture anchor 510 is driven into bone, as discussed in more detail below.

The dilator feature 512 can also have various configurations. The dilator feature 512 is configured to facilitate insertion of the elongate shaft 502 into bone by widening a hole in the bone once the hole is initiated, such as by the distal end 502d of the elongate shaft 502. The dilator feature 512 can be distally tapered and it can be in the form of a truncated cone, truncated pyramid having any suitable number of faces, etc. In some embodiments, similar to dilator feature 112 (FIGS. 1-10B) and dilator feature 312 (FIGS. 10-15I), the dilator feature 512 can be implantable and it can be made from a non-metallic material, and the dilator feature 512 can be bioabsorbable and/or biodegradable. However, in other embodiments, the dilator feature 512 can be made from a metal.

In the illustrated embodiments, the distal driver member 520 of the driver 504 is configured to releasably mate with the suture anchor 510 and to thereby drive the suture anchor 510 mated thereto distally into bone. As shown in FIGS. 17A-18B, the distal driver member 520 also releasably mates with the dilator feature 512. In some embodiments, as illustrated herein, the distal driver member 520 can be in the form of a male feature configured to be received within a corresponding female feature formed on at least a portion of an interior wall defining the lumen of the suture anchor 510. For example, the male feature can be hexagonal-shaped, and the corresponding female drive feature of the suture anchor 510 can be a corresponding hexagonal-shaped female feature formed in at least a portion of an interior wall defining the lumen 524 of the suture anchor 510. In the illustrated embodiment, the distal driver member 520 extends through the entirety of the lumen 524 of the suture anchor 510, and the entirety of the interior wall of the suture anchor 510 defining the lumen 524 can be configured to releasably mate with the distal driver member 520. At least a portion of an interior wall defining the lumen 526 of the dilator feature 512 releasably mounted on the distal driver member 520 of the driver shaft 516 of the driver 504 can also be in the form of a female feature configured to releasably mate with the male drive feature of the distal driver member 520. For example, as in the illustrated embodiment, at least a portion of the interior wall defining the lumen 526 of the dilator feature 512 can be hexagonal-shaped. It should be appreciated that the male feature of the distal driver member 520 and the corresponding female features of the suture anchor 510 and the dilator feature 512 can have any other configurations (e.g., square).

In the illustrated embodiment, a distal portion 519 of the interior wall defining the lumen 526 adjacent to the distal end 512d of the dilator feature 512 may not have a female feature, such as a hexagonal, square, or other feature configured to mate with the distal driver member 520. The distal portion 519 of the interior wall defining the lumen 526 of the of the dilator feature 512 can be circular in cross-section, which facilitates passage of a suture through the distal end 512d of the dilator feature 512.

Figure 19:
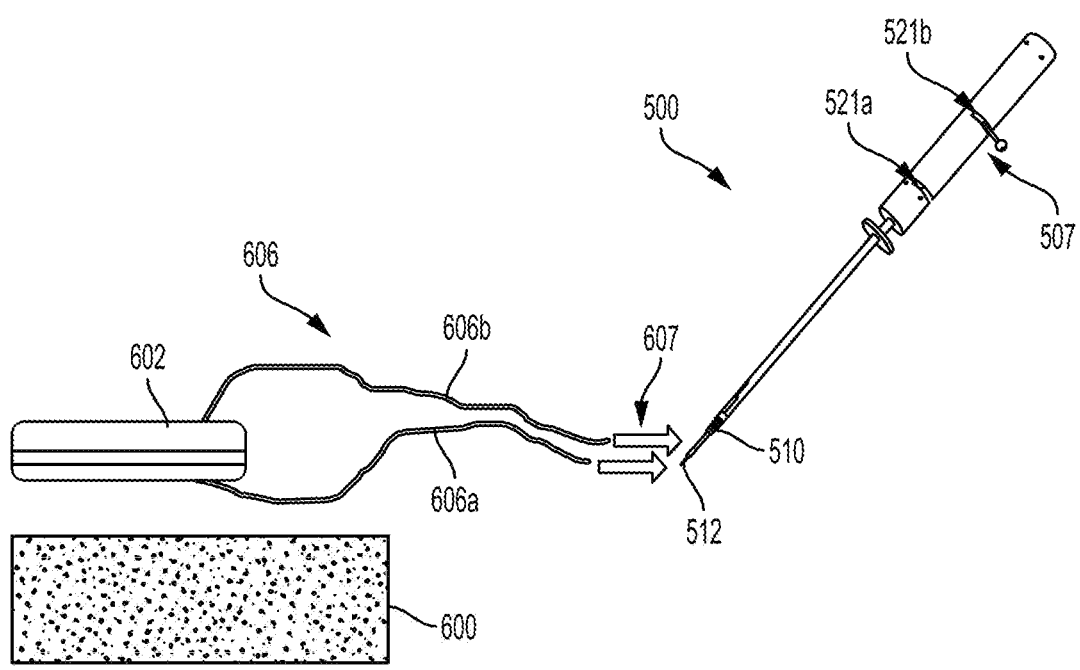
FIG. 19 illustrates the surgical system of FIG. 16, showing the surgical system near bone and an elongate shaft in a retracted configuration.
Figure 20A:
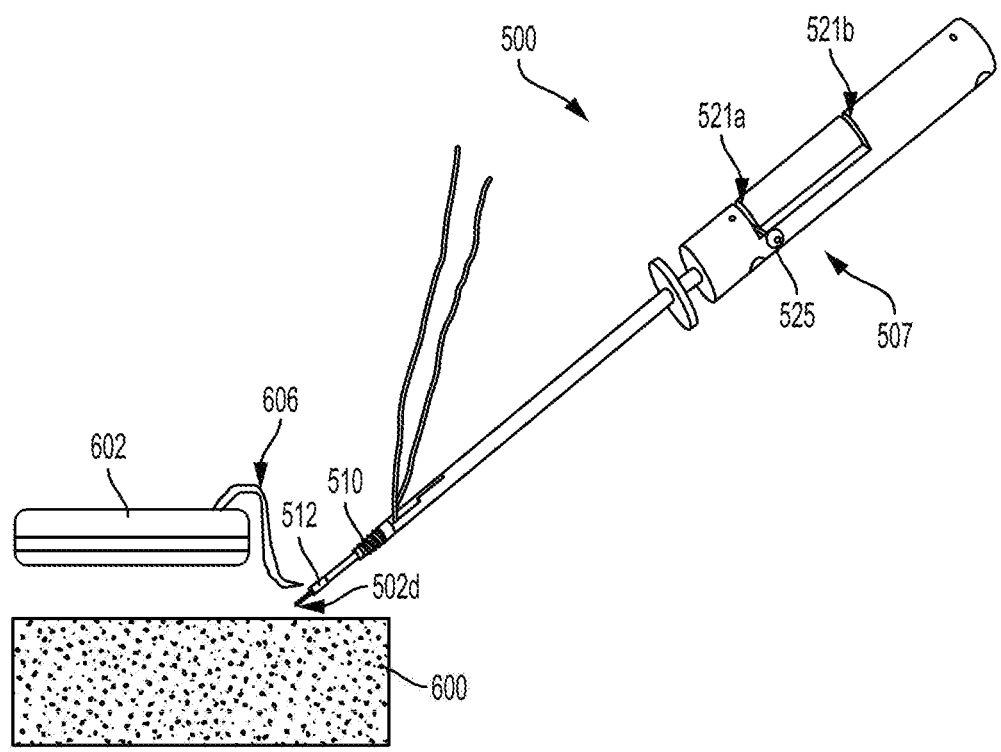
FIG. 20A illustrates the surgical system of FIG. 19, showing a suture coupled thereto, and an elongate shaft in an advanced configuration.
Figure 20B:
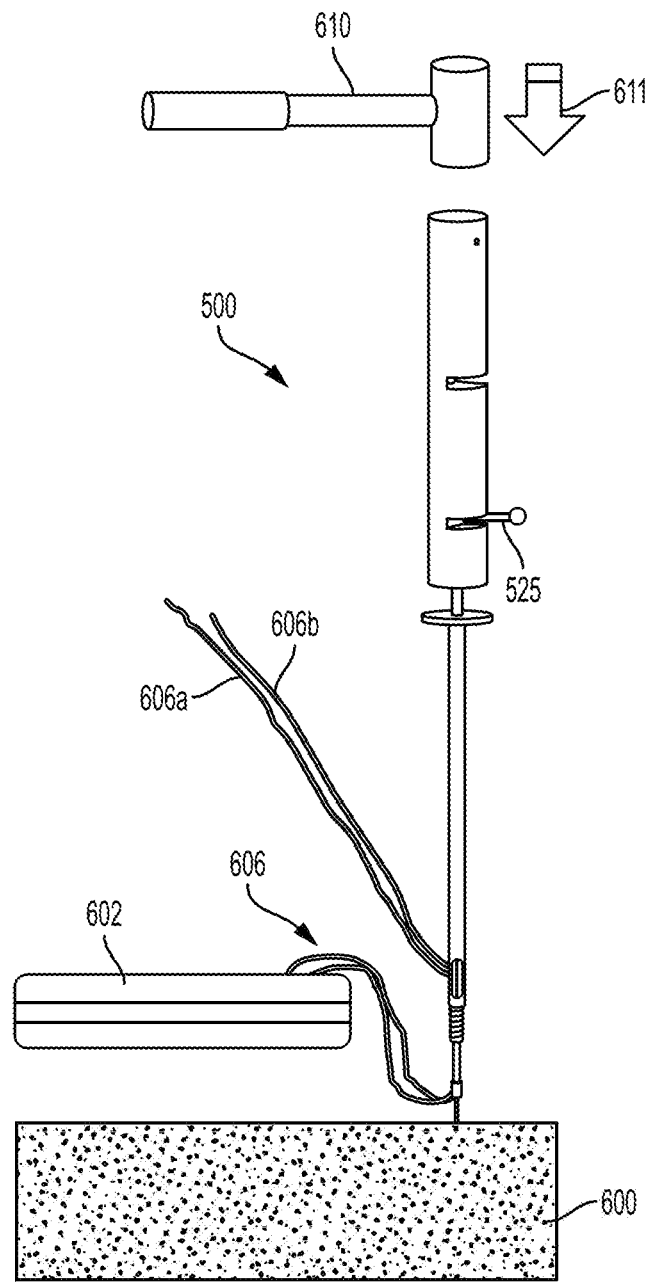
FIG. 20B illustrates the surgical system of FIG. 20A, showing a distal end of an elongate shaft initiating a hole in the bone.
Figure 20C:
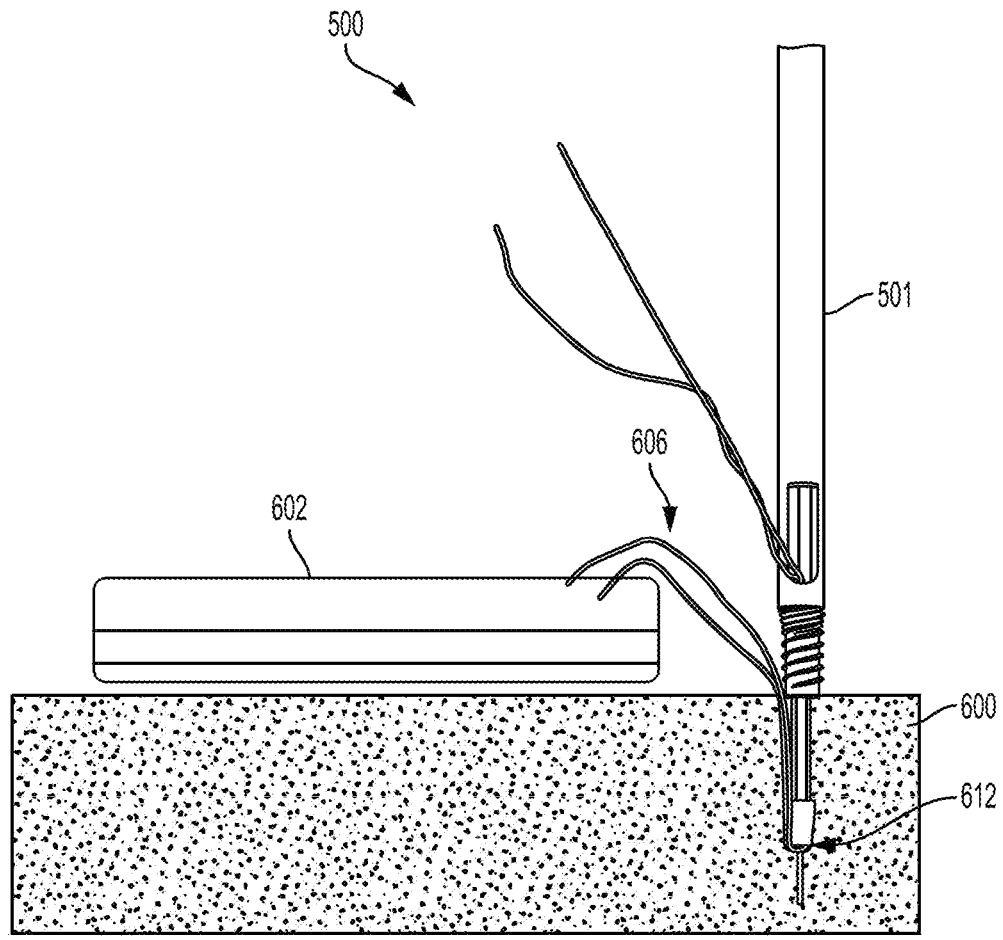
FIG. 20C illustrates the surgical system of FIG. 20B, showing the distal end of the elongate shaft driven distally into the bone.
Figure 20D:
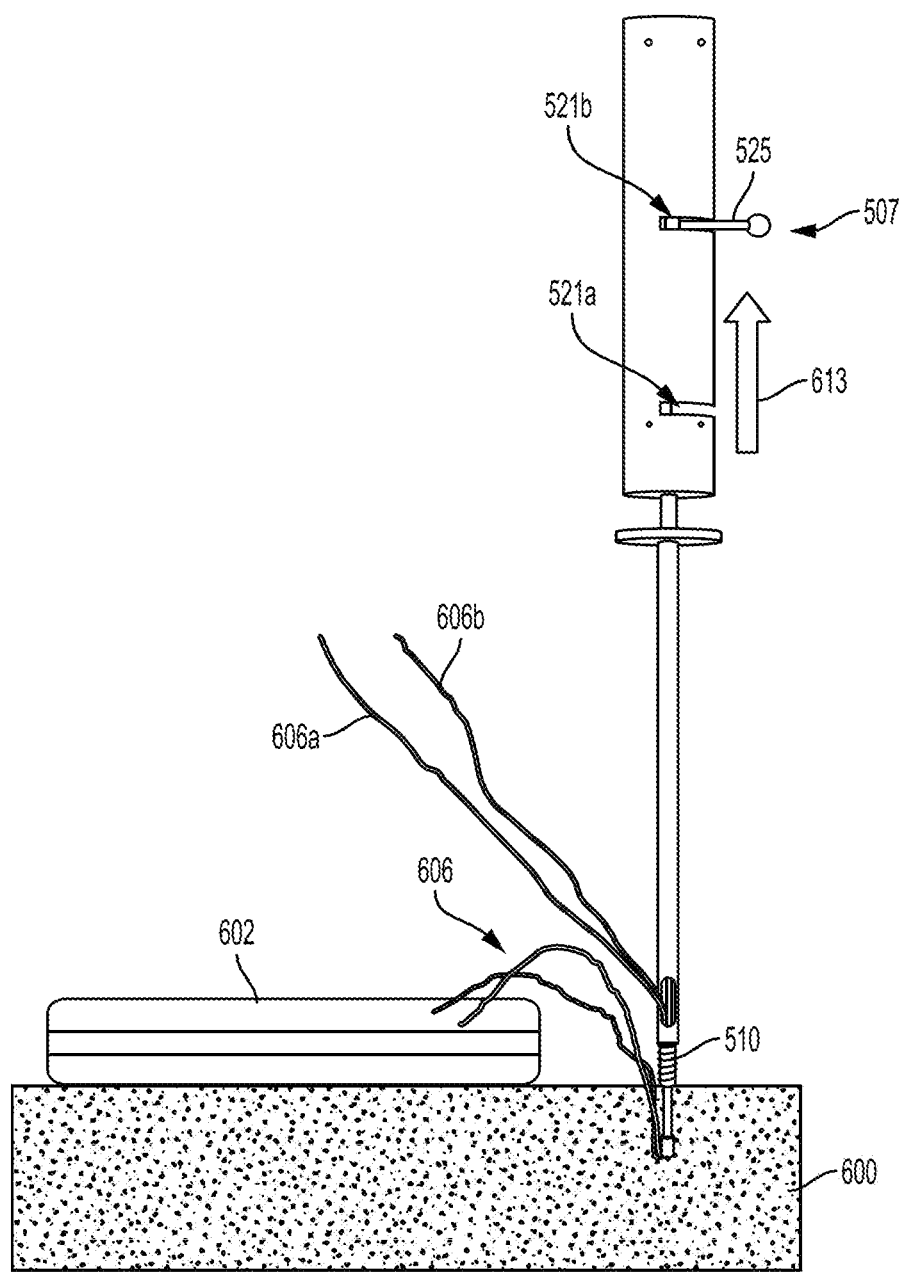
FIG. 20D illustrates the surgical system of FIG. 20C, showing the elongate shaft in a retracted configuration.
Figure 20E:
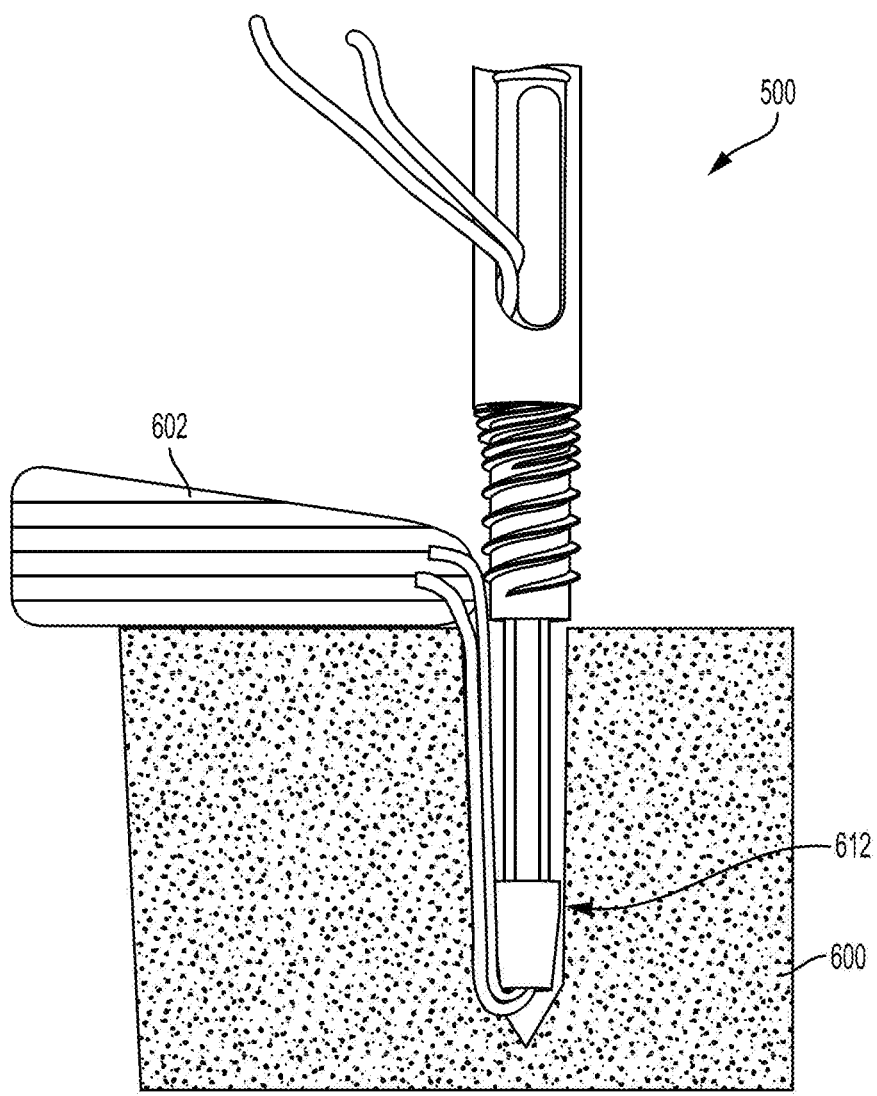
FIG. 20E illustrates the surgical system of FIG. 20D, showing the suture anchor near the bone.
Figure 20F:
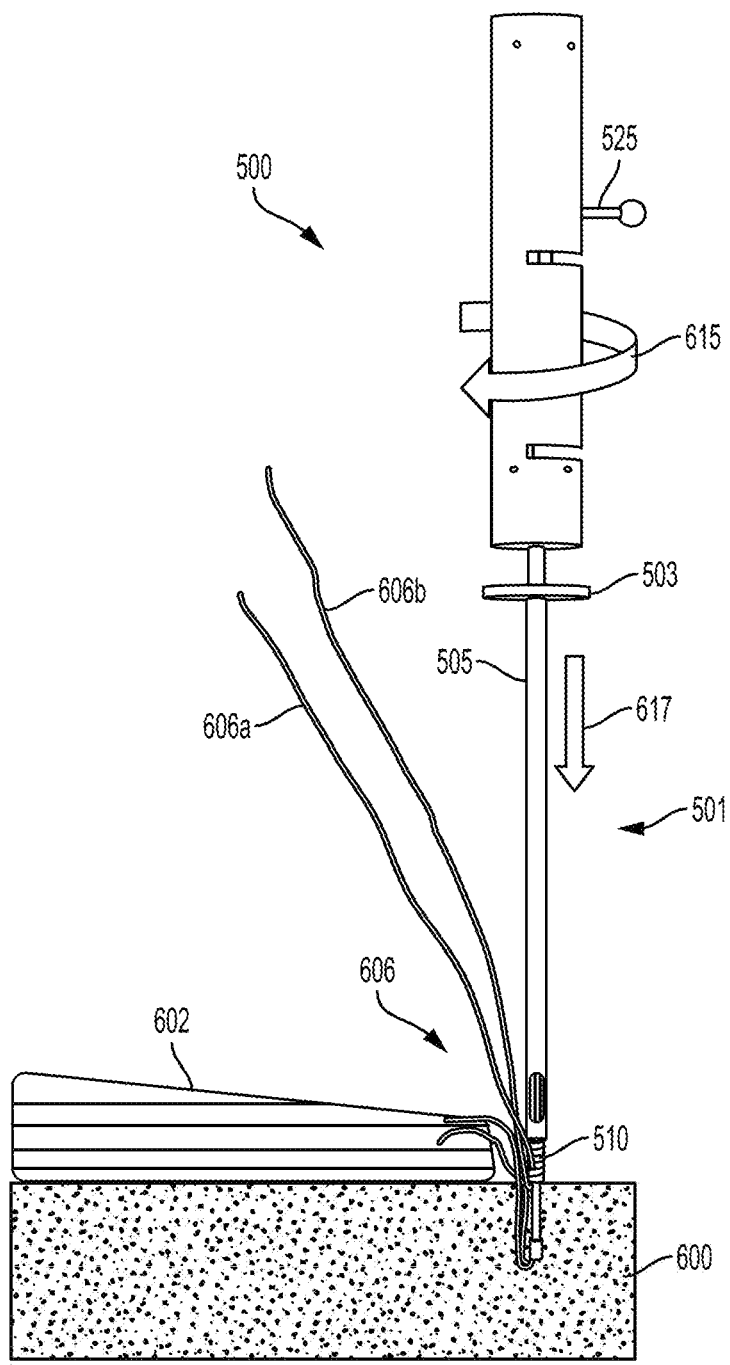
FIG. 20F illustrates the surgical system of FIG. 20E, showing a driver device rotated.
Figure 20G:
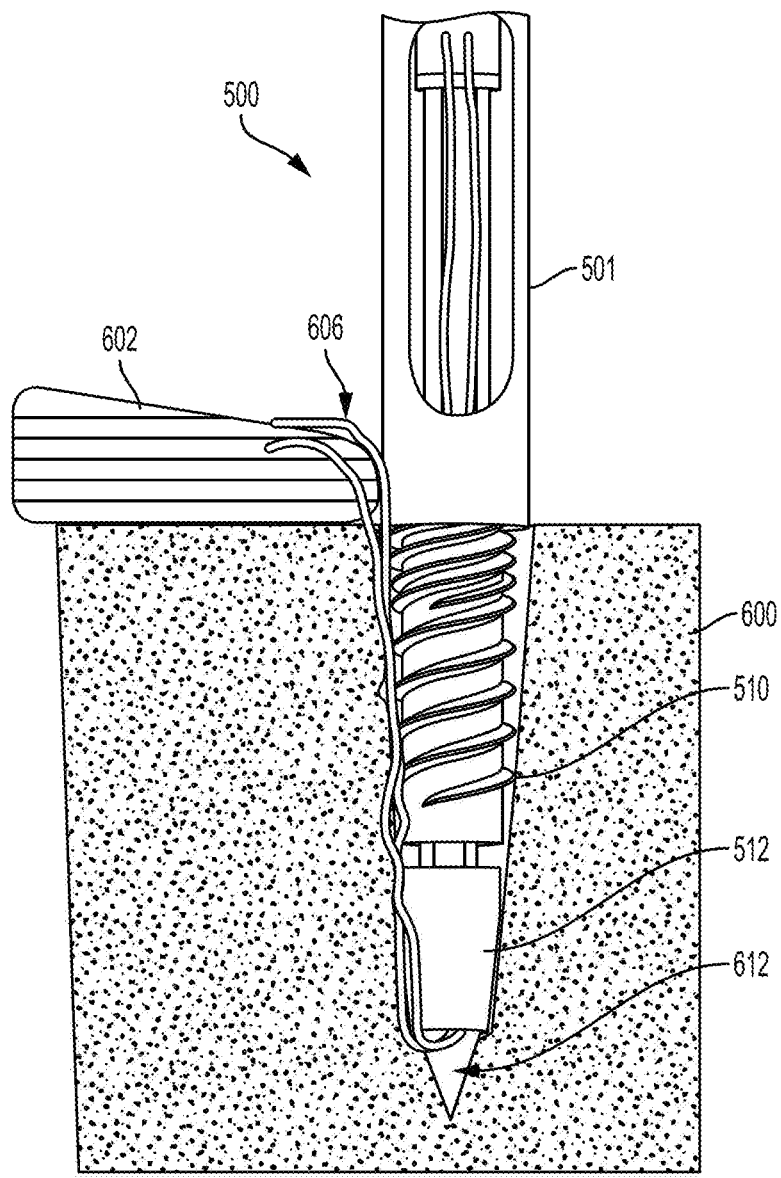
FIG. 20G illustrates the surgical system of FIG. 20F, showing the suture anchor driven into the bone.
Figure 20H:
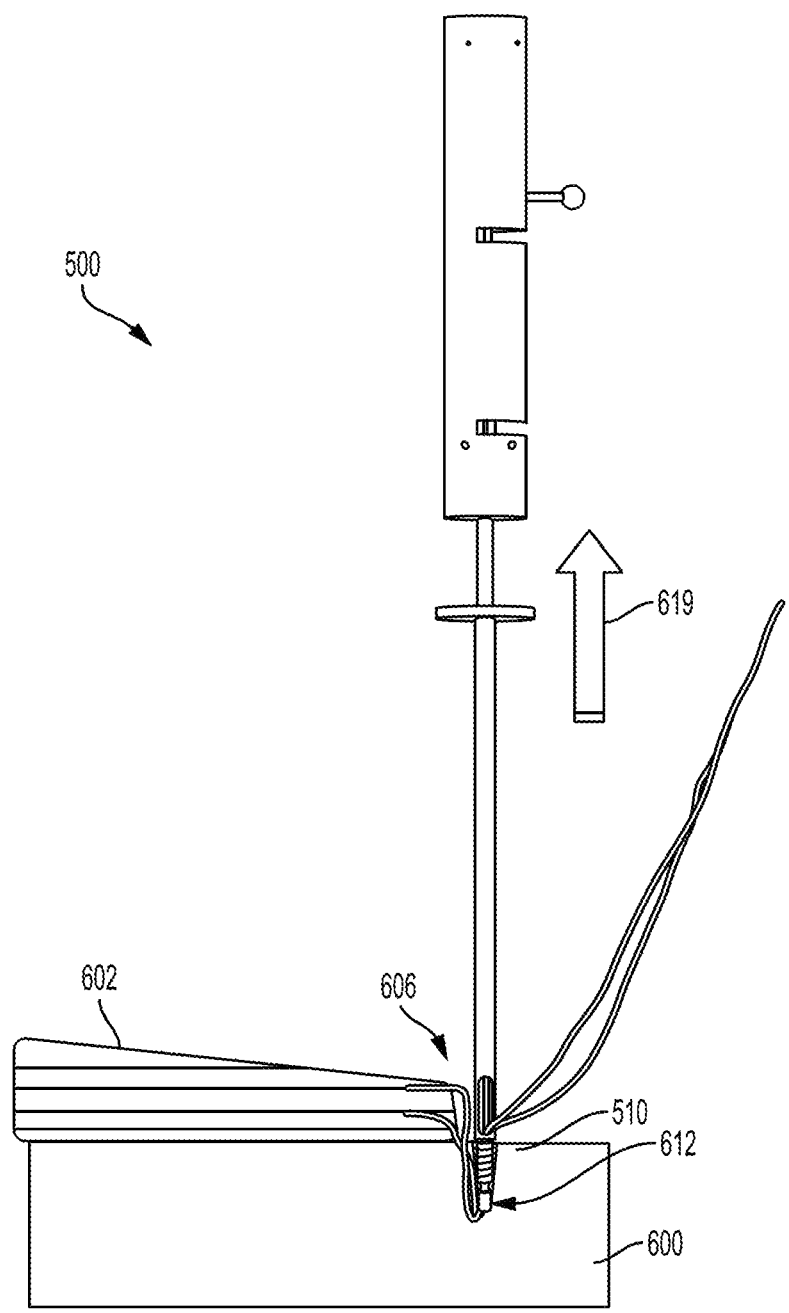
FIG. 20H illustrates the surgical system of FIG. 20G, showing the driver and a pusher device being removed.
Figure 20I:
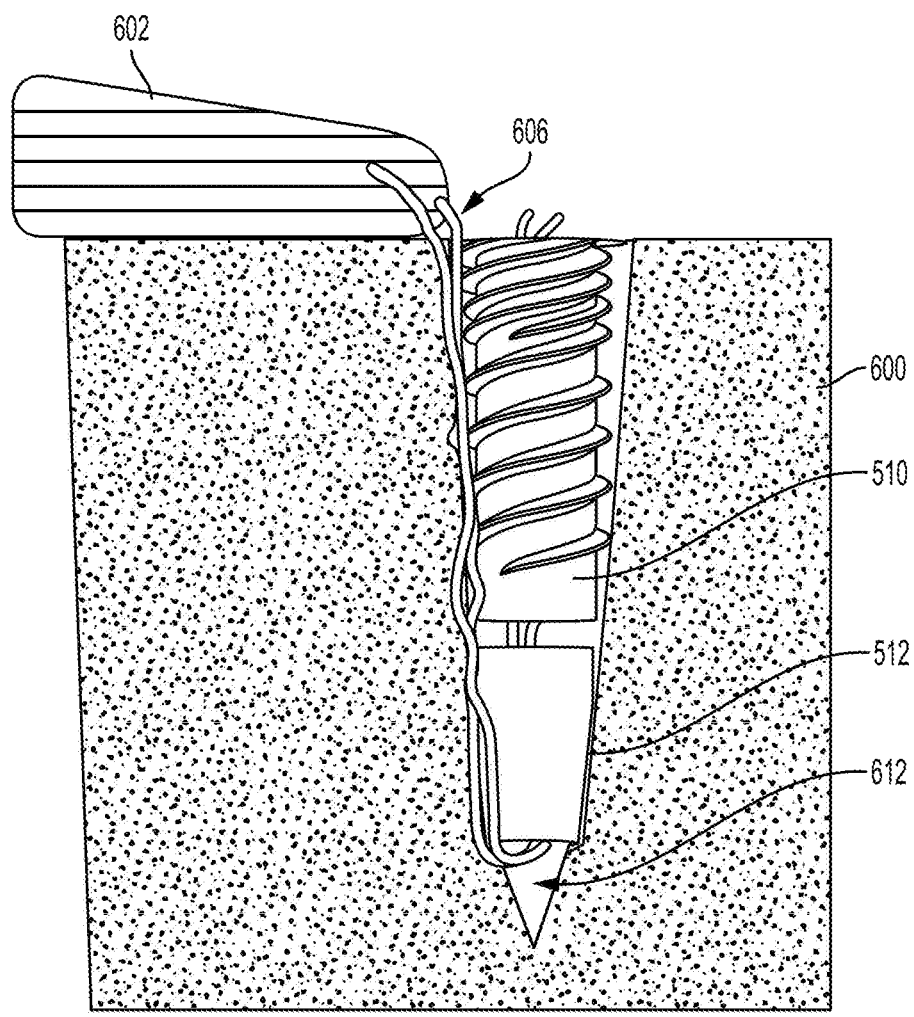
FIG. 20I illustrates the surgical system of FIG. 20H, showing the suture secured and trimmed.

FIGS. 19-20I illustrate the surgical system 500 used in a surgical repair method to attach soft tissue 602 (e.g., tendon) to bone 600. It should be appreciated that the surgical repair method in accordance with the described embodiments can be performed using other surgical systems, including surgical systems in which one or more components can be different from those included in the surgical system 500.

FIG. 19 illustrates schematically (arrows 607) that the terminal end portions 606a, 606b of the suture 606 are coupled to the system 500. In FIG. 19, the elongate shaft 502 is in the retracted configuration, as shown in FIG. 17A. The lever 525 of the retraction mechanism 507 of the proximal handle 514 of the driver 504 is disposed in the proximal slot 521b. In such a configuration, the suture 606 can be passed through the dilator feature 512, through the lumen 522 of the distal driver member 520 extending through at least a portion of the dilator feature 512 and through the suture anchor 510, and through the opening 517 of the driver 504 and the opening 511 of the pusher tube 501, the openings 511, 517 being at least partially aligned with one another. As shown in FIG. 19, the suture 606 can be passed through or otherwise coupled to tissue 602 such that the terminal end portions 606a, 606b of the suture 606 can engage with the system 500. It should be appreciated that in some embodiments the suture 606 can be coupled to tissue after the suture 606 has been coupled to the system 500.

Once the suture 606 is associated with the system 500 as shown, for example, in FIG. 18A, the elongate shaft 502 can be moved to an advanced configuration. For example, the lever 525 of the retraction mechanism 507 can be moved distally, as shown in FIG. 20A, to thereby cause the elongate shaft 502 to advance distally. In this way, the elongate shaft 502 is positioned such that its distal end 502d extends distally beyond the dilator feature 512, as shown in FIG. 18B. FIG. 20A illustrates the suture 606 being coupled to the system 500 and the elongate shaft 502 moved to the advanced configuration.

FIG. 20B illustrates the distal end 502d of the elongate shaft 502 inserted the bone 600 to initiate a hole at a desired location in the bone 600. Tension can be applied and maintained on the suture 606 while the distal end 502d of the elongate shaft 502 is used to initiate a hole in the bone 600. FIG. 20B also illustrates that, once the hole in the bone 600 is initiated, a suitable instrument 610, such as mallet, hammer, or other instrument, is used to drive the elongate shaft 502 further distally into the bone 600, as shown by an arrow 611.

As the elongate shaft 502 is driven distally into the bone 600, the dilator feature 512 widens the hole. Tension can be maintained on the terminal end portions 606a, 606b of the suture 606 as the distal end 502d of the elongate shaft 502 is inserted into the bone 600. The elongate shaft 502 with the dilator feature 512 is driven into the bone 600 such that a hole 612 in the bone is formed and the dilator feature 512 releasably mounted on the distal driver member 520 of the driver shaft 516, and at least a portion of the distal driver member 520, are positioned in the hole 612, as shown in FIG. 20C. The suture anchor 510 can sit above the surface of the bone 600, just proximal to the bone hole 612. In some embodiments, the suture anchor 510 can be positioned partially within the hole 612 in the bone 600.

After the elongate shaft 502 is driven into the bone 600 to a desired depth to form the hole 612, the retraction mechanism 507 can be activated, such as by moving the lever 525 to from the distal slot 521*a* to the proximal slot 521*b* (as shown by an arrow 613 in FIG. 20D), which causes the elongate shaft 502 to be retracted, as also shown in FIG. 20D. FIG. 20E shows a distal portion of the system 500 with the elongate shaft 502 in the retracted configuration.

Once the elongate shaft 502 is in the retracted configuration, the suture anchor 510 can be driven distally towards the dilator feature 512 and into the bone hole 612. In the illustrated embodiment, the driver 504, with the distal driver member 520 thereof releasably coupled to the suture anchor 510, is activated to drive the suture anchor 510 distally into the bone hole 612. As shown in FIG. 20F, the driver shaft 516 of device 504, and therefore the distal driver member 520 of the shaft 516, can be rotated, such as by rotating the proximal handle 514 of the driver 504, as shown by an arrow 615. In the illustrated embodiment, during at least some of the rotation of the driver shaft 516 of the driver device 504, force can be applied to the proximal handle 503 of the pusher device 501, as shown by an arrow 617 in FIG. 20F. The system 500 can be configured such that a surgeon can use one hand to both rotate the driver 504 and apply force to the proximal handle 503 of the pusher device 501. In this way, the suture anchor 510 is caused to rotatably move distally towards the dilator feature 512 and into the bone 600, as threads 513 formed on the suture anchor 510 engage an interior wall of the hole 612 in the bone 600. Tension can be maintained on the terminal end portions 606*a*, 606*b* of the suture 606 while the suture anchor 510 is caused to move distally. FIG. 20G illustrates the suture anchor 510 driven distally towards the dilator feature 512 and into the bone 600. The suture 606 is secured between an interior wall of the bone hole 612 and an outer surface of the suture anchor 510.

Once the suture anchor 510 has been positioned as desired within the hole 612 in the bone 600, the driver 504 having the elongate shaft 502 coupled to the proximal handle 514 thereof can be separated from the dilator feature 512 and the suture anchor 510, as shown by an arrow 619 in FIG. 20H. The pusher device 501 is also removed. As shown in FIG. 20I, the dilator feature 512 and the suture anchor 510 remain implanted in the bone hole 612, thereby attaching the tissue 602 to the bone 600, as shown in FIG. 15I. If desired, the terminal end portions 606*a*, 606*b* of the suture 606 can be trimmed using a suitable cutting instrument, and FIG. 20I illustrates by way of example the terminal end portions 606*a*, 606*b* trimmed.

The methods and systems described herein can have different variations. For example, in each of the embodiments, multiple sutures can be used to couple tissue to bone. Also, one or more sutures can be loaded on a surgical system before or during a surgical procedure. For example, in some embodiments, a surgical system can have at least one suture pre-loaded thereto such that the surgical system in the assembled configuration includes the suture. Furthermore, in some embodiments, the dilator feature may not be used. As another variation, another feature can be used to dilate a hole in bone.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device, e.g., the shafts, can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the components of the system described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred the components are sterilized. This can be done by any number of ways known to those skilled in the art including beta or gamma radiation, ethylene oxide, steam, and a liquid bath (e.g., cold soak).

One skilled in the art will appreciate further features and advantages of the described subject matter based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A surgical system, comprising:
   an elongate shaft, a distal tip of the elongate shaft being configured to be inserted into a bone to initiate formation of a hole in the bone, and the elongate shaft having a suture retaining feature formed therein that extends proximally from an opening formed through a side of the elongate shaft;
   an implantable member having a shape that tapers in a distal direction, the elongate shaft being positioned in an inner lumen of the implantable member, and the implantable member being configured to be advanced distally into the hole initiated by the distal tip of the elongate shaft and widen the hole as the implantable member is being advanced into the hole; and
   an implantable anchor configured to be advanced distally into the hole widened by the implantable member, the elongate shaft being positioned in an inner lumen of the implantable anchor, and the distal advancement of the implantable anchor being relative to the implantable member.

2. The system of claim 1, further comprising a driver; and wherein the elongate shaft is positioned in an inner lumen of the driver, and a handle of the driver is configured to be rotated to cause the distal advancement of the implantable anchor.

3. The system of claim 1, further comprising a suture positioned in the inner lumen of the implantable anchor, positioned in the suture retaining feature, and extending through the opening.

4. The system of claim 1, wherein the implantable anchor and the implantable member are spaced a distance apart longitudinally along the elongate shaft with a gap of space being between a proximal end of the implantable member and a distal end of the implantable anchor.

5. The system of claim 1, wherein the implantable anchor includes a thread, and the distal advancement of the implantable anchor is configured to cause the thread to thread into the bone.

6. The system of claim 1, wherein an exterior surface of the implantable member tapers distally.

\* \* \* \* \*